(12) United States Patent
Hu et al.

(10) Patent No.: US 7,572,621 B2
(45) Date of Patent: Aug. 11, 2009

(54) DETECTION, CHARACTERIZATION AND TREATMENT OF VIRAL INFECTION AND METHODS THEREOF

(75) Inventors: Yu-wen Hu, Ottawa (CA); Earl Brown, Ottawa (CA)

(73) Assignee: Canadian Blood Services (CA)

( * ) Notice: Subject to any disclaimer, the term of this patent is extended or adjusted under 35 U.S.C. 154(b) by 0 days.

(21) Appl. No.: 11/248,008

(22) Filed: Oct. 11, 2005

(65) Prior Publication Data

US 2006/0115875 A1 Jun. 1, 2006

Related U.S. Application Data

(63) Continuation of application No. PCT/CA2004/000544, filed on Apr. 13, 2004.

(60) Provisional application No. 60/461,137, filed on Apr. 9, 2003, provisional application No. 60/506,779, filed on Sep. 30, 2003.

(51) Int. Cl.
*C12N 7/00* (2006.01)

(52) U.S. Cl. .................................. 435/235.1

(58) Field of Classification Search ........................ None
See application file for complete search history.

(56) References Cited

OTHER PUBLICATIONS

Natale et al., Computer-assisted analysis of molecular mimicry between human papillomavirus 16 E7 oncoprotein and human protein sequences, Immunology and Cell Biology, 2000, 78:580-585.*
Maksyutov et al., Searching for Local Similarities between HIV-1 and Human Proteins. Application to Vaccines, Molecular Biology, 2002, 36(3):346-358.*
Lou et al., Molecular mimicry: a mechanism for autoimmune injury, FASEB, 1992, 6:840-844.*
Kammer et al., Molecular Mimicry of Human Cytochrome P450 by Hepatitis C Virus at the Level of Cytotoxic T Cell Recognition (Journal of Experimental Medicine, 1999, 190(2):169-176.*
Chew et al., Severe acute respiratory syndrome coronavirus and viral mimicry, The Lancet, 2003, 361:2081.*
Lawson, Evidence for mimicry by viral antigens in animal models of autoimmune disease including myocarditis, Cell and Molecular Life Science, 2000, 57:552-560.*
Barnett & Fujinami, "Molecular Mimicry: A Mechanism for Autoimmune Injury," *FASEB* 6(3):840-844 (1992).
Beck & Barrell, "Human Cytomegalovirus Encodes a Glycoprotein Homologous to MHC Class-I Antigens," *Nature* 331:269-272 (1988).
Chew et al., "Severe Acute Respiratory Syndrome Coronavirus and Viral Mimicry," *Lancet* 361:2081 (2003).
Kato et al., "Genetic Drift in Hypervariable Region I of the Viral Genome in Persistent Hepatitis C Virus Infection," *J. Virol.* 68(8):4776-4784 (1994).
Natale et al., "Computer-Assisted Analysis of Molecular Mimicry Between Human Papillomavirus 16 E7 Oncoprotein and Human Protein Sequences," *Immunol. Cell Biol.* 78:580-585 (2000).
Oleszak, "Molecular Mimicry Between Fc Receptors and Viral Antigens," *Archivum Immunoloqlae et Therapiae Experimentalis* 42:83-88 (1994).
Zhao et al., "Molecular Mimicry by Herpes Simplex Virus-Type I: Autoimmune Disease After Viral Infection," *Science* 279:1344-1347 (1998).

\* cited by examiner

*Primary Examiner*—Bruce Campell
*Assistant Examiner*—Nicole Kinsey White
(74) *Attorney, Agent, or Firm*—Nixon Peabody LLP

(57) ABSTRACT

A method of detecting, characterizing and treating viral infection is provided. In particular, a strategy of molecular mimicry is provided for characterizing viral behavior and/or a predisposition for a given viral outcome in vivo. Novel compositions are also provided for detecting, characterizing and treating viral infections.

6 Claims, 34 Drawing Sheets

Fig. 1a.

1, Germline antibody g21: 27.4% identity in 62 aa overlap

```
              10        20        30        40        50        60        70        80
1a   ETYVTGGAAGRGVATITGLFSQGPQQKIQLVNTNGSWHINSTALNCNDSLKTIGWIAGLFYRNNFNSSGCPERLASCRRLTDF
                 :         :  :::::.::::.:           :  :::::::::::::::::::::::::::
2ig2L QSVLTQPPSASGTPGQRVTISCSGTSSNIGSSTVNWYQQLPGMAPKLLIYRDAMRPSGVPDRFSGSKSGASA
              10        20        30        40        50        60        70
```

2, Antibody V-J: 28.8% identity in 62 aa overlap

```
              10        20        30        40        50        60        70        80
1a   ETYVTGGAAGRGVATITGLFSQGPQQKIQLVNTNGSWHINSTALNCNDSLKTIGWIAGLFYRNNFNSSGCPERLASCRRLTDF
                 :         :  :::::.::::.:           :  ::::.::::::::::::::::::::::
V-J           SGTPGQRVAISCSGRSSKIGSNTVNWYQQLPGTAPKLLIYRNNQRPSGVPDRLSVCRNIEAF
              10        20        30        40        50        60        70
```

3, functional antibody: 38.27% identity in 81 aa overlap

```
     32        40        50        60        70        80        90       100
2a   VN-TNGSWHINRTALNCNDSLHTGFIASLFYTHSFNSSGCPERMSACRSIEAFRVGWGALQYEDNVTNPEDMRPYCW-HY
        : :        ::::.         ::::::::::::   ::::: :              :         ::
fvdA VTITCRASQDVNTAVAWYQQKPGKAPKLLIYSASFLESGVPSRFSGSGSRSGTDFTLTISSLQPEDFATY------YCQQHY
     20        30        40        50        60        70        80        90

2a   --PP---RQCGVVSAKTVCGP-VYCFTPS
          ::      ::  ::: 
fvdA TTPPTFGQGTKVEIKRTVAAPSVFIFPPS
     100       110       120       130
```

Fig. 1b.

```
IgVκ
       |       FR1             |           CDR1         |           FR2          |   CDR2   |              FR3                |    CDR3
       1          10          20           30          40           50          60           70          80           90        100        110
κ1     DIQMTQSPSTLSASVGDRVAITCRA  SQNI  SSWLAWYQQKPGKAPKVLIYKSS   LESGVPSRFSGSGSGTDFT//YCQQYNTFF
κ2     DIVLTQSPLSLPVTPGEPASISCRS  SQSLNS**LNWYLQKPGQSPZLLIYALSNRASGVPDRFSGSGSGTDFT//YCNZALQAP
κ3     EIVMTQSPATLSVSPGESATLSCRA  SQSV  SSNLAWYQQKPGQPPKLLIYGASTRATGIPARFSGSGSGTEFT//YCQQYNNWP
κ4     QIVMTQSPDSLAVSLGERATINCKS  SQSILY**LAWYQQKPGQPPKLLIYCASTRESGVPDRFSGSGSGTDFT//YCQQYNLP
g2L    QSVLTQPPSA  SGTPGQRVTISCSGTSSNIGSSTVNWYQQLPGMAPKLLIYRDAM  RPGVPSDFSGSGRGTSFS//YCAAWDVSL
vda    DIQMTQSPSSLSAAVGDRVTITCRA  SQDVN  TAVAWYQQKPGKAPKLLIYSASFLESGVPSRFSGSGRGTDFT//YCQQHYTPP
V-J    MAEL Q  PPSVSGTPGQRVAISCSGRSSKIGSNTVNWYQQLPGTAPKLLIYRNNQR  PGVPDRFSASKSGTSAS//YCLAWDDNV
Mu1    DIVMTQSPKFMSTSVGDRVTITCKA  SQD  VSTAVVWYQQKPGQSPKLLIYWASTRHIGVPDRFAGSGSGTDYT//YCQQHYSPP
Mu2    DIVLTQSPSSLSASLGDTITITCHA  SQNIN  VWLSWYQQKPGNIPKLLIYKASNLHTGVPSRFSGSGSGTGFT//YCQQGQSYP
Mu3    DIQMTQSPSSLSASLGDRVTISCSA  SQDINKY  LNWYQQKPDGAVKLLIFYTSSLHSGVPSRFSGSGSGTDYS//YCQQYEKLP
Mu4    DIQMTQSPSSLSASLGDRVTISCSA  SQDINKY  LNWYQQKPDGAVKLLIFYTSSLHSGVPSRFSGSGSGTDYS//YCQQYEKLP
```

```
       1          10          20           30          40           50          60           70          80           90        100        110
1a     AAGRGVATITGLFSQGPQQKIQLV//SWHINSTALNCNDSLKTGWIAGLFYRNNFNSSGCPERLASCRRLTDFA//YCW/HY PP
1b     VASSTQSLVSWL  SQGPSQKIQLI//SWHINRTALNCNDSLQTGFIAALFYAHRFNASGCPERMASCRPIDKFA//YCW/HYAPQ
2a     SAAHTTRSFVGLFSAGAQQNIQLI//SWHINRTALNCNDSLHTGFIASLFYTHSFNSSGCPERLSACRSIEAFR//YCW/HY.PP
2b     QVGQTVSGFAGMFRSGSRQNIQLI//SWHINRTALNCNDSLQTGFMASLFYANKFNSSGCPERLSSCRRLDDFR//YCW/HY.PP
3a     AAHATRGLTSLF  SVGAQQKLQLV//SWHINSTALNCNESINTGFIAGLFYYHKFNSTGCPQRLSSCKPITFFK//YCW/HYAPR
3b     AAQATAGFTSFF  TRGPSQNLQLV//SWHINSTALNCNDSLNTGFIAGLFYYHKFNSSGCPERMSSCKPITYFN//YCW/HYAPR
4a     VGRSTAGLANLF  SSGSKQNLQLI//SWHINRTALNCNDSLNTGFIAGLFYYHKFNSSGCSERLACCKSLDSFG//YCW/HYAPR
5a     VGQGLKSLTSFF  NPGPQRQLQFV//SWHINRTALNCNDSLQTGFMYNSKFNSSGCPERMSSCRPLAAFD//YCW/HYPPR
6a     VSQTTSGFASLL  TPGAKQNIQLI//SWHINRTALNCNDSLQTGFLASLFYTHKFNSSGCPERMAACKPLAEFR//YCW/HYAPR

|    MHD1    |         MHD 2          |         MHD3         |          MHD4          |
```

Fig. 1c.

```
          1         10         20
IgVL      DIVMTQSPSSLSVSLGDRVT
          QVQL VTTAAMPATV ETAS
          ESEV  P LT AT P QK K
           AA    E DF VG T  Q R
                             S
```

| HCV HVR1 | 10        20      27 | Identity | to IgVL |
|---|---|---|---|
|  | AAARTTSGLTSLFSPGASQN | 10/20 | 50% |
|  | SQGHAARRFAGFLTS PK K | 4/20 | 20% |
|  | TVSQNVASIVNI AL SQ R | 6/20 | 30% |
|  | VT YG HTV     NR  R  | 2/20 | 20% |
|  | Q    S Q           A | 1/20 | 10% |
| Cons. | QAA TVSTLT   SPG R K | 14/20 | 70% |

Fig. 1d.

| IgVL | 1                  20 | Identity | to CAR |
|---|---|---|---|
| κ1 CAR | DIQMTQSPSTLSASVGDRVA | | |
| DEE | ....S...............T | 18/20 | 90% |
| κ2 TEW | ..V.....LS.PVTP.EPAS | 9/20 | 45% |
| κ3 CLL | E.V.....A.....P.E.AT | 12/20 | 60% |
| κ4 B17 | ..V.....DS.AV.L.E.AT | 11/20 | 55% |
| g21 | QSVL..P..ASGT P.Q..T | 7/20 | 35% |
| 1fv | .........S...A..D..T | 16/20 | 80% |
| V-J | MAE T S.PSV.GTP.Q..A | 5/20 | 25% |

Fig. 1e.

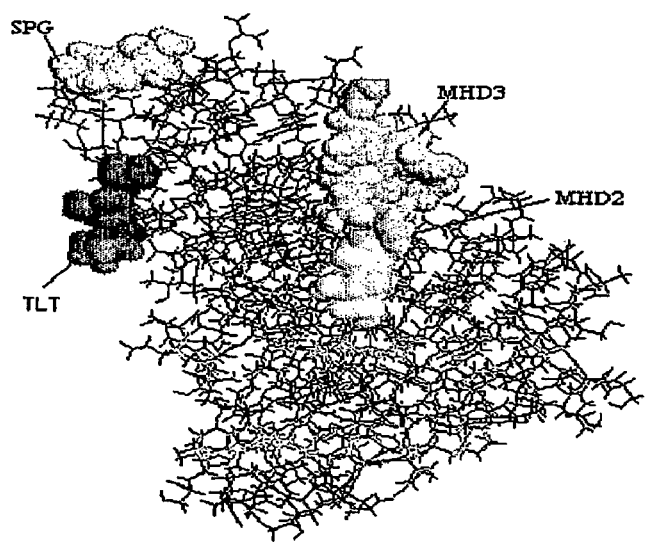

Fig. 2a.

```
         FR1                          CDR1               FR2                  CDR2             FR3                   CDR3
    1         10        20             30         40              50           60         70           90
κ1   DIQMTQSPSTLSASVGDRVAITCRA  SQNI   SSWLAWYQQKPGKAPKVLIYKSS   LESGVPSRFSGSGSGSGTDF//YCQQYNTFF
κ2   DIVLTQSPLSLPVTPGEPASISCRS  SQSLNS//LNWYLQKPGQSPZLLIYALSNRASGVPDRFSGSGSGTDF//YCNZALQAP
κ3   EIVMTQSPATLSVSPGESATLSCRA  SQSV   SSNLAWYQQKPGQPPRLLIYGASTRATGIPARFSGSGSGTEF//YCQQYNNWP
κ4   QIVMTQSPDSLAVSLGERATINCKS  SQSILY//LAWYQQKPGQPPKLLIYCASTRESGVPDRFSGSGSGTDF//YCQQYYNLP
g2L  QSVLTQPPSA.SGTPGQRVTISCSGTSSNIGSSTVNWYQQLPGMAPKLLIYRDAM RPGVPSDFSGSGRGTSF//YCAAWDVSL
vda  DIQMTQSPSSLSAAVGDRVTITCRA..SQDVNTAVAWYQQKPGKAPKLLIYSASFLESGVPSRFSGSGRGTDF//YCQQHYTPP
V-J  MAEL Q PPSVSGTPGQRVAISCSGRSSKIGSNTVNWYQQLPGTAPKLLIYRNNQR PGVPDRFSASKSGTSA//YCLAWDDNV
```

Fig. 2b.

```
       10         20         30         40         50         60         70         80         90    100
S1 17*RGVATITGLF SQGPQQKIQLVNTNGSWHINSTALNCNDSLKTGWIAGLFYRNNFNSSGCPERLASCRRLTDF//YCW HY PP
 3 ----------- ----A----- ---------- ---------- ---------- ---------- ---------- ---------//--- -- --

A3
18 ----------- ---------- ---------- ---------- ----N----- ---------- ---------- ---------//--- -- --
12 ----------- -------A-- ---------- ---------- ----N----- ---------- ---------- ---------//--- -- --

A2
19 ------A---- ---P------ ---------- ---------- ----N----- ---R------ ---------- ---------//--- -- --
 2 -AA-GLANI-- ---P--K--- ---------- ---------- ----N----- ---Y------ ---------- ---------//--- -- --
 2 -AA-GLANI-- -A-AK-N--I ---------- ---------- ----N----- ---R------ ---------- ---------//--- -- --
 1 --A-GIAD--- ---L--K--- ---------- ---------- ---------- ---------- ---------- ---------//--- -- --

A1
12 ----------- ---P------ ---------- ---------- ----N----- ---R------ ---------- ---------//--- -- --
 7 ----------- ---S------ ---------- ---------- ---------- ---R------ ---------- ---------//--- -- --
 6 -AA-G-A---- ---S------ ---------- ---------- ---------- ---R------ ---------- ---------//--- -- --
 3 -AA-AFA---- ---S------ ---------- ---------- ---------- ---R------ ---------- ---------//--- -- --

MHD1              MHD 2                    MHD3                           MHD4
```

Fig. 3a.

```
          1                    20
IgVL   DIVMTQSPSSLSVSLGDRVT
       QVQL  VTTAAMPATV ETAS
       ESEV   P  LT  AT P  QK K
         AA      E  F   G    Q
                        S
```

Fig. 3b.

```
Quasispecies (1a) time P.I
           10        20        27   (days)   Identity to IgVL
S1  75%  AAGRGVATITGLFSQGPQQK          0      8/20      40%
    10%  VT..................                 7/20      35%
    10%  ........A...........                 8/20      40%
     5%  ....AA.GIAG...S.....                 6/20      30%

A1  42%  VT......A....P......         36      8/20      40%
    25%  .............P......                 9/20      45%
    21%  SPA.AA.G.A....S.....                 5/20      25%*
    11%  APA.AA.AFA....S.....                 5/20      25%*

A2  79%  VT......A....P......         46      8/20      40%
     8%  VT..AA.G.ANI..P.AK.N                 5/20      25%*
     4%  VT..........A.......                 7/20      35%
     4%  VT.G.A.G.AD...L.....                 6/20      30%*
     4%  TA..AA.G.ANI..P.AK.N                 6/20      30%*

```
Quasispecies (2c)
    69%     SAGHSLPGISNLFAPGAQQH      0      7/20     35%
    31%     T...................            7/20     35%
    73%     ....................    180      7/20     35%
    27%     ....................             7/20     35%
    14%     ..AYNT.SLTSI.SV..R.K    360     11/20     55%
     7%     ..AR.TSPLTSI.SS.PK.N            11/20     55%
    18%     ..A.NTWSLTS.....SK.N            10/20     50%
     3%     ..AYNT.SLTSI.SV.PK.N            10/20     50%
     7%     ..AR.TL.LTS...P.PK.N            11/20     55%
     7%     ..AYNT.SLTS..SA..R.K            10/20     50%
    11%     ..ACNTL.LTS..SA..R.K            10/20     50%
    25%     ..AR.TL.LTS...VA.PK.N            9/20     45%
     3%     ..AR.TSRLTSI.SA.PK.N            11/20     55%
```

Fig. 3d.

```
Patients
    1     TAARTVSGFTSLFSVGANQN      0      8/20     40%
          ...H................     70      8/20     40%
          ............A.......    217      7/20     35%

2     TAAHTVSGLTGLFSIGAKQN      0      8/20     40%
          ....................    343      8/20     40%
          ....................    399      8/20     40%

3     SAAKAILGITGLFSPGPRQN      0      7/20     35%
          ....................    294      7/20     35%
          ....................    441      7/20     35%

4     SVAQAASTLTSLFSPGAKQD      0      9/20     45%
          .............T......    252      8/20     40%

5     SAAHTAAGLASLFTSGAKQD      0      8/20     40%
          ....................    245      8/20     40%

6     QAGHTTQGAASLFAPGAAEK      0      9/20     45%
          ........I.........R      12      7/20     35%
          ........PY....SV.P...     52      9/20     45%
```

Fig. 4a.

```
IgVL  1          10          20              Identity to HCV
      DIVMTQSPSSLSVSLGDRVTI                   8/20    40%
      QVQL VTTAAMPATV ETASL                   4/17    24%
        SEV  P LT AT P QK KM                  5/13    38%
         AA    E DF VG T  Q                   3/9     33%
```

Fig. 4b.

```
              s
         10         20      27    Time(days)   Identiy to IgVL
PEGGY  SGRSTHGLVSL-FNLGAQQKV         0          7/20    35%
       ...........-..........       29          7/20    35%
       ...........-..........       41          7/20    35%
       ...........-..........       62          7/20    35%
       ...........-..........       76          7/20    35%
       ............-..P.....I       91          8/20    40%
       ......S.....-..P.....I     1189          9/20    45%
       ......S.....-..P.....I     1433          9/20    45%
       ......S.....-..P.....I     1433          9/20    45%
       ......S.....-.SP.....I     2210         10/20    50%
       ......S.....-.SP.G...I     3432         10/20    50%

HANS   ............-..........      24          7/20    35%
       ............-..........      46          7/20    35%
       .SH..R.F...-.SP........     1166          9/20    45%
       ...H..RSF...-.SP....N.      2200          9/20    45%
       ...H..RSF.F.-.SP....N.      3401          9/20    45%
```

Fig. 4c.

```
         10         20      27    Time(years)   
       SAGRTVSGLVGLLAPGAKQN           1          7/20    35%
       ...H.....A..F.......           2          8/20    40%
       ...R.....A..F.......           3          8/20    40%
       ...R.....A..F.......           4          8/20    40%
       ...R.....A..F.......           5          8/20    40%
       ...R.....AS.F.......           6          8/20    40%
       ...R.....AS.F.......           7          8/20    40%
       ...R.....AS.FT......           8          9/20    45%
       ...R....FAS.FT......           9          9/20    45%
       ...R.....A..FT......          10          9/20    45%
       ...R.....A..FT......          11          9/20    45%
       ...R.....A..FT......          12          9/20    45%
```

Fig. 5a.

```
            4              17
IgVL   MTQSPSSLSVSLGD
       L  VTTAAMPATV  E
       V  P  LT  AT  P  Q
             E  DF  VG  T  S
```

| Epitop | | | Time (Month) p.d./P.I | Identity to IgVL | | Ab* |
|---|---|---|---|---|---|---|
| 1 | HSVRGFTSLFS | | 0 | 3/11 | 27% | ++++ |
| 2 | .......AGS | | | 4/11 | 36% | ++++ |
| 1 | .....L..... | | 6 | 4/11 | 36% | +++ |
| 2 | ..L........ | | | 5/11 | 54% | ++ |
| 1 | .G...L..... | | 8 | 4/11 | 36% | ++ |
| 2 | ..L........ | | | 5/11 | 54% | ++ |
| 1 | .G.S.L..... | | 11 | 5/11 | 45% | - |
| 2 | .. S.L...... | | | 6/11 | 54% | - |

| | | | | | | Variants |
|---|---|---|---|---|---|---|
| 1 | RAAAGFAGLFS | 1.2 | 2/11 | 18% | Eliminated |
| 2 | .......QGP | | 3/11 | 27% | |
| 1 | .GVATIT.... | 2.4 | 4/11 | 36% | Persistent |
| 2 | .......P.. | | 6/11 | 54% | |

| 1 | HSLPGISNLFA | 0 | 2/11 | 18% | Eliminated |
|---|---|---|---|---|---|
| 2 | .......PGA | | 4/11 | 36% | |
| 1 | YNT.SLTSI.S | 12 | 5/11 | 45% | Persistent |
| 2 | .......V.. | | 6/11 | 54% | |
| 1 | RNTSPLTSI.S | | 7/11 | 63% | |
| 2 | .......S.P | | 6/11 | 54% | |

Fig. 6A.

```
k1   DIQMTQSPSTLSASVGDRVAITCRA SQNI SSWLAWYQQKPGKAPKVLIYKSS LESGVPSRFSGSGSGTDF
k2   DIVLTQSPLSLPVTPGEPASISCRS SQSLNS**LNWYLQKPGQSPZLLIYALSNRASGVPDRFSGSGSGTDF
k3   EIVMTQSPATLSVSPGESATLSCRA SQSV SSNLAWYQQKPGQPPRLLIYGASTRATGIPARFSGSGSGTEF
k4   QIVMTQSPDSLAVSLGERATINCKS SQSILY**LAWYQQKPGQPPKLLIYCASTRESGVPDRFSGSGSGTDF
g2L  QSVLTQPPSA SGTPGQRVTISCSGTSSNIGSSTVNWYQQLPGMAPKLLIYRDAM RPGVPSDFSGSGSGRTSF
vda  DIQMTQSPSSLSAAVGDRVTITCRA SQDVN TAVAWYQQKPGKAPKLLIYSASFLESGVPSRFSGSGRGTDF
V-J  MAEL Q PPSVSGTPGQRVAISCSGRSSKIGSNTVNWYQQLPGTAPKLLIYRNNQR PGVPDRFSASKSGTSA
```

Fig. 6B.

```
      1              10             20
      DIVMTQSPSSLSVSLGDRVT
      QVQL  VTTAAMPATV  ETAS
      ESEV  P  LT AT  P  QK  K
      AA    E  DF VG   T     Q   R
```

Fig. 6C.

```
                                                                                           Identity to Ig
S-Dir        1         10        20        30        40        50        60      70       HVR1%    E2%
A1 (28   ETYVTGGAAGRGVATITGLFSQGPQQKI//TNGSWHINSTALNCNDSLKTGWIAGLFYRNNFNSSGCPER   40.0     42.6
clones)
14.3%    T......VT..........S..........................N...........R..........   35.0     39.3
 7.1%    T......VT..........A..........................N...........R..........   35.0     39.3
 3.6%    .......VT..........P..........................K...........R....P.....   40.0     40.9
 3.6%    T......VT..........P..........................N...........Y..........   40.0     40.9
 3.6%    .......AA..........A..........................K...........N..........   35.0     40.9
 3.6%    T......VT....N.....S..........................N...........R..........   35.0     39.3
 3.6%    .......AA..........A..........................K...........N..........   40.0     42.6
 3.6%    T......AA..........S..........................N......L....R..........   40.0     40.9
 3.6%    .......VT..........P..........................N...........R..........   40.0     39.3
 3.6%    .......AA..........H..........................K...........N..........   40.0     42.6
 3.6%    T.DIS.KTAA.AA.GLANI.P.AK.N....................N...........Y..........   35.0     39.3
 3.6%    ....APP.AA.G.A.....P..........................N...........R..........   30.0     37.8
 3.6%    .......AA..........P..........................K...........Y..........   45.0     42.6
 3.6%    T..APA.AA.G.A......P..........................N...........R..........   30.0     37.8
 3.6%    .......AA..........P..........................N...........R..........   40.0     40.9
 3.6%    T......VT..........A..........................N...........Y..........   35.0     39.3
 3.6%    G......VT..........A..........................N...........R..........   35.0     39.3
 3.6%    T..APA.AA.AFA......S..........................N...........N..........   30.0     37.8
 3.6%    .......AA..........T....P..H..................K...........Y..........   40.0     40.9
 3.6%    T..TPA.AA.G.A......S..........................N...........R..........   30.0     37.8
 3.6%    ...PA.AA.G.T.L.....S..........................N...........R..........   30.0     37.8
 3.6%    .......AAA.........P..........................K...........R..........   50.0     44.3
 3.6%    T......VT....T.....P..........................N...........R..........   40.0     40.9
```

Fig. 6C (continued)

A2
(24 clones)

| % | | | | | | | | | |
|---|---|---|---|---|---|---|---|---|---|
| 8.3% | T.DIS.KTA.RAA.GLANI..P.AK.N...I... | | | Y... | 35.0 | 39.3 |
| 4.2% | T..... | AP... | ....A..... | ..P..... | ........ | N... | ....... | 40.0 | 42.6 |
| 4.2% | T..... | AA... | ....T..... | ..P..H.. | ........ | K... | ....... | 40.0 | 42.6 |
| 4.2% | T..... | VT... | ....A..... | ..P..... | ........ | N... | ....R.. | 40.0 | 40.9 |
| 4.2% | T..... | VT... | ....T..... | ..A..... | ........ | .... | ....... | 35.0 | 39.3 |
| 4.2% | E..... | AA... | ....T..... | ..A..... | ........ | N... | ....R.. | 40.0 | 40.9 |
| 4.2% | A..... | VT... | ....T..... | ..A..... | ........ | N... | ....Y.. | 35.0 | 39.3 |
| 4.2% | S..TS | VA... | QT.GLAS..P..H.. | ...I.... | N... | ....Y.. | 35.0 | 39.3 |
| 4.2% | S..... | VA... | QT.GLAS..P..H.. | ...I.... | N... | ....R.. | 35.0 | 39.3 |
| 4.2% | T..... | VT... | ....A..... | ..S..... | ........ | N... | ....R.. | 35.0 | 39.3 |
| 4.2% | A..... | VT... | ....T..... | ..A..... | ........ | N... | ....Y.. | 35.0 | 39.3 |
| 4.2% | S..... | VA... | QT.GLAS..P.AH.. | ........ | N... | ....R.. | 35.0 | 39.3 |
| 4.2% | T..... | VT... | ....T..... | ..S..... | ........ | N... | ....Y.. | 35.0 | 39.3 |
| 4.2% | T..... | AP... | ....A..... | ..S..... | ........ | N... | ....R.. | 35.0 | 39.3 |
| 4.2% | T..... | VT... | ....A..... | ..S..... | ........ | N... | ....R.. | 40.0 | 40.9 |
| 4.2% | T..... | AA... | ....T..... | ..P..... | ........ | K... | ....Y.. | 40.0 | 40.9 |
| 4.2% | T..... | VT... | ....T..... | ..P..... | ........ | N... | ....R.. | 35.0 | 40.9 |
| 4.2% | T..... | VT... | ....T..... | ..A..... | ........ | N... | ....N.. | 40.0 | 40.9 |
| 4.2% | A..... | AVT.. | A.G.AD..L.. | ........ | N... | ....R.. | 30.0 | 37.8 |
| 4.2% | E..... | AA... | ....T..... | ..Q..... | ........ | N... | ....N.. | 40.0 | 42.6 |
| 4.2% | E..... | AA... | ....T..... | ..A..... | ........ | K... | ....N.. | 40.0 | 42.6 |
| 4.2% | E..... | AA... | ....A..... | ..P..... | ........ | K... | ....N.. | 45.0 | 44.3 |
| 4.2% | E..... | AA... | ....A..... | ..S..... | ........ | N... | ....R.. | 40.0 | 40.9 |

Fig. 6C (continued)

```
S-Dir  ETYVTGGAAGRGVATITGLFSQGPQQKI//TNGSWHINSTALNCNDSLKTGWLAGLFYRNNFNSSGCPER  40%          42%
A3 (29 clones)
44.8%  A......VT.........T....Q.....................N...................35.0         41.0
13.8%  A......AA.........T....A.....................N...................40.0         42.6
10.3%  E......AA.........T....A.....................N...................40.0         42.6
10.3%  A......AA.........T....Q.....................N...................40.0         42.6
 7.0%  A......AA.........T....Q.....................K...................40.0         42.6
 7.0%  A......VT.........T....Q.....................K...................35.0         41.0
 3.4%  T......VT.........A....S.....................N...................35.0         41.0
 3.4%  A......VT.........T....S.....................R...................35.0         41.0
 3.4%  E......AA.........T....A.....................N...................40.0         42.6

After Interferon treatment
001-03-13

S-Dir  ETYVTGGAAGRGVATITGLFSQGPQQKI//TNGSWHINSTALNCNDSLKTGWLAGLFYRNNFNSSGCPER  40%          42%
A4 (10 clones)
80%    T.DIS.KTAA.AA.GF.NI..P.AK.N...................N.........Y........35.0         39.3
10%    T.DIS.KTAA.VA.GF.NI..P.AK.N...................N.........Y........35.0         39.3
10%    T.DIS.KTAV.AA.GF.NI..P.AK.N...................N.........Y........30.0         37.7

2001-04-23
S-Dir  ETYVTGGAAGRGVATITGLFSQGPQQKI//TNGSWHINSTALNCNDSLKTGWLAGLFYRNNFNSSGCPER  40%          42%
A5 (10 clones)
60.0%  T.DTS.RTAA.AA.GLTTIFSPGAKQN...................N.........Y........40.0         41.0
30.0%  T.DIS.RTAA.AA.GF.TI..P.AK.N...................N.........Y........35.0         39.3
10.0%  T.DIS.RTAA.AA.RL.TI..P.AK.N...................N.........Y........40.0         41.0
```

Figure 7.

| SAMPLE ID | # of clones | AMINO ACID SEQUENCE | VIRAL LOAD (copies/ml) week[b] | | |
|---|---|---|---|---|---|
| | | | 0 | 1 | 8 |
| WT-1b | | PSLKATCTTHHDSPDADLIEANLLWRQEMGGNITRVESEN | | | |
| 03 | 1 | PSLKATCTTCHDSPDADLIEANLLWRQEMGGNITRVESEN | 860000 | 860000 | 860000 |
| | 2 | ---------------------------------------- | | | |
| | 3 | ---------------------------------------- | | | |
| | 4 | ---------------------------------------- | | | |
| | 5 | ---------------------------------------- | | | |
| | 6 | ---------------------------------------- | | | |
| | 7 | ---------------------------------------- | | | |
| | 8 | ---------------------------------------- | | | |
| 17 | 1 | --------H-----V------------------------ | 860000 | 454000 | 171000 |
| | 2 | --------H-----V------------------------ | | | |
| | 3 | --------H-----V------------------------ | | | |
| | 4 | --------H-----V------------------------ | | | |
| | 5 | --------H-----V------------------------ | | | |
| | 6 | --------H-----V------------------------ | | | |
| 56 | 1 | ----------R-A-------------------------- | 72800 | 159000 | 599 |
| | 2 | ----------R-A-------------------------- | | | |
| | 3 | ----------R-A-------------------------- | | | |
| | 4 | ----------R-A-------------------------- | | | |
| | 5 | ----------R-A-------------------------- | | | |
| | 6 | ----------R-A----------------V--------- | | | |
| | 7 | ----------R-A-------------------------- | | | |
| | 8 | ----------R-A-------------------------- | | | |
| 65 | 1 | ----------AN------E-------------------- | 860000 | 71300 | 599 |
| | 2 | ----------AN------E------P------------- | | | |
| | 3 | ----------AN------E-------------------- | | | |
| | 4 | ----------AN------E-------------------- | | | |
| | 5 | ----------AN------E-------------------- | | | |
| | 6 | ----------AN------E------P------------- | | | |
| | 7 | ----------AN------E-------------------- | | | |
| | 8 | ----------AN------E-------------------- | | | |

Figure 8.

```
Sample 65 - sensitive              ----------------AN------E------------
Sample 56 - sensitive              ----------------R-A------------------
WT-1b                              ----------------H--------------------
Sample 03 - resistant              PSLASSSASQLSAPSLKATCT-TCHDSPDADLIEANLLWRQEMGGNITRVESEN
                                    .:  .::  ::  .  :::  .   .:  .: .:: .:::  .
immunoglobulin IgG2A               DIVLTQSPSSLSA-SLGDTITITCHASQN---INVWLSWYQQKPGNIPKLLIYK
```

Fig. 10

Ly1 AAG33824  (hcv lymphoma) rearranged
Ly2 AF372843_1(hcv lymphoma) full length
Ly3 AF372842_1(hcv lymphoma) full length
Ly4 AAG33835  (hcv lymphoma) rearranged
Ly5 AAG33834  (hcv lymphoma) rearranged
Ly6 AAG33833  (hcv lymphoma) rearranged
Ly7 AAG33832  (hcv lymphoma) rearranged
Ly8 AAG33830  (hcv lymphoma) rearranged WA Anti-idiotype antibodies (rheumatoid factor) found in cases of type II cryoglobulinemia.
Wa1 AAL17964.
Wa2 AAA03468

IgVLκ
```
    DIVMTQSPSSLSVSLGDRVT
    QVQL  VTTAAMPATV ETAS
    ESEV   P  LT AT P  QK  K
     AA    E DF VG T    Q  R
                        S
```
HCV HVR
```
          10          20     27
    AAARTTSGLTSLFSPGASQN
    SQGHAARRFAGFLTS  PK K
    TVSQNVASIVNI   AL SQ R
    VT  YG HTV       NR  R
     Q   S Q                A
    QAA-TVSTLT---SPG-R-K
```

Fig. 10 (continued)

```
L1              SQIVSSSYLAWYQQKPGQAPRLLIYGASSRATGIPDRFSGSGSGTDFT//YCQQYGSSP
L2  EIVLTQSPGTLSLSPGERATLSCRA QSVTSNYLAWYQQKPGQAPRLLIYGASSRATGIPDRFSGSGSGTDFT//YCQQYDSSP
L3  DIQMTQSPSSLSASVGDRVTITCRA SQSI SYLNWYQQKPGKAPKLLIYAASSLQSGVPSRFSGSGSGTDFT//YCQQSYSTP
L4              TLSCRA QSISSTYLGWYQQKPGQPPRLLIYGASSRATGIPDRFSGSGSGTDFT//YCQQYGSSP
L5              QSVSSSYLAWYQQKPGQKPGRTPRLLIYGASSRATGIPDRFSGSGSGTDFI//YSCQQYGSSP
L6              SVSSSYLAWYQQKPGQAPRLLIYGASTRATGIPDRFSGSGSGTDFT//YCQQYGSSP
L7            A SQTLSSSYLAWYQQIPGQKPGKAPKRLIYVASSLQSGVPSNFSGTGSGTEFT//YCLQYNSYP
L8            ITCRA SQDIRND LGWYQQKPGKAPKLLIYGASSRATGIPNRFSGSGSGTDFT//YCQQYGSSP
WA1 EIVLTQSPGTLSLSPGERATLSCRA QSVSSSYLAWYQQKPGQAPRLLIYGASSRATGIPARFSGSGSGTEFT//YCQQYNNWP
WA2 EIVMTQSPATLSVSPGERATLSCRA SQSVSTNLAWYQQQPGQAPRLLIYGASTRATGIPARFSGSGSGTEFT//YCQQYNNWP
```

Fig. 12.
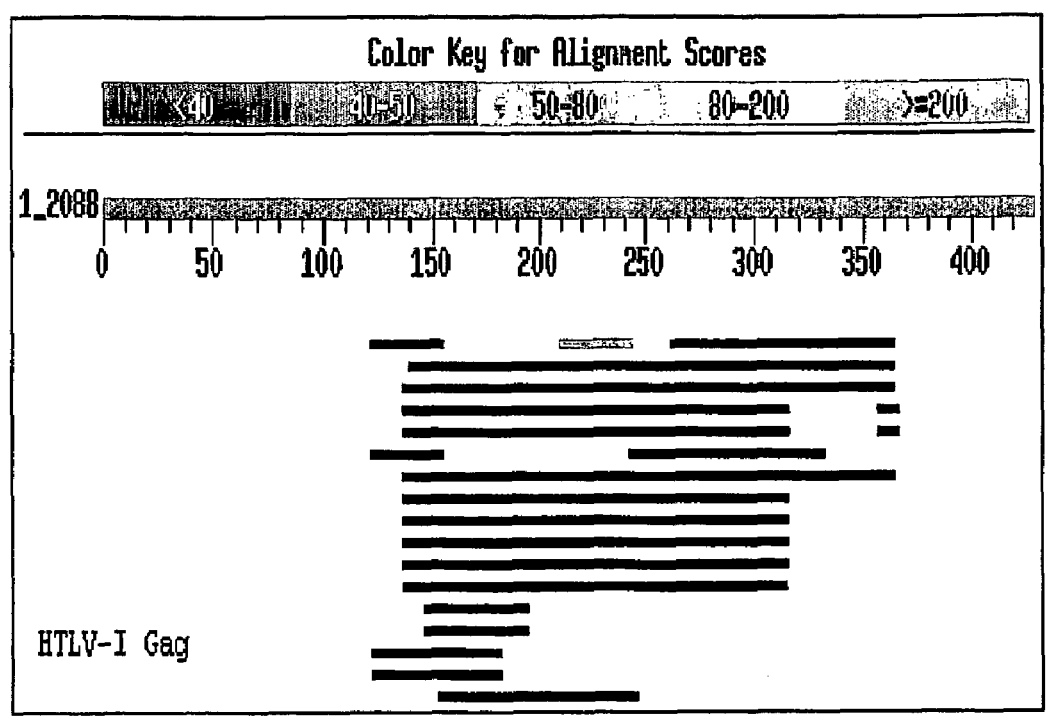
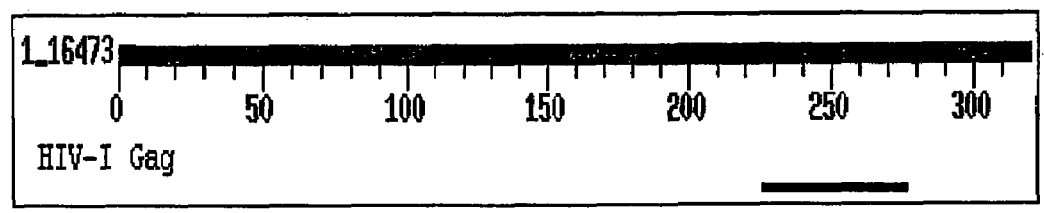

Fig. 13.

```
7          16    (21      34)*  39      (40-89)
SRSASP-IPRPPRGLAA          LEPGPS
S  SA+P  PR P    LAA       L+PGPS
   RS++P  IPRPP
        P  IP  PP
        P   P  PPRG 90                                                      132
TQA----QIPSRPAPPPPSSSTHDPPDSDPQIPPPYVEPTAPQV-LPV
TQA    Q     APPP  S       PP  +     PPP      P  APQ
   Q    Q P   PAPPPP          PP    PQ PPP
   QA        P+  P  PPPP      PP     P   PPP     P+A PQV LPV
             PSRPAPPPPSSSTHDPP      +P  IPPP
                  PPPPSSS
                APPPP+++
            +PSRPAPPPP-SS----  PP 123       130  (133-149)   150                166     171 (172-210)
EPTAPQVL                LQAIKQEVSQAAPGSPQFMQTI
EP   PQVL                 L  A   Q  VSQA    SPQ
                               QAAPG  PQ
                               AAPGSP
                                        PQFM  T+

211                                  244 (245-310)311         319
EAETRG ITGYNPLAGPLRVQANNPQQQGLRREYQ              CQKLLQARG
EAETRG+TGY+P+ A  PLR+Q+ NNP  QQGLRREYQ           C  KL  Q  RG 322       330   (331-347)  348                              370
NSPLGDMLR                  PKKPPPNQPCFRCGKAGHWSRDC (371-382)
NSPLGD+ LR                 PKKP  P  Q   C+RCGK   GHWS ++C
                                  CF+C   K+ GHW+ +-C
                                  CFRCGK  GH 383         410    415
PEPEPEEDALLL-DLP
PEPEPEE+   L
      PE  DALLL DL
            LLLDLP
```

Fig. 14.

| (1-35) | 44 | 49 | 69 | 77 | (84) | 110)* |
|---|---|---|---|---|---|---|
| ERLQALQHLV | | EAGHIEPYTGPGNNPVFPVKK | | IHDLRATN | | LQTIDLR |
| E+LQAQQ LV | | EAGH++P T P N PVF +KK | | +HDLRA N | | L IDL+ |

| 126 | 132 | 137 | 146 | 170 |
|---|---|---|---|---|
| DAFFQIPLPK | FAFTV P | | TRYA WKVLPQGFKNSPTLFEMQLAH (165-183) | |
| D FF IPL K | FAFT+ P | | TR+ WKVLPQGFKNSPT+F | |

| 184 | 202 | 219 | 225 | 259 | 279 |
|---|---|---|---|---|---|
| ILQYMDDILLASPSHEDLL | (203-218) | VSENKTQ | (226 | LPELQALLGEIQWV | -321) |
| I+ Y+ DDIL A + + L+ | | V ENKTQ | | L + Q LLG+I W+ | |
| I+QYMDDILLA+P | | | | | |

| 322 | 334 | 345 | 348 | 352 | 354 | 364 | 370 | 380 |
|---|---|---|---|---|---|---|---|---|
| RSRLVQTLPLLGA | IMLTLTGTTTV | | QSKEQ | | PLV-WLHAPLPHTSQ | | WGQLLASAVLL | |
| R RL | LPLLGA | | QSKEQ | | PLV W H PL H | | W QLL ++VLL | |
| | A +LT T TTTV | | | | APLP TSQ | | QLLA AVLL | |

| 397 | 404 | (406 | 414 | 426) | 432 | 472 | 482 | 487 | 499 |
|---|---|---|---|---|---|---|---|---|---|
| HHNISTQT | | NQFIQTSDH | | ELWNTFL | | FSDGSTS-RAAY | | KQILSQRSFPLPP | |
| HH+IS QT | | N+ IQ S+ H | | +LWNTFL | | F+DGS++ +AAY | | K IL+QRS+PLPP | |

| 500 | 509 | 514 | 533 | 538 | 557 | 562 | 569 | 587 |
|---|---|---|---|---|---|---|---|---|
| PHKSAQRAELLGLLHGL | | | YLYHYL | | ALLPRL | | YLHHVRS HTNLPDPISRLN | |
| P++ SAQRAELL LLH L | | | +LYHYL | | ALLPRL | | Y+ H+R+ HTNLP P+++ N | |

| 591 | 600 | 623 | 631 | 637 | 642 | 646 | 655 | 656 | 666 |
|---|---|---|---|---|---|---|---|---|---|
| DALLITPVLQ | | TTTEASNIL | | CRGGNP | | MPRGHIRRGL | | PNHIWQGDITH | |
| + ALLITPVLQ | | TTTE S IL | | CRGG+P | | M +G IRRGL | | PN +WQ D+TH | |

| 678 | 691 | 694 | (700 | 718) | (729 | 755) | 765 |
|---|---|---|---|---|---|---|---|
| HVWVDTFSGAISAT | | RKETSSEA | | INTDNGPAYISQ | | LVERSNGILKT | |
| VWV+TF | | RKETS++ | | NGPAYI | | VER+N LKT | |
| W DTFSG | | KETSSEA | | I TDNGPAY S | | | |
| | | KE+SSE+ | | +GPAYI | | | |
| | | | | PA+ISQ | | | |

| 783 | (819) | 835) | 852 |
|---|---|---|---|
| LSI ALWTINHLNVLTNCHKTRWQLHHSPRLQPI PETR | | GLNSRQWRGPQEALQEAA | |
| L++AL+ T+N V+TNCHKTRWQL HS LQPI PE | | GL+ SRQW G QEAL+EAA | |
| S+AL+ T+N V+TNCHK HS LQP | | QWRGP | |
| L +ALWT HK+RWQL HS PI ETR | | | |

| 867 | 873 |
|---|---|
| I PWRLLK | |
| WRLLK | |
| +PWRL | |

Fig. 15.

```
(1  56)  56           (66              132)*                    159 (159-170)
         ALSADQALQPP                   YWKFQQDVNFTQEVSH
         AL+ADQAL PP                   +W+ FQQ+V   T+ VSH
                                       VNFTQE 171              183       191 201         (210  241)             254        257
DPIWFLNTEPSQLPPTAPPLL      EPSIPWKSKL      YSPNVSVPSPSSTPLLYPSLA
DP WFLNTE S  L                S+PWKS L    YSPN S P SPSSTP
             QLP TAP LL                                     LL  PSLA
       EP++ LPPTAPPLL
            APPLLSH 305       312
TLGSRSRR
TLGSRSRR 258          272 (322             337 ) 377                              400
LPAPHLTLPFN  SALAMGAGVAGRITGS           QNRRGLDLLFWEQGGLCKALQEQCCF
L   PHL+LP   S+  A+G  G+A G I+  S       QNRRGLD+L      QGG+C AL  E+CCF
LP   P +T                               QNRRGLDLL      E+GGLC   L  E+CCF
                                        QNRR  LDLL     E+GG C    L  E+CC 415    420 425      (432    445)             460                       475
ERPPLE    T-GWGLNWD         TGITLVALLLLVILAGPCIGPCILRQLRHLPSRVR
+RPPLE    T GW LNW+         TG LV+LLLL +L GPC IG     RQLRHLP RVR
                            GI+L+ LLL V+L    C        L  +LRHL
                            GITLV+LLL
                               LVALLL+V+
                                L+ALLL++ ILA
                                TL+ALLL++ I

485
          PHYSLINPE
          YS +NPE
```

Fig. 16

Fig. 19A.
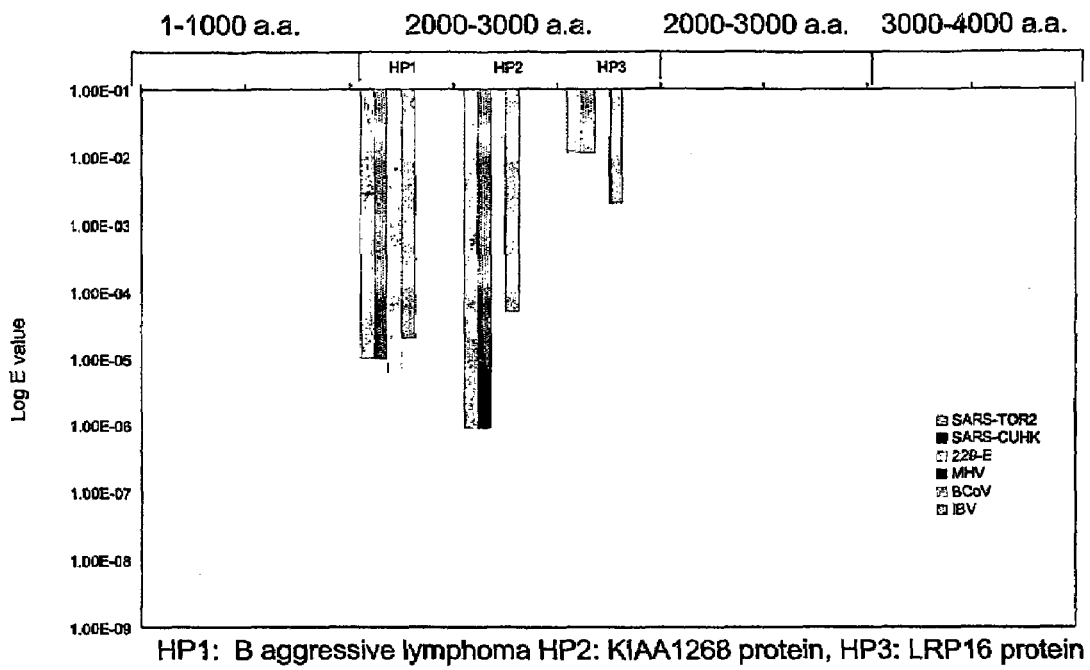
HP1: B aggressive lymphoma HP2: KIAA1268 protein, HP3: LRP16 protein
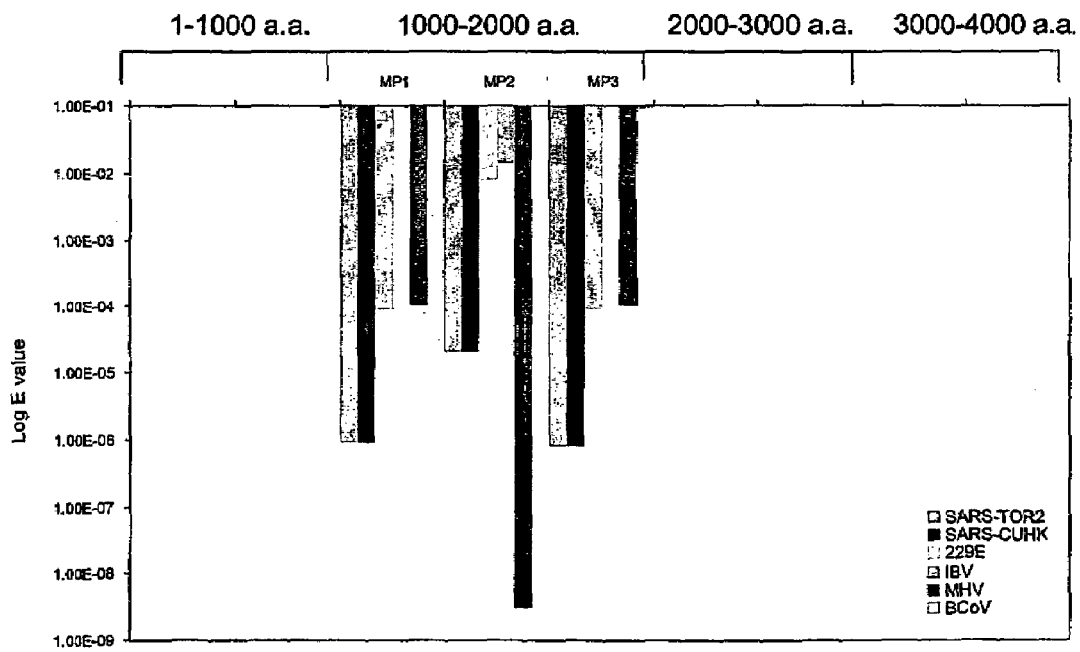
MP1: B aggressive lymphoma, MP2: BAC40943.1, MP3: BAC2987.1,
Fig. 19B.

ing International Application PCT/CA2004/000544, filed

DETECTION, CHARACTERIZATION AND TREATMENT OF VIRAL INFECTION AND METHODS THEREOF

CROSS-REFERENCE TO RELATED APPLICATIONS

This application is a continuation application of co-pending International Application PCT/CA2004/000544, filed Apr. 13, 2004, which designated the U.S. and which claims the benefit under 35 U.S.C. §119(e) of U.S. Provisional Application 60/461,137, filed Apr. 9, 2003 and U.S. Provisional Application 60/506,779, filed Sep. 30, 2003; the contents of which are herewith incorporated by reference in their entirety.

TECHNICAL FIELD

The present invention relates generally to methods for detecting and characterizing viral infection(s) in a host. Furthermore, the present invention relates to compositions and methods for treating viral infection(s).

BACKGROUND OF THE INVENTION

Viral infections have a debilitating effect on the economic output of society. Diagnosis is commonly difficult, and the availability of treatments limited. As a result, an infected individual must routinely battle the virus as it runs its course. In some instances, this battle is never won, as viral infections can become persistent. Hepatitis C virus (HCV) infection becomes chronic in up to 85% of infected individuals[1]. This is a serious worldwide public health concern, constituting a major cause of chronic hepatitis, cirrhosis, and hepatocellular carcinoma. The mechanisms for the high rate of viral persistence are unknown, and as a result, progress in the development of vaccine and antiviral therapies has been impeded. Viruses with RNA genomes such as HCV, can undergo mutation at high frequencies, and under appropriate selective pressure, rapidly generate viral variants. Distinctive among RNA viruses infecting humans, HCV is the only virus (with the exception of retroviruses) that persists in the majority of infected individuals. The hypervariable region 1 (HVR1), located in a stretch of 27-31 residues at the amino terminus of the second envelope glycoprotein (E2) has been identified as a main target of the anti-HCV neutralizing response, and is involved in the establishment of viral persistence[11,12]. However, the role of HVR1 in viral persistence has come into question in light of a recent study demonstrating that infection with modified HCV genomic RNA, without HVR1, although attenuated in growth, can cause persistent infection in chimpanzees, thus suggesting that HVR1 is not essential for HCV progression to chronicity[10].

Current commercial enzyme immunoassays (EIAs) for diagnosis of hepatitis C virus (HCV) infection, for example, have two major limitations: (i) their sensitivity is inadequate to detect seroconversion before 5-6 weeks post-infection leading to a prolonged window period (residual risk in blood supply is 1/100,000) (ii) their sensitivity is poor, causing an unacceptable false positive rate (40 to 50% in blood donors). Although nucleic acid testing will play an increasingly important role in narrowing the window period, it is technically complex and is not cost-effective.

The sensitivity of third generation EIAs for detection of anti-HCV antibodies has been improved by using a combination of viral proteins, as antigens, however, a prolonged window period to detection of seroconversion of HCV infection and a low specificity when testing the low risk populations such volunteer blood donors remains. Thus, improvements to current screening and detection methods for biological products is important for the safety of such products as well as for the cost-effectiveness of health care in general.

Although studies have investigated the diversity of persistent infection, a systematic characterization of viral persistence has not been previously developed. Accordingly, a need exists for a fundamental understanding of the mechanisms of viral infection and persistence as a basis to provide effective diagnosis and treatment regimes. Such an understanding would also provide a basis for the development of accurate and reliable detection systems for detecting viral infection.

Furthermore, current viral detection methods and/or systems are not capable of characterizing a viral infection, with respect to its capacity to persist in a host, for example. It would be beneficial to have indicators of viral behavior that are useful in characterizing a viral infection. The ability to characterize a viral infection would further serve to improve the determination of an effective treatment regime.

In this respect, there is a further need for the development of specific treatment regimes, tailored to target pre-characterized viral infections.

SUMMARY OF THE INVENTION

According to one aspect of the present invention, several sequence elements have been identified within viral genomes having a degree of similarity or homology with endogenous elements of a host capable of being infected with the virus of interest. For example, BLAST analyses of the HCV genome to Genbank resulted in the identification of several such sequence elements. As discussed further hereinbelow, the presence of such sequence elements, also referred to as viral-based sequence elements or host protein domain sequence elements (HPDSEs) having a degree of similarity or homology to an endogenous host element are identified as indicators of viral behavior in a host, in accordance with a preferred embodiment of the present invention. As a result, novel methods of detecting, characterizing and treating viral infection(s) are herein provided. In addition, the presence or absence of such HPDSEs or fragments thereof in compounds and/or preparations of the present invention, such as encoded viral-specific antigens, have application in the development of new anti-viral treatments and viral detection methods, such as EIAs, having improved sensitivity and specificity. These novel detection methods will be particularly useful in anti-viral antibody screening of biological products, such as blood, for example.

According to one aspect of the present invention a method of characterizing viral variants on the basis of a homology profile with a target host protein is provided. Characterization of a viral variant of HCV, for example, is based on the detection of a host protein domain sequence element(s) (HPDSEs) within a target region of a HCV genome. According to an aspect of the present invention, it has been determined that the degree of homology between a HPDSE within a target region of a virus and a protein of a host infected with the virus influences the levels of recognition by the immune system of the host and thus plays a major role in viral persistence. Furthermore, the present invention includes target-specific preparations useful in detecting and/or treating viral infection and methods of the same, based on the characterization of viral variants as herein provided.

According to a preferred embodiment of the present invention, the term "host protein domain sequence element" (HP- DSE) is intended to refer to a sequence element within a viral genome having a degree of homology to a host sequence. However, a HPDSE is not intended to be limited thereto. For example, a HPDSE of the present invention may more generally be any element within a viral domain having a degree of similarity or homology to an endogenous element of a host carrying the virus in question. Furthermore, an endogenous element of a host, also herein referred to as an "endogenous host element" may include an element naturally occurring within the domain of the host, such as a natural infectious or commensal organism of that host, for example, microbes on body surfaces and within organs (*E. coli*, *S. aureus*, *Ricketsia* sp, *Chlamydia* sp), as well as organisms resident within tissues (Circoviruses, *Salmonella* sp., viruses) as well as resident within genomes (Type A retroviruses). Preferably, a host element is a protein sequence or fragment thereof. For the purposes of the present invention, the term "host protein domain sequence element" may be used interchangeably with the term "viral-based sequence element".

A homology profile of the present invention preferably includes a sequence homology comparison of viral and host genomic structures. However, according to one embodiment of the present invention, a homology profile may be a comparison of structural homology of domains of viral and host molecular structure.

The term "antigenic determinant" as used herein refers to an element employed in accordance with the present invention to elicit an immune response in vivo.

The term "target sequence element" as used herein refers to a viral-based sequence element that is a target of a method of an embodiment of the present invention.

In accordance with an embodiment of the present invention, there is provided a method of characterizing a viral infection in a host, said method comprising: identifying at least one viral-based sequence element in a biological sample obtained from the host; determining a homology profile of said at least one viral-based sequence element with at least one endogenous host element; and characterizing said viral infection based on said homology profile; wherein said homology profile is indicative of a viral behavior of said viral infection in said host.

In accordance with another aspect of the present invention there is provided a method of diagnosing HCV infection in a patient. Based on a homology comparison of a target region of HCV having a HPDSE and a predetermined host protein, a characterization of viral behavior can be determined according to one aspect of the present invention. In this manner, a diagnosis and/or prognosis of a patient can be provided. According to yet another aspect of the present invention a method of diagnosing a HCV infection in a patient includes determining a sequence homology between a target region of a HCV variant and a variable region of human immunoglobulin. Preferably, the target region of a HCV variant is within an E2 protein thereof.

According to yet another aspect of the present invention, new anti-viral preparations and target compounds for HCV immunodetection, such as capture antigens for example, using HCV encoded proteins that are devoid of HPDSEs are provided.

In accordance with another embodiment of the present invention, there is provided a method of eliciting an immune response in a mammal, said method comprising introducing a composition comprising a purified antigenic determinant into said mammal in vivo; wherein said purified antigenic determinant includes a viral-based sequence element.

In accordance with another embodiment of the present invention, there is provided a recombinant viral protein comprising a sequence at least a portion of which has a predetermined degree of homology to an endogenous element of a host capable of being infected with a virus of interest.

In accordance with yet another embodiment of the present invention, there is provided a vector or nucleic acid construct that is (a) adaptable to infect or transfect a cell and (b) express a recombinant protein of the present invention.

In accordance with the still another embodiment of the present invention, there is provided an antibody that selectively binds to a sequence element within (i) an epitope of an S protein of SARS-CoV; (ii) an epitope of an E2 protein of SARS-CoV; (iii) an epitope of an ORF1a protein of said SARS-CoV; or (iv) an epitope of a Gag, Pol or Env polyprotein of HTLV-I.

In accordance with still another embodiment of the present invention, there is provided a viral-based sequence element having a predetermined degree of homology to an endogenous host element, wherein said endogenous host element is an element of a host having an, infection of a virus from which said sequence element derived; said sequence element being indicative of an outcome to viral infection.

In accordance with another embodiment of the present invention, there is also provided a purified polypeptide comprising a sequence element of the present invention, or a portion thereof.

In accordance with yet another embodiment of the present invention, there is still further provided a method of treating a viral infection in a host, said method comprising: identifying a viral-based sequence element in a biological sample obtained from said host having said viral infection; determining a sequence homology profile of said sequence element and an endogenous host element; and selecting a treatment regime based on said sequence homology profile; wherein said sequence homology profile is indicative of a disease state and/or predisposition for a disease outcome in said host.

In accordance with yet another embodiment of the present invention, there is still further provided a method of selecting target compounds for use in treating a viral infection, said method comprising: identifying compounds that bind to a target sequence element of a virus of interest; and selecting those compounds identified in (a) as candidate compounds for the treatment of an infection of said virus; wherein said target sequence elements have a degree of homology to an endogenous element of a host of interest capable of being infected with said viral infection.

In accordance with yet another embodiment of the present invention, there is still further provided a method of detecting a viral infection in a host, said method comprising: screening a biological sample obtained from said host for a target sequence element of an infecting virus; and detecting a viral infection when said target sequence element is identified; wherein said target sequence element is a viral-based sequence element having a predefined degree of homology to an endogenous element of said host; said homology being predictive of a disease state and/or predisposition for a viral outcome in said host.

In accordance with yet another embodiment of the present invention, there is still further provided a method of detecting a viral infection in a biological sample, said method comprising: a) treating said sample with a target compound having specificity for a domain of a viral protein; b) establishing suitable conditions for binding of said target compound to said viral protein; and c) detecting a complex of said target compound and said viral protein in samples infected with said viral infection; wherein said target compound has specificity for the viral protein while being absent of a target sequence element.

In accordance with yet another embodiment of the present invention, there is still further provided a target drug compound selected according to the method of the present invention.

In accordance with yet another embodiment of the present invention, there is still further provided a composition for treating a viral infection, said composition comprising: an antibody that selectively binds to an epitope of a virus of interest or variant thereof; and a pharmaceutically acceptable carrier; wherein said epitope of said virus includes a target sequence element having a degree of homology to an endogenous element of a host of interest.

In accordance with yet another embodiment of the present invention, there is still further provided a compound capable of binding an epitope of a virus for of interest for use in the manufacture of medicament for treating an infection caused by said virus, or related condition or disease wherein said epitope of said virus includes a target sequence element having a degree of homology to an endogenous element of a host capable of being infected with said virus.

In accordance with yet another embodiment of the present invention, there is still further provided a target compound having specificity for a domain of a viral protein; wherein said target compound is devoid of a sequence element of said viral protein, said sequence element having a degree of homology to an endogenous element of a host capable of being infected with a virus of interest.

In accordance with yet another embodiment of the present invention, there is still further provided an assay kit for detecting a viral infection; said kit comprising: a capture agent having specificity for an anti-viral antibody in a host; wherein a sequence element of at least one viral variant(s) is absent in said capture agent.

In accordance with yet another embodiment of the present invention, there is still further provided a method of eliciting an immune response to a virus of interest infecting a host, said method comprising: identifying a viral-based sequence element in a virus of interest; said sequence element having a degree of homology profile to an endogenous element of said host; preparing a purified-antigenic determinant that is devoid of at least a portion of viral-based sequence element; and introducing said antigenic determinant into said host in vivo.

In accordance with yet another embodiment of the present invention, there is still further provided a method of preparing a recombinant viral protein, said method comprising: identifying a viral-based sequence element in a virus of interest; said sequence element having a degree of homology to an endogenous element of a host capable of being infected with said virus; preparing a recombinant viral protein that is devoid of at least a portion of the viral-based sequence element; wherein said viral protein is adaptable for eliciting an immune response against said virus.

In accordance with yet another embodiment of the present invention, there is still further provided a recombinant viral protein prepared according a method of the present invention and a vector or nucleic acid construct containing the same.

Target-specific products and/or preparations of the present invention include but are not limited to antibodies specific to a target region of a virus of interest, antigenic response elements, polypeptides, recombinant proteins, genomic markers having complimentarily to a virus of interest, protein complexes, antagonists, vaccines and antiviral drugs. For both diagnostic and therapeutic purposes, target-specific products and/or preparations of the present invention may include viral protein sequences or fragments thereof. According to one aspect of the present invention, a target-specific product includes a HPDSE or a fragment thereof. Alternatively, a target-specific product of the present invention may include an altered HPDSE or a fragment of an altered HPDSE. According to a preferred embodiment of the present invention, target-specific products may be adapted to prevent induction of cross-reactive antibodies in a host. A diagnostic test and kit for detecting viral infection in a test sample is also provided. Preferably, target-specific products of the present invention will have utility in the treatment and/or diagnosis of HCV, Human Immunodeficiency Virus (HIV), HTLV-I, HTLV-II, SARS-CoV or a member of a Retroviridae, Flaviviridae, Herpesviridae, Papillomaviridae, Poxviridae or Coronaviridae family of viruses.

According to yet a further aspect of the invention, there is provided a target compound(s) and/or preparations having specificity for a HCV domain; wherein said target compound(s) and/or preparations are devoid of a target sequence element or HPDSE of said target HCV domain. Such a target compound(s) and/or preparation of the present invention have application in methods of detecting, characterizing and treating viral infection(s).

According to still a further aspect of the invention, there is provided a method of eliciting an immune response in a mammal, comprising introducing into the mammal a composition comprising a purified antigenic determinant; wherein said purified antigenic determinant includes a viral-based target sequence element.

According to still a further aspect of the invention, there is provided a recombinant HCV protein comprising a target sequence element wherein said target sequence element has a predetermined homology to a foreign protein.

According to still a further aspect of the invention, there is provided a purified polypeptide, the amino acid sequence of which comprises at least two residues of HVR1 of HCV. Preferably, a purified polypeptide of the present invention includes at least two amino acid residues from amino acids 1-27 of HVR1 of HCV. More preferably, a purified polypeptide of the present invention includes at least ten consecutive residues of HVR1 of HCV.

According to still a further aspect of the invention, there is provided a method of treating a viral infection, said method comprising: (a) identifying a viral-based target sequence element in a biological sample obtained from a mammal having a viral infection; (b) determining a sequence homology profile of said target sequence element and a host protein; and (c) selecting a treatment regime based on said sequence homology profile; wherein said sequence homology profile is indicative of a treatment response of said viral infection.

According to still a further aspect of the invention, there is provided a method of selecting drug target compounds for treating a viral infection, said method comprising: (a) identifying compounds that bind to a target sequence element of a virus of interest; and (b) selecting those compounds identified in (a) as drug target compounds for the treatment of an infection of said virus.

According to still a further aspect of the invention, there is provided a composition for treating HCV infection, said composition comprising: (a) an antibody that selectively binds to an epitope of HCV; and (b) a pharmaceutically acceptable carrier.

According to still a further aspect of the invention, there is provided a method of detecting a viral infection in a patient, said method comprising: (a) screening a biological sample obtained from said patient for a target sequence element of an infecting virus; and (b) detecting a viral infection when said target sequence element in said biological sample is identified; wherein said target sequence element is a viral-based sequence having a predefined homology to a host protein of said patient; said homology being predictive of a disease state and outcome of said viral infection.

According to still a further aspect of the invention, there is provided a method of determining a predisposition for a viral-induced autoimmune condition in a patient infected with a virus, said method comprising (a) screening a biological sample obtained from the patient for a target sequence element; and (b) determining a predisposition for a viral-induced autoimmune condition when the target sequence element is detected; wherein said target sequence element is a viral-based protein sequence having a predefined sequence homology to a host protein.

According to still a further aspect of the invention, there is provided a method of diagnosing a viral-induced autoimmune disease in a patient, said method comprising: (a) screening a biological sample obtained from the patient for a viral-based target sequence element and/or a target immunoglobulin; and (b) diagnosing an autoimmune disease when said target sequence element having a predefined homology to a host protein and/or a target immunoglobulin is identified.

According to still a further aspect of the invention, there is provided a method of characterizing an autoimmune condition in a patient, said method comprising: (a) identifying a viral-based target sequence element in a biological sample obtained from said patient; and (b) characterizing an autoimmune condition based on a sequence homology profile of said viral-based target sequence element with a host protein; wherein said sequence homology profile is indicative of the presence of or predisposition for an autoimmune condition.

According to still a further aspect of the invention, there is provided a compound capable of binding a target sequence element of a virus for use in the manufacture of medicament for treating a viral infection or related condition or disease.

According to still a further aspect of the invention, there is provided a method of determining a predisposition for lymphoproliferative disease in a patient infected with a virus, said method comprising: (a) screening a biological sample obtained from the patient for a target sequence element; and (b) determining a predisposition for lymphoproliferative disease when the target sequence element is detected; wherein said target sequence element is a viral-based protein sequence having a predefined sequence homology to a host protein.

According to still a further aspect of the invention, there is provided a method of detecting HCV infection in a biological sample, said method comprising: (a) treating said sample with a target compound having specificity for a domain of a HCV protein; (b) establishing suitable conditions for binding of said target compound to said HCV protein; and (c) detecting a complex of said target compound and said HCV protein in samples infected with HCV; wherein said target compound has specificity for a HCV protein while being absent of a target sequence element of said HCV protein.

According to still a further aspect of the invention, there is provided a target compound having specificity for a domain of a HCV protein; wherein said target compound is devoid of a target sequence element of said HCV protein domain.

According to still a further aspect of the invention, there is provided an anti-viral treatment cocktail for treating a HCV infected mammal, said treatment cocktail comprising an immunogenic compound capable of eliciting a HCV-specific immune response and an anti-viral compound.

According to still a further aspect of the invention, there is provided a method of treating HCV infection in a mammal, said method comprising: (a) detecting at least one target sequence element of a HCV virus infecting said mammal; and (b) administering a HCV-treatment cocktail to said mammal corresponding to the detection of said at least one target sequence element; wherein steps (a) and (b) are repeated throughout a course of treatment and the contents of said treatment cocktail are tailored according to a level of detection of said target sequence element(s).

According to a preferred aspect of the present invention, a level of detection of a target sequence element(s) is preferably a degree of sequence homology to a host protein. According to, yet a further preferred aspect of the present invention, when a target sequence element is a sequence element of an E2 protein of HCV having at least approximately 30% homology to a host immunoglobulin, a treatment cocktail preferably includes at least interferon. According to still a further preferred aspect of the present invention, when said target sequence element is a sequence element of an E2 protein of HCV having less than approximately 40% homology to a host immunoglobulin, said treatment cocktail preferably includes at least an immunogenic compound.

According to still a further aspect of the invention, there is provided an assay for detecting a HCV viral infection; said assay comprising: a capture agent having specificity for an anti-HCV antibody in a host; wherein a target sequence element of one or more HCV viral variant(s) is absent in said capture agent.

According to a further aspect of the invention, there is provided a purified polypeptide, the amino acid sequence of which comprises a target sequence element having at least 20% homology to a human immunoglobulin.

Furthermore, the present invention has application in the development of treatment regimes to target genotype-specific viral variants. According to this aspect of the present invention, economically- and pharmacologically-efficient treatment regimes for viral infections are provided. According to a strategy of characterizing viral variants as herein provided, a targeted and specific treatment regime can be prescribed to combat a predetermined viral variant, at the onset of detection. Thus, replacing conventional trial and error treatment programs, and improving the time course to recovery.

According to a further aspect of the invention, there is provided an antibody that selectively binds to a target sequence element within an epitope of a second envelope (E2) glycoprotein of HCV. Upon characterizing a viral variant, according to methods as herein provided, a targeted treatment regime can be prescribed which may include the use of variant-specific compounds as discussed further hereinbelow, to target the viral variant identified. In doing so, the variants propensity to employ molecular mimicry as a strategy for immune invasion will be considered.

According to a further aspect of the invention, there is provided a recombinant HCV protein comprising a target sequence element wherein said target sequence element has a predetermined homology to a foreign protein.

The present invention also provides A method of selecting drug target compounds for treating a viral infection, said method comprising: identifying compounds that bind to a target sequence element of a virus of interest; and selecting those compounds identified:in (a) as drug target compounds for the treatment of an infection of said virus. The virus of interest is preferably HCV and said target sequence element is a sequence element of an E2 HCV protein. The sequence element preferably includes two or more amino acids of amino acids 1-27 of HVR1 of E2 in HCV. Also provided is a a target drug compound selected according to the method of present invention.

The present invention also provides a method of detecting a viral infection in a patient, said method comprising: screening a biological sample obtained from said patient for a target sequence element of an infecting virus; and detecting a viral infection when said target sequence element in said biological sample is identified; wherein said target sequence element is a viral-based sequence having a predefined homology to a host protein of said patient; said homology being predictive of a disease state and outcome of said viral infection. In a preferred embodiment, said viral infection is HCV and said target sequence element is a sequence element of an E2 HCV protein. In another preferred embodiment, said sequence element includes two or more amino acids of amino acids 1-27 of HVR1 of E2 in HCV. Additionally, said host protein is preferably an immunoglobulin. In a preferred embodiment, said step of screening includes the use of a compound having specificity to said target sequence element and includes a detectable label.

The present invention also provides a method of characterizing an autoimmune condition in a patient, said method comprising: identifying a viral-based target sequence element in a biological sample obtained from said patient; and characterizing an autoimmune condition based on a sequence homology profile of said viral-based target sequence element with a host protein; wherein said sequence homology profile is indicative of the presence of or predisposition for an autoimmune condition. In a preferred embodiment said viral-based target sequence element is a HCV target sequence element. In another preferred embodiment, said HCV target sequence element is a sequence element of an E2 HCV protein. The host protein is preferably an immunoglobulin. In another preferred embodiment, said immunoglobulin is selected from the group consisting of immunoglobulin class G, A, M, D or E. The autoimmune condition is preferably selected from the group consisting of mixed Type II cryoglobulinemia, membranoproliferative glomerulonephritis, and porphyria cutinea tarda.

The present invention also provides a compound capable of binding a target sequence element of a virus for use in the manufacture of medicament for treating a viral infection or related condition or disease. In a preferred embodiment, said related condition or disease is one of a persistent viral infection; an auto-immune condition or a lymphoproliferative disease. There is also provided the use of the compound wherein said virus is a HCV, Human Immunodeficiency Virus (HIV) or a member of a Retroviridae, Flaviviridae, Herpesviridae, Papillomaviridae or Coronaviridae family of viruses.

The present invention also provides a method of determining a predisposition for lymphoproliferative disease in a patient infected with a virus, said method comprising: screening a biological sample obtained from the patient for a target sequence element; and determining a predisposition for lymphoproliferative disease when the target sequence element is detected; wherein said target sequence element is a viral-based protein sequence having a predefined sequence homology to a host protein. In a preferred embodiment, the method further comprises screening said biological sample for an immunoglobulin. In another preferred embodiment, said immunoglobulin is a cross-reactive immunoglobulin having specificity for a target sequence element of said virus. The virus is preferably, HCV and said target sequence element is a sequence of a E2 HCV protein. In accordance with the present embodiment, said patient has an autoimmune condition; wherein said autoimmune condition is mixed (Type II) cryogobulinemia.

The present invention also provides a target compound having specificity for a domain of a HCV protein; wherein said target sequence compound is devoid of a target sequence element of said HCV protein domain. Preferably, said target sequence element has a predefined homology to a foreign protein. Additionally, said target sequence element includes a sequence element of an E2 protein of HCV. Said sequence element includes two or more amino acids of amino acids 1-27 of HVR1 of HCV. In a preferred embodiment, said sequence element includes amino acids within positions 384 to 514 of an E2 HCV protein; said sequence element having at least 20% sequence homology to a foreign immunoglobulin. More preferably, said target sequence element is at least 20% homologous to a foreign immunoglobulin. Said foreign protein is preferably a human protein. Moreover, said foreign immunoglobulin is a human immunoglobulin. The target compound of the present invention may be used for detecting the presence of a HCV virus in a biological sample. More preferably, for use in the manufacture of a medicament for treating HCV.

BRIEF DESCRIPTION OF THE DRAWINGS

Further features and advantages of the present invention will become apparent from the following detailed description, taken in combination with the appended drawings, in which:

FIGS. 1a-1e illustrate features of IgVL major homologous domains (MHDs) in E2. Features of IgVL major homologous domains (MHDs) in E2. Amino acid sequence alignment of HCV E2 (1-130aa) and the IgVL domain of antibodies (1-120 aa). a. Alignment of E2 sequences from HCV genotype 1a (SEQ ID NO: 76) (sample S1 described in text) and 2a (SEQ ID NO: 79) with IgVL sequences of antibodies that posess maximal homology (2ig2L, V-J and fvdA disclosed as SEQ ID NOS 77-78 and 80, respectively). Identical aa are indicated with colons and similar amino acids are marked with a dot in the alignment. Spaces have been inserted in the sequence as dashes (—). b. Demonstration of sequence homology between E2 and IgVL of human and mose antibodies. Amino acid aligment of the E2 sequences from nine different genotypes of hepatitis C virus randomly seleted from GenBank, and 11 IgVL sequences that include representatives of the 4 IgVLκ subgoups (CAR, TEW, CLL and B17) 'of antibodies[20], germline antibody and functional human V-J region (V-J) and 4 mouse antibodies. Figure discloses SEQ ID NOS 81-101, 100, 102-109, 104, 110-111, 104, 112-116, 114, 117-118, 114, 119-123 and 114, respectively, in order of appearance. Identical amino acids found in both antibodies and HCV E2 sequences are indicated in bold; conservation of common amino acids is indicated for levels $\geq 50\%$ and 25-50% that are indicated by a colon (:) and a dot (.) repectivley. The levls are caculated using the methods decribed[11]. Sequence gaps are indicated with a blank spaces. Omitted sequences are indicated with breaklines. c. Sequence alignment of the consensus sequences of FR1 of IgVL and HVR1 of various genotypes of HCV. The frequency of appearance of amino acids at each position in 500 immunoglobulins and 1382 HVR1 sequences was analyzed and aligned. The 3-5 most frequently appeared amino acids in IgVL of human and mouse antibodies are shown for each postion. Amino acids of HVR1 and IgVL sequences are listed in decreasing order of defined frequency, from top to bottom. The frequency of appearance of the bottom residues listed is more than 5% for HVR1 and 10% for IgVL in the sequences observed. Identical amino acids in each residue position in IgVLs and HVR1s are indicated by bold single letter. d. Amino acid sequence alignment of IgVL FR1 regions (SEQ ID NOS 124-131, respectively, in order of appearance), showing the range of homology between IgVLκ subgroup 1, other subgoups 2, 3 and 4, and IgVLκ of germline and fuctional antibodies. e. E2/IgVL major homology domains are located on the three dimensional structure of the V-J antibody molecule drawed using Millennium STING (http://mirrors.rcsb.org/cgi-bin/SMS/STINGm/start), showing the locations of the motifs LTS and SPG in MHD1, and MHDs 2 and 3 of HCV E2 on the antibody molecule.

FIG. 2 illustrates amino acid sequence alignments of HCV sub-populations and IgVL antibodies. (SEQ ID NOS 132, 82, 133-134, 84, 135, 86, 136-137, 88, 138, 90, 139, 92, 140 and 94, respectively, in order of appearance). Amino acid sequence alignment of HCV sub-populations and IgVL of antibodies, showing the mutations relative to the source virus sequence (S1) and changes of sequence homology to IgVL in the E2 region (10-110 aa) of the cloned variants during the early phase of HCV primary infection in a patient[23]. a. Sequence alignment of E2 clones from sequential samples from the patient collected before (A1 and A2) and following seroconverison and the establishment of persistent infection (A3) relative to the sample from the source patient with persistent HCV infection (S1). The number of clones obtained with a given sequence are indicated by numbers for each sequence. Amino acid identity between E2 and antibodies are indicated by bold letters. Homologous sequences among the clones are indicated by dashs. The marker (:) denotes amino acid identity in the majority (>85%) of clones to the corresponding residue in the antibodies. Dots (.) indicates that the identical amino acid exits in a lower propotion (<85%) of clones as seen in A1 (68%) and A2 (84%). A region of identical sequence was not shown and is indicated by breaks (//). Sequence gaps are indicated by blank space. b. Sequence alignment of HVR1 (11-27) in the major populations found in persistant and non-persistant clones with respect to homology of FR1 (1-20 aa) of antibodies shown in bold. (SEQ ID NOS 141-143, 142, 144, 142, 145, 142, 146, 142, 147, 142, 148, 142, 149, 142, 150, 142, 151, 142, 152, 142, 153 and 142, respectively, in order of appearance). Persistent infection was associated with a loss of viruses possessing sequences with low homology concomitant with selection of virus with the highest homology.

FIGS. 3a-3d illustrate sequence alignment of FR1s of antibodies and HVR1s of HCV isolates from patients with primary infection and immuno-compromised patients with chronic HCV infection. Sequence alignment of FR1s of antibodies and HVR1s of HCV isolates from patients with primary infection and immunocompromised patients with chronic HCV infection. a. N-terminal consensus sequence of FR1s of antibodies; b. HVR1 sequences of the variants from the patient infected with genotype 1a[23]. (SEQ ID NOS 154-161, 158, 162-165, 156 and 155, respectively, in order of appearance). c. HVR1 sequences of the variants from a patient infected with genotype 2c[26]. (SEQ ID NOS 166-167, 166, 166, 168-176, respectively, in order of appearance). d. HVR1 sequences of the isolates from immunocompromised patients[34]. (SEQ ID NOS 177-180, 180, 180-181, 181, 181-184, 184-187, respectively, in order of appearance). Patient 1 and 2 had agammaglobulinemia. Patients 3-5 had AIDS. These patients were followed longitudinally with regard to changes in HVR1 using direct DNA sequencing for a period of time (0-63 weeks). Patient 6 had immunosuppressive therapy following bone marrow transplantation[35]. The samples were taken before (time 0) three and 12 months after bone marrow transplantation. The HVR1 sequences represent the consensus sequences of 8 randomly selected clones from each sample.

FIGS. 4a-4c illustrate sequence alignments of FR1 regions of antibodies with mutated sequences of HCV HVR1 in chimpanzees. Sequence alignment of FR1 regions of antibodies with mutated sequences of HCV HVR1 in chimpanzees. (a) IgVL FR1 consensus sequence of human antibodies. Amino acids that are homologous with HCV HVR1 sequences are indicated in bold. (b), The sequence changes of viral populations from chronically infected chimpanzees over time relative to the infecting virus for animals, Peggy and Hans[24]. (SEQ ID NOS 188, 188, 188, 188, 188-190, 190, 190-192, 188, 188, 193-195, respectively, in order of appearance). c. Evolution of HVR1 sequence during chronic infection of chimpanzee #1[35]. (SEQ ID NOS 196-198, 198, 198-199, 199-202, 202 and 202, respectively, in order of appearance).

FIGS. 5a-5d illustrate the correlation of changes in homology of IgVL FR1s of antibodies and B-cell epitopes with variant immune escape. The correlation of the changes in homology of IgVL FR1s of antibodies and B-cell epitopes with variant immune escape. (a). IgVL FR1 consensus sequences (4-17 aa) of antibodies. (b). The sequences of epitopes 1 and 2 in HVR1 of isolate from patient I[23]. (SEQ ID NOS 203-210, respectively, in order of appearance). Antibody reactivity to the peptide was positive at 6, 8, 11 and 14 months p.d. (++++), at 8, 11 and 14 (+++), and at 8 and 11 or 14 (++) months p.d. Antibody reactivity was negative at all time points 2, 6, 8, 11, and 14 (–). (c and d). The sequences of epitopes 1 and 2 of quasispecies clones from patients infected with HCV genotype 1a (c) (SEQ ID NOS 211-214, respectively, in order of appearance) and 2c (d) (SEQ ID NOS 215-220, respectively, in order of appearance) respectively [23,26].

FIGS. 6a-6c illustrate sequence alignments of HCV variants (A1-A5) with IgVLκ in the course of primary infection. Genetic evolution and selection of variants in the course of HCV primary infection. A. Alignment of representative IgVLκ(SEQ ID NOS 132, 221, 135, 222-224 and 140, respectively, in order of appearance); B. Consensus sequence of IgVLκ; C. Sequence of clones of HCV present in an infected patient. (Residues 1-28 and 33-72 of SEQ ID NOS 1-54, Residues 1-27 and 32-71 of SEQ ID NO: 55, Residues 1-28 and 33-72 of SEQ ID NOS 56-63, respectively, in order of appearance). Samples had been obtained at various times before and after seroconversion and IFN treatment. A1: Before seroconversion; A2, early seroconversion; A3, four weeks after seroconversion; A4, four weeks after IFN treatment; A5, nine weeks after IFN treatment. S-Dir is the consensus sequence of the source virus from the source patient.

FIG. 7 illustrates sequence alignments of HCV NS5A clones and corresponding response to IFN treatment (SEQ ID NOS 225, 64, 64, 64, 64, 64, 64, 64, 64-65, 65, 65, 65, 65, 65-66, 66, 66, 66, 66-67, 66, 66, 68-69, 68, 68, 68-69, 68 and 68, respectively, in order of appearance). Alignment of amino acid sequences[a] of independent HCV NS5A clones from four patients, showing characteristic of a quasispecies distribution in the ISDR. [a]—The alignment of amino acid sequences was deduced from the nucleotide sequences (On-line Protein Translation using MBS Web site) of 30 independent clones obtained before IFN treatment in four patients. [b]—Week 0 corresponds to viral load before IFN treatment; week 1 and 8 correspond to viral load 1 and 8 weeks the after first administration of IFN therapy.

FIG. 8 illustrates NS5a sequence alignments to immunoglobulin (IgG2A) (SEQ ID NO: 230) for HCV clones. Pre-treatment samples (samples 03, (SEQ ID NO: 229) 56(SEQ ID NO: 227), and 65(SEQ ID NO: 226) from HCV-1b infected patients) and WT-1b(SEQ ID NO: 228) sequences show homology to immunoglobulin. Sample 03, the most IFN resistant isolate, shows 43.45% homology to immunoglobulin IgG2A (PDB Acc# ligtA). Samples 56 and 65 and WT-1b sequences show lower degree of homology.

FIG. 10 illustrates an alignment of immunoglobulin Light Chain genes of HCV associated WA monoclonal rheumatoid factors and lymphomas. (SEQ ID NOS 231-237, 232, 238-240, 232, 241-245, 232 and 246-247, respectively, in order of appearance). Alignment of Light chain genes of HCV associated WA monoclonal rheumatoid factors and Lymphomas. The Ly2 antibody is secreted by a lymphoma, is very similar in sequence to WA1 antibody and binds E2 suggesting that this immunoglobulin was induced in response to HCV infection and that WA producing B-cells are progenitors of lymphomas. The accession numbers are the source of the variable region of immunoglobulin light chain genes.

FIG. 12 illustrates a comparison of host protein domains sequence elements (HPDSEs) found in gag protein of HTLV-I and HIV, with human proteins, using NCBI-protein Blast program, according to one embodiment of the present invention. Comparing identical human protein domains and sequence elements (HPDSEs) found in gag protein of HTLV-I and HIV using NCBI-protein Blast program.

FIG. 13 illustrates HPDSEs within gag protein of HTLV-I according to an embodiment of the present invention (SEQ ID NOS 252-261, respectively, in order of appearance). Host Protein Domain Sequence Elements (HPDSEs) in gag protein of HTLV-I, shown in black with corresponding endogenous host gene sequences shown in color (with host gene accession numbers shown in Table 5a). *The predicted non-cross reactive sequences (aa) in HTLV-1 gag protein for designing antigens are shown in brackets: 21-34, 39-89, 133-149, 172-210, 245-310, 331-347 and 371-382.

FIG. 14 illustrates HPDSEs within Poly protein of pol in HTLV-I according to an embodiment of the present invention (SEQ ID NOS 262-296, respectively, in order of appearance). Host Protein Domain Sequence Elements (HPDSEs) in Polyprotein of pol in HTLV-I, shown in black with corresponding endogenous host gene sequences shown in color (with host gene accession numbers shown in Table 5b). *The predicted non-cross reactive sequences (aa) in HTLV-1 pol protein for designing antigens are shown in brackets: 1-35, 84-110, 163-183, 203-218, 226-321, 406-426, 700-718, 729-755 and 819-835.

FIG. 15 illustrates HPDSEs within env protein of HTLV-I according to an embodiment of the present invention (SEQ ID NOS 297-309, respectively, in order of appearance). HPDSEs in env protein of HTLV-I, shown in black with corresponding endogenous host gene sequences shown in color (with host gene accession numbers shown in Table 5c). *The predicted non-cross reactive sequences (aa) in HTLV-1 env protein for designing antigens are shown in brackets: 1-56, 66-132, 159-170, 210-241, 322-337 and 432-445.

FIG. 16 illustrates an alignment of Peyer's Patches virulent factor of different Bacteria and Transposes elements with amino acids in E2 protein of different Sars-CoVs according to an embodiment of the present invention. (SEQ ID NOS 310-320, 320,320, 320 and 320-321, respectively, in order of appearance). Alignment of Peyer's patches virulent factor of different Bacteria and Transposes elements with amino acids in E2 protein of different Sars-CoVs. *The dark color shows the similarity to Peyer's patch virulent factor. **The one dot shows the similar property and Two. Dots show the Identity between amino acids of SARS-CoVs and majority of amino acids in Peyer's Patch protein or transposes in different bacteria.

FIGS. 19A & 19B illustrate HPDSEs identified in ORF1a replicase of SARS-CoV having significant protein homology with human (A) and mice (B) proteins (as identified in Table 8), shown as E values, according to an embodiment of the present invention. Significant protein homology found in ORF1a replicase of SARS-CoV in humans (panel A) and mice (panel B), shown as E values (corresponding host proteins identified in Table 8). Significant human protein homology found in ORF1a replicase of SARS-CoV and other coronaviruses. Significant mouse protein homology found in ORF1a of replicase of SARS-CoV and other coronaviruses.

FIG. 20A. Alignment of human and mouse (MP1 (SEQ ID NO: 327), MP2 (SEQ ID NO: 328)) proteins with homologous regions from ORF1a from SARS-CoV (SARS-Tor2 disclosed as SEQ ID NO: 325) and coronaviruses representing the 3 known antigenic groups (HCoV-229E (SEQ ID NO: 326), MHV (SEQ ID NO: 329), and IBV (SEQ ID NO: 330)) are shown in the top panel where sequence identity with the human proteins (HP1 (SEQ ID NO: 323), HP2 (SEQ ID NO: 324)) is masked in yellow. FIG. 20B. Pair wise sequence comparisons of proteins of FIG. 20A are shown, the correspondence of sequences with row and column numbers is shown at the right.

DETAILED DESCRIPTION OF THE PREFERRED EMBODIMENT

Figure 9:
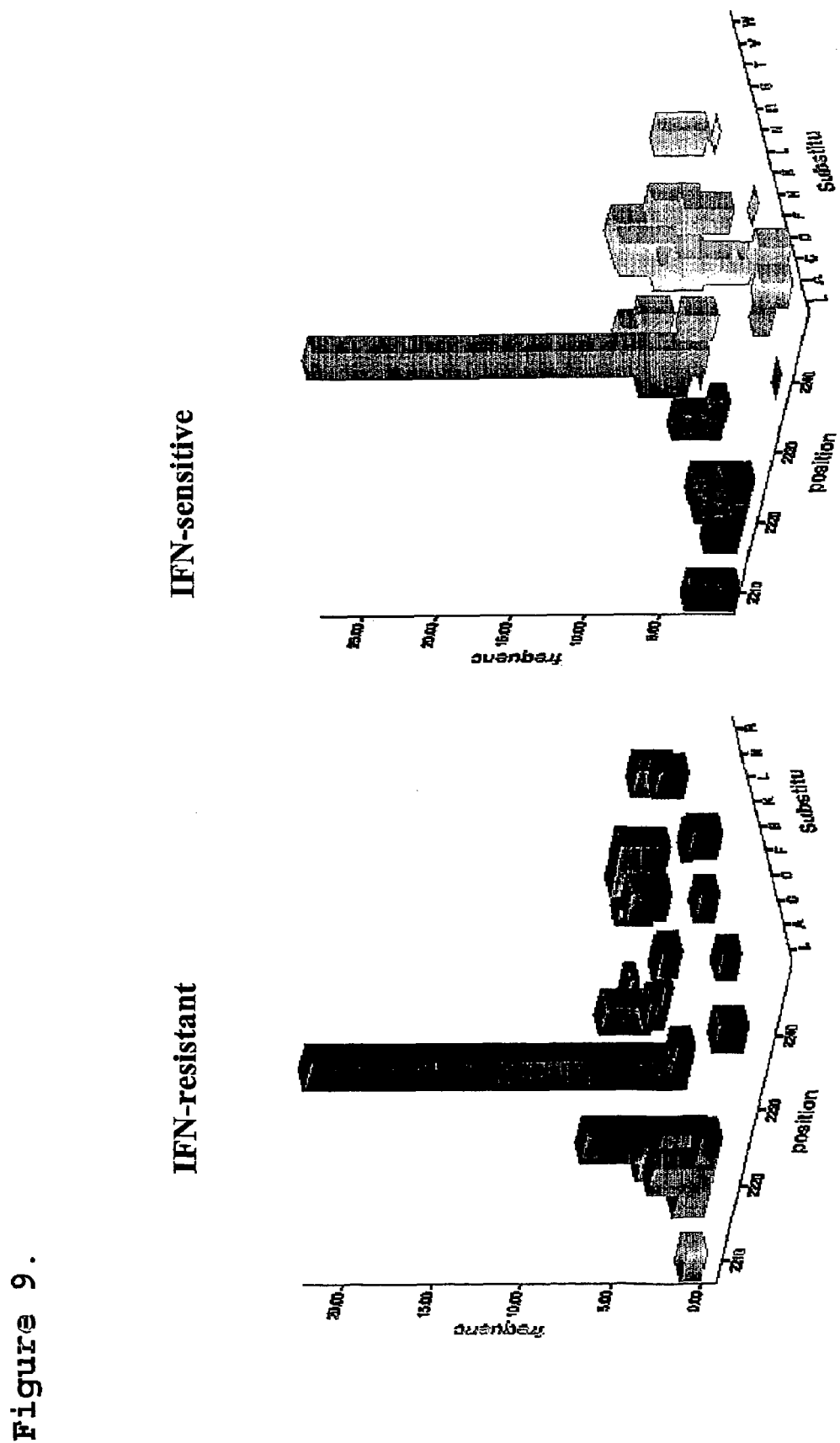
FIG. 9 illustrates a comparative representation of substitutions in IFN-resistant and IFN-sensitive ISDRs following interferon treatment. Comparison of substitutions in IFN-resistant and IFN-sensitive ISDRs among intermediate type. Three dimensional plot of the position (x-axis), amino acid substitution (y-axis), and frequency (z-axis) of substitutions in IFN-resistant and IFN-sensitive ISDRs. The results demonstrate that IFN-sensitive ISDRs contain a higher frequency and larger variety of substitutions than IFN-resistant ISDRs.

According to the present invention, a strategy for immune evasion by viral pathogens has been characterized. In particular, molecular mimicry has been identified as a viral strategy for immune evasion. Based on this strategy, mutations within a viral domain are shown to establish an increased similarity and/or homology with an endogenous host element during the course of infection. According to the present invention, this homology is correlated to a viral characterization, and more preferably to a viral outcome. For example, a persistent viral infection may be characterized in accordance with an embodiment of the present invention on the basis of a pre-defined homology profile of the virus causing the infection.

In accordance with one embodiment of the present invention, a comparative analysis of the HCV genome with human sequences in Genbank was conducted. This analysis identified the presence of many host protein domains sequence elements (HPDSEs) within several regions of HCV gene encoded proteins. The presence of such HPDSEs were found to exist in viral variants that persisted in an infected host.

According to the strategy of molecular mimicry as characterized in accordance with the present invention, a comparative analysis is conducted, as exemplified hereinabove, to identify the presence of, or predisposition for HPDSEs in a viral genome. The identification of a HPDSE involves the detection of a significant degree of homology in a region of the genome of an infectious pathogen with that of an endogenous host element, such as a protein, for example. In accordance with the present invention, "significant homology" is intended to mean a degree of homology having predictive biological properties. More specifically, a degree of homology of a given HPDSE is significant when the extent (quantitative measure) or nature (qualitative measure) of the homology is predictive of a biological property of a virus or infectious agent. Preferably, significance is defined empirically as a homology that is greater than chance, i.e. significantly greater than 5% which is the random probability of occurrence of one of 20 amino acids at the same sequence position in any 2 proteins. More preferably, significant homology includes the range of similarities of greater than or equal to 20% but can include other homologies that are less than 20% but greater than 5%.

According to the present invention, qualitative homology may include viral and host structures having a same or similar molecular shape and are composed of non-homologous amino acid sequences. This is in accordance with the well known phenomenon of complementary shape that defines antibody binding of different antibodies to epitopes, which occur independent of amino acid sequence homology. Accordingly, it is intended that a homology profile of the present invention can refer to a structural homology within the molecular constitution of a viral variant as compared with a host protein. Furthermore, a structural homology may include a homology of antigenic structures having a same or similar molecular shape but a different genomic constitution. Alternatively, as mentioned herein above, a homology profile of the present invention may be based on a sequence homology wherein a degree of homologous sequences are identified within a viral HPDSE relative to a corresponding host protein domain(s).

Since a viral pathogen has the ability to mutate during the course of infection, a predisposition for the development of a HPDSE may be found where an analysis is conducted at an early stage of infection in an host, and a comparative analysis identifies a pattern of similarity that may be indicative of a predisposition to evolve or mutate to become more homologous to an endogenous host element over time.

It is contemplated that suitable test systems, as generally known in the art, can be employed to establish whether or not a target HPDSE has the ability or predisposition for immune evasion in a host. One such indicator of immune evasion may be a lack of immune recognition in a suitable test system when a HPDSE is prepared in a suitable fashion for use in immunization. Conversely, the ability of antibodies to HPDSE or the corresponding host domain (usually though not exclusively those produced in another species of host) to cross-react, which is seen as reaction of said antibodies with both structures, may be another such indicator.

The present invention further provides for the use of viral-based sequence elements that optionally induce cross-reactive antibodies in a host. In the case of gipA, discussed further hereinbelow, it may be desirable to be provided with such cross-reactive antibodies. In this case, such antibodies may inhibit bacterial infection and thus serve useful in the treatment of infection.

The present invention is herein exemplified in accordance with HCV, HTLV-I/II and SARS-CoV, however it is fully contemplated that the scope of the present invention extends to include other viral pathogens, including, but not limited to Human Immunodeficiency Virus (HIV), and members of the Retroviridae, Flaviviridiae, Herpesviridae, Papillomaviridae, Poxviridae and Coronaviridae families of viruses.

According to an embodiment of the present invention, novel treatment regimes are provided based on a viral variant characterization as herein described. Such treatment regimes are preferably tailored to target specific viral variants based on their pre-determined genotypic characteristics, such as the presence of HPDSEs within their genome. For example, pre-determined genotypic characteristics of a viral variant may be indicative of a variant having the potential to persist in a host. Upon characterization in this regard, according to the present invention, a targeted treatment regime can be prescribed to more effectively combat the particular viral variant.

In accordance with the present invention, one such treatment regime, is provided to elicit an antibody response to a virus in vivo. Preferably, the treatment methods and/or preparations of the present invention serve to elicit a immune response that prevents binding of host protein domain sequence elements (HPDSEs) by antibodies and/or T cells, for example. Specifically, an antigenic determinant of a virus displaying characteristics of molecular mimicry in a host is provided in accordance with the present invention. According to a preferred embodiment, a target sequence element is absent from an antigenic determinant of a virus. For example, a host protein domain sequence element identified as a target sequence with respect to immune recognition, such as IgVL-like protein domain or an IgG-like protein domain, in the case of HCV for example, may be effectively removed of inactivated in an antigenic determinant of the present invention. An antigenic determinant of the present invention may include a polypeptide or recombinant protein. Furthermore, antigenic determinants of the present invention may be utilized to detect the presence of anti-viral antibodies in test samples. For example, a test sample is incubated with a solid phase to which at least one recombinant protein has been attached. These are reacted for a time and under conditions sufficient to form antigen/antibody complexes. Following incubation, the antigen/antibody complex is detected. Indicator reagents may be used to facilitate detection, depending on the assay system chosen.

Compositions of the present invention, including antigenic determinants, such as a recombinant protein, for example can be prepared according to general methods known in the art, such as those exemplified in the teachings of Sambrook et al. 1989. Molecular Cloning—A Laboratory Manual, Cold Spring Harbor Laboratories which is herein incorporated by reference.

A unique feature of the present invention is the ability to derive medicaments for treating a viral infection that inactivate a predetermined HPDSE of a viral variant, but do not interact in a deleterious or undesirable way, with respect to efficacy or safety, with a corresponding host protein domain. A rational assessment of adverse drug reactions with known host structures such as host protein domains is provided in accordance with an embodiment of the present. This practice avoids the explorative process normally needed to detect and modify adverse reactive effects of candidate medicaments.

Antiviral treatments and diagnostic methods of the present invention may include polyclonal or monoclonal antibodies that bind antigenic response elements or that target domains of a virus of interest. For example, according to a preferred embodiment of the present invention, anti-idiotypic antibodies to IgLVκ variable region are provided to neutralize HCV. An antiviral treatment cocktail is provided comprising an antibody or target compound specific to HCV, in combination with interferon, for example. In this case, an antibody specific to HCV would serve to bind to HCV and block viral synthesis while interferon would serve to block viral replication in infected cells. More preferably, monoclonal antibodies to IgLVκ are prepared in vitro and are capable of neutralizing HCV without eliciting autoimmunity in a recipient. Other anti-viral treatment cocktails may be provided in accordance with the present invention.

According to a preferred embodiment of the present invention, a protein complex comprising an E2 sequence plus another antigenic component that augments antigenicity is applied to induce an anti-HCV immune response. Such a protein complex may be administered alone or in combination with other HCV treatment regimes. Preferably, an antiviral treatment with a protein complex as described may be followed by the application of neutralizing monoclonal antibodies. According to yet a further embodiment of the present invention, viral vaccines may be provided in accordance with the present invention. A vaccine of the present invention will preferably induce neutralization without cross-reaction with immunoglobulin or other host proteins.

It is within the scope of the invention that antibodies, both monoclonal and polyclonal, can be generated using recombinant proteins or polypeptides of the invention as antigens. The monoclonal antibodies can be provided individually to detect viral antigens. Combinations of monoclonal antibodies (and fragments thereof) of the present invention may also be used together as components in a mixture or "cocktail" of at least one anti-viral antibody of the invention with other HCV regions, each having different binding specificities. For example, such a cocktail can include monoclonal antibodies which are directed to HCV envelope proteins and other monoclonal antibodies to other antigenic determinants of the HCV genome, for example. Methods of making monoclonal or polyclonal antibodies are well-known in the art. See, for example, Kohler and Milstein, Nature 256:494 (1975); J. G.

R. Hurrell, ed., Monoclonal Hybridoma Antibodies: Techniques and Applications, CRC Press, Inc., Boco Raton, Fla. (1982); and L. T. Mimms et al., Virology 176:604-619 (1990), which are incorporated herein by reference.

Furthermore, a panel of monoclonal antibodies will be produced according to methods well known in the art, and as exemplified in the teachings of Sambrook et al. that react with and thus identify the extent of homology of a viral variant to a host protein. Treatment modalities will thus be applied according to their efficacy with respect to the extent of antigenic mimicry of a target viral protein domain.

Vaccines for treatment of viral infection are encompassed by the present invention. For example, an HCV vaccine may comprise an immunogenic peptide obtained from a mammalian expression system containing envelope and non-envelope genes or fragments thereof from HCV, as described herein. Also included in the present invention is a method for producing antibodies to a virus of interest comprising administering to an individual an isolated immunogenic polypeptide containing an epitope of the virus of interest in an amount sufficient to produce an immune response in the inoculated individual.

Furthermore, knowledge of the role of viral homology domains to host protein domains is applied to the development of a novel detection assay for accurately detecting and characterizing a viral infection. Preferably, diagnostic assays of the present invention are provided to a) provide improved sensitivity for early diagnosis of a viral infection; b) predict the probability of establishing persistent infection; and/or c) predict the ability of a virus of interest to induce autoimmunity.

According to a preferred embodiment of the present invention, an improved diagnostic method is provided for detecting hepatitis C virus and retrovirus infections. For example, several host protein domain sequence elements (HPDSEs) have been found within different regions of HCV polyproteins. In particular, over 100 of HPDSEs in HCV polyprotein have been identified, particularly in the E2, NS3, NS4, and NS5 gene regions. Based on our findings, that the second envelope protein (E2) and NS5A of HCV have been identified to contain domains or HPDSEs with homology to human immunoglobulin light chain variable region (IgVL) sequence, new diagnostic methods and tests having improved sensitivity and accuracy are provided in accordance with the present invention. Specifically, an improved diagnostic method of the present invention that reduces the rate of false positive detection of HCV, for example, in blood and/or provides an improved early detection capability is provided. Since the T cell receptor represents a family of hypervariable genes that are highly homologous to the variable, region of IgVL, we predict that procedures and methodologies that are modified according to consideration of homology of E2 to T cell receptor molecules, in parallel with our consideration of IgVL homology, will be similarly applicable to improving HCV methods for detection, diagnosis and treatment of HCV.

The present invention includes novel antigenic compounds having improved specificity for anti-viral antibodies, thus reducing the false positive rate in blood screening using serological tests. According to a preferred embodiment of the present invention, novel antigenic compounds devoid of HPDSEs identified as contributing to immune escape mechanism of HCV are provided. Alternatively, compounds of the present invention may contain HPDSEs, fragments thereof or altered HPDSEs. These novel antigenic compounds can be employed in the diagnostic methods of the present invention to provide improved serological tests. Such compounds may also be used as an effective treatment against HCV infection.

According to preferred embodiments of the present invention, antigenic compounds may include isolated amino acid sequences, polypeptides, recombinant proteins and synthetic peptides and/or fragments and combinations thereof. Furthermore it is contemplated that novel antiviral treatment compositions and vaccines may be provided in accordance with the present invention.

We thus propose that viral evolution in general and adaptation to a new host in particular involves a process of host mimicry as one means of increasing evolutionary fitness by avoiding host recognition and defensive response. We believe that the demonstrated instances of structural mimicry and/or sequence homology in RNA viruses are examples of a general process that is important for RNA virus survival. Specifically, we illustrate that viruses will tend to mimic their cognate host and thus a virus can be matched to its host by comparison of the relative extents of viral molecular mimicry to a given host. Given the recent advent of the human and mouse genome sequences it has become possible to analyze the structural mimicry of viral variants to these host genomes.

EXAMPLE I

Molecular Mimicry by HCV

To date, the mechanism for HCV persistence in infected individuals has been unclear. Viral replication during acute infection leads to a high frequency of amino acid substitutions in HVR1 that generates a complex mixture of genetic variants, termed a quasispecies. This genetic diversity translates into different amino acid sequences and thus, altered epitopes, resulting in different levels of recognition of quasispecies members by the host immune system[6,7]. For example, some epitopes within HVR1 are not recognized by the immune response and the corresponding variants that persist after seroconversion are termed antibody escape mutants or persistent quasispecies. It has not been previously known why these escape mutants are not subsequently recognized by the immune system. As a result, prior to the present invention, effective prevention, diagnosis and treatment for persistent HCV infection has not been available.

Amino acid mutation at the amino terminus of the HCV second envelope glycoprotein (E2), and more specifically within hypervariable region 1 (HVR1) of HCV has been identified, in accordance with the present invention to provide an elevated homology to human immunoglobulin light chain (kappa) (IgVLκ) in persistent HCV infections. The amino terminal region in E2 was identified as comprising a 124 amino acids region (as illustrated in FIG. 1a) that shows a significant homology to the variable region of human immunoglobulin light chain (kappa) (Ig-VLκ) in all HCV genotypes. Furthermore, four HCV major homology domains (MHDs) are described that correspond to surface loops of IgVLκ in antibodies.

During infection, sequence variation and mutation, particularly in HVR1, elicit significant changes in homology. Those variants with a lower homology to Ig-VLκ within HVR1 are eventually eliminated, while the variants with increased or sufficient homology to Ig-VLκ escape the neutralizing immune response and become persistent. As provided in accordance with the present invention the degree of homology of HVR1 of a HCV variant to IgVL will determine the level of recognition by the immune system and thus play a major role in viral persistence. Characterization of this strategy of molecular mimicry provides a fundamental understanding of the progressive development of HCV infection in a host and serves as a basis for disease intervention.

Molecular mimicry is one of the immune-evasion strategies viruses use to promote survival and persistence. There are several examples of viruses that express proteins that can modify or avoid host defenses because they are homologous to human protein sequences which are involved in the regulation of cell proliferation, intercellular signaling or immune functions[17]. For example human cytomegalovirus (HCMV) encodes a molecular homologue of major histocompatibility complex 1 (MHC 1) proteins (the UL18 gene product)[18], which is directly involved in evasion of cellular immune response by inhibiting recognition and attack by natural killer cells[19]. As well, molecular mimics of host protein domains by herpes virus type 1 (HSV-1) influence the development of autoimmune disease after viral infection[20]. The virally induced antiviral cytokine, interferon (IFN), acts in part through the dsRNA dependent protein kinase (PKR) that inhibits protein synthesis through phosphorylation of the initiation factor eIF2∀. The HCV E2 protein contains a PKR-eIF2α phosphorylation homology domain that competes with authentic eIF2∀ to inhibit the antiviral response mediated by IFN[20,5]. We reasoned that other instances of molecular mimicry could also be contributing to HCV persistent infection. In accordance with the present invention, we searched for homologous sequences to the HCV polyprotein among all known proteins available in GenBank. We found that HCV encodes a sequence in envelope region 2 (E2) that is highly homologous to human immunoglobulins (Ig), and that specifically possesses typical features of the variable region of Ig kappa light chain (IgVLκ) in some variants. Using a melded genomic, proteomic, and evolutionary approach, analysis of HCV E2 and HVR1 sequences that arise during infection in humans and chimpanzees we found that the degree of homology with Ig-VLκ within E2, and in particular within HVR1, is directly related to viral escape and persistence. Thus, the mechanism of HCV immune evasion and persistence involves a process of molecular mimicry.

The discovery of HCV encoded Ig-like protein domains, more generally referred to herein as host protein domain and sequence elements (HPDSEs), in accordance with the description of the present invention, and their role in circumventing the host immune response provides a mechanistic explanation for viral persistence. Molecular mimicry of host antibodies by HCV is a unique and efficient way to circumvent the immune response because it is focused on the variable region of antibody molecules which are both the effectors as well as targets for humoral immunity and are thus tolerated antigens. Host-like antigenic structures are not immunogenic due to tolerance mechanisms that operate to block the synthesis of self-reactive antibodies. In accordance with the findings of the present invention, our data show that HPDSEs, such as those target sequence elements within E2 and N5SA proteins in certain HCV variants co-evolve with host protein domain sequences, such as Ig domains, to establish persistent infection. That is, over time, these HPDSEs evolve to become more genetically similar or more highly homologous to host protein domain sequences. As a result, through genetic mutation a HPDSEs confers the ability of a viral variant to escape immune evasion of a host.

According to one embodiment of the present invention, at least 20% sequence homology between a HPDSE and a host protein sequence provides a threshold level of homology sufficient to mimic host protein structure and antigenicity. According to a preferred embodiment of the present invention, the sequence homology of a HPDSE and a host protein is at least 30%. According to yet another preferred embodiment of the present invention, molecular mimicry of IgVLκ by HCV HVR1 (1-27 aa) is achieved with a homology profile of 30%-45% homology because this is similar to the variation seen among IgVLκs, making HVR1 of a persistent HCV as antibody-like as other antibodies.

All the data support the conclusion that evolution of host protein domain sequence elements within HCV E2 to become more homologous to IgVL correlates directly with a viral variants ability to escape from immune detection, a process that is modulated primarily by epitopes in HVR1. These findings explain the nature of the extreme structural variation seen in HCV E2, in that HVR1 becomes structurally similar to host immunoglobulin to avoid immune detection.

A Sequence Homologous to IgVLκ in E2

FIG. 1a shows that a sequence of about 124 amino acids (aa) mainly between positions 384 and 514 in the E2 protein of all major genotypes of HCV (1a, 1b, 2a, 2b, 3a, 3b, 4a, 5a and 6a) is significantly homologous to the complete human light chain variable region of antibodies, IgVLκ, (109 to 120 aa). The extent of amino acid identity ranged from 23.3 to 38.7%, depending on the genotype and isolate (Table 1). Genotype 2a shared the highest homology with the antigen-binding domains of IgG1 from humanized anti-p185HER2 antibody 4D5[17] (identity 38.7%, Z-score 140.0) as well as human germline antibody (34.9%, Z-score 127.9) (SSEARCH Acc# 2rcsL). This comparative analysis of the HCV genome and human sequences employed the "Ssearch" program for genetic homology of a query sequence to another gene or group of genes. The FASTA program family (FastA, TFastA, FastX, TFastX, and SSearch) was written by Professor William Pearson of the University of Virginia Department of Biochemistry (Pearson and Lipman, Proc. Natl. Acad. Sci., USA 85; 2444-2448 (1988)). In collaboration with Dr. Pearson, the programs were modified and documented for distribution with Wisconsin Package Version 6.1 by Mary Schultz and Irv Edelman, and for Versions 8 through 10 by Sue Olson.

SSearch does a rigorous Smith-Waterman search for similarity between a query sequence and a group of sequences of the same type (nucleic acid or protein) This may be the most sensitive method available for similarity searches and compared to BLAST and FastA, can be very slow. SSearch uses William Pearson's implementation of the method of Smith and Waterman (Advances in Applied Mathematics 2; 482-489 (1981)) to search for similarities between one sequence (the query) and any group of sequences of the same type (nucleic acid or protein) as the query sequence.

SSearch uses William Pearson's implementation of the method of Smith and Waterman (Advances in Applied Mathematics 2; 482-489 (1981)) to search for similarities between one sequence (the query) and any group of sequences of the same type (nucleic acid or protein) as the query sequence. This method uses a scoring matrix (containing match/mismatch scores), a gap creation penalty, and a gap extension penalty as scoring criteria to determine the best region of local similarity between a pair of sequences. This score is reported as the Smith-Waterman score.

After the Smith-Waterman score for a pairwise alignment is determined, SSearch uses a simple linear regression against the natural log of the search set sequence length to calculate a normalized z-score for the sequence pair. (See William R. Pearson, Protein Science 4; 1145-1160 (1995) for an explanation of how this z-score is calculated.) The distribution of the z-scores tends to closely approximate an extreme-value distribution; using this distribution, the program can estimate the number of sequences that would be expected to produce, purely by chance, a z-score greater than or equal to the z-score obtained in the search. This is reported as the E( ) score.

When all of the search set sequences have been compared to the query, the list of best scores, along with the alignments, is printed. In evaluating the E( ) scores, the following rules of thumb can be used: for searches of a protein database of 10,000 sequences, sequences with E( ) less than 0.01 are almost always found to be homologous. Sequences with E( ) between 1 and 10 frequently turn out to be related as well.

To assess the significance of the observed homology between HCV E2 and immunoglobulins, we searched all known virus sequences for the presence of similar levels of similarity (identity>27% and/or E<0.5) to two germ line antibodies (Table 2). Only HCV and to a lesser extent HSV-1 (UL20 protein E>0.85), and some retroviruses were found to possess proteins that share homology with human antibodies (data not shown). We hypothesize that homology to immunoglobulins serves a specific function in the ability of HCV to escape immune surveillance and become persistent.

Figure 23:
FIG. 23 illustrates recombinant E2 cross-reacts with anti-human-IgG; wherein the amino terminal E2 region of clones derived from patient A, were appended to a 6 his amino-terminal tag (SEQ ID NO: 536), cloned into baculovirus and expressed in insect cells. Infected cell lysates were subjected to SDS-PAGE and either stained with coomassie brilliant blue (coomassie), or blotted and reacted with anti-histidine antibody and secondary antibody or with alkaline phosphatase conjugated goat anti-human-IgG and detected by NBT-BCIP staining. Lane 1, (aa 1-123 of a high IgVLκ homology (44.3%) E2 clone; lane 2, aa 1-113 of a low homology (37.3%) E2 clone; lane 3 aa 1-123 of an intermediate homology (40.9%) E2 clone, lane 4, control baculoviurs vector infected cells. The extent of recognition by anti-human IgG is related to the sequence homology where the E2 with the highest homology reacted most strongly with the anti-immunoglobulin antibody. Recombinant E2 cross-reacts with anti-human-IgG. The amino terminal E2 region of clones derived from patient A, were appended to a 6 his amino-terminal tag (SEQ ID NO: 536), cloned into baculovirus and expressed in insect cells. Infected cell lysates were subjected to SDS-PAGE and either stained with coomassie brilliant blue (coomassie), or blotted and reacted with anti-histidine antibody and secondary antibody or with alkaline phosphatase conjugated goat anti-human-IgG and detected by NBT-BCIP staining. Lane 1, (aa 1-123 of a high IgVLκ homology (44.3%) E2 clone; lane 2, aa 1-113 of a low homology (37.3%) E2 clone; lane 3 aa 1-123 of an intermediate homology (40.9%) E2 clone, lane 4, control baculoviurs vector infected cells. The E2 protein is recognized as immunoglobulin-like by reaction with anti-human-IgG antibody with the high homology E2 showing stronger reactivity than the lower homology clones.

In FIG. 23, we provide the cross-reactions of recombinant E2 with anti-human-IgG; wherein the amino terminal E2 region of clones derived from patient A, were appended to a 6 his amino-terminal tag (SEQ ID NO: 536), cloned into baculovirus and expressed in insect cells. Infected cell lysates were subjected to SDS-PAGE and either stained with coomassie brilliant blue (coomassie), or blotted and reacted with anti-histidine antibody and secondary antibody or with alkaline phosphatase conjugated goat anti-human-IgG and detected by NBT-BCIP staining. Lane 1, (aa 1-123 of a high IgVLκ homology (44.3%) E2 clone; lane 2, aa 1-113 of a low homology (37.3%) E2 clone; lane 3 aa 1-123 of an intermediate homology (40.9%) E2 clone, lane 4, control baculoviurs vector infected cells. The E2 protein is recognized as immunoglobulin-like by reaction with anti-human-IgG antibody with the high homology E2 showing stronger reactivity than the lower homology clones. The present data additionally confirms that the extent of recognition by anti-human IgG is related to the sequence homology where the E2 with the highest homology reacted most strongly with the anti-immunoglobulin antibody.

Figure 24:
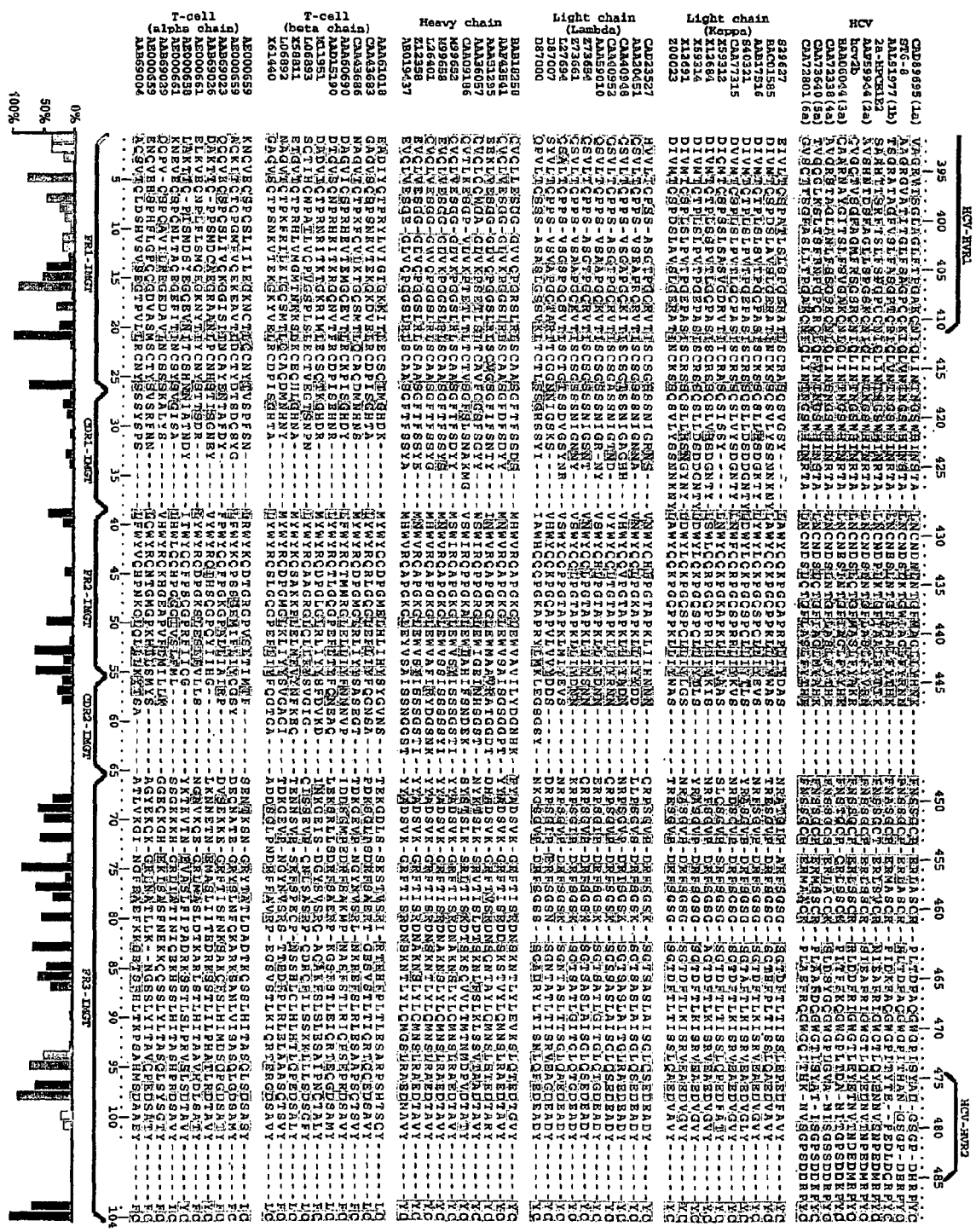
FIG. 24 illustrates the alignment of a panel of HCV E2 proteins with members of the immunoglobin v-gene family, wherein a panel of 10 HCV E2 sequences representing the 6 major genotypes are aligned in the IMGT numbering (http://IMGT.cines.fr) with immunoglobin heavy, kappa, lambda T cell receptor alpha and T cell receptor beta genes; for each gene the accession number is given (SEQ ID NOS 335-394, respectively, in order of appearance). Immunoglobin family members are composed of 5 rearranged genes plus 5 germ-line genes. Those amino acids that are in common with E2 sequences are indicated in red reverse video text. The extent of sequence identities among all aligned genes is indicated as percentages in the bar graph at the bottom. This statistical assessment of sequences provides a confirmation of sequence homology among E2 sequences and immunoglobulin and T cell receptor v-genes. Alignment of a panel of HCV E2 proteins with members of the immunoglobin v-gene family. A panel of 10 HCV E2 sequences representing the 6 major genotypes are aligned in the IMGT numbering (http://IMGT.cines.fr) with immunoglobin heavy, kappa, lambda T cell receptor alpha and T cell receptor beta genes. For each gene the accession number is given. Immunoglobin family members are composed of 5 rearranged genes plus 5 germ-line genes. Those amino acids that are in common with E2 sequences are indicated in red reverse video text. The extent of sequence identities among all aligned genes is indicated as percentages in the bar graph at the bottom.

The data provided, as shown in FIGS. 23 and 24, illustrates a direct demonstration of the structural homology of the amino terminal region of E2 with human immunoglobin. The HCV E2 amino terminus is recognized by antibodies against human immunoglobulin (as illustrated FIG. 23). The significance of these results, wherein the structural homology that is shared between the pathogen and its host is a determinant of the biological properties of the pathogen is a significant feature of the teachings of the present invention. Furthermore, of additional and corroborating evidence is the demonstration of the statistical similarity of the structure of the amino terminal region of HCV E2 with immunoglobulin and T cell receptor v-genes (FIG. 24).

FIG. 24 provides statistical proof of sequence homology between the amino terminal portion of the HCV E2 protein and v-genes (variable genes) of immunoglobulins and T cell receptors. This alignment shows that E2 has high homologies that includes patterns of amino acids that are not due to chance events; patterns of homology that include >7 amino acid sites are indicative of significant homology and not due to random chance.

More particularity, in FIG. 24, there is provided the alignment of a panel of HCV E2 proteins with members of the immunoglobin v-gene family. A panel of 10 HCV E2 sequences representing the 6 major genotypes are aligned in the IMGT numbering (http://IMGT.cines.fr) with immunoglobin heavy, kappa, lambda T cell receptor alpha and T cell receptor beta v-genes. For each gene the accession number is given. Immunoglobin family members are composed of 5 rearranged genes plus 5 germ-line genes. Those amino acids that are in common with E2 sequences are indicated in red reverse video text. The extent of sequence identities among all aligned genes is indicated as percentages in the bar graph at the bottom. Therefore, this statistical assessment of sequences provides a significant confirmation of sequence homology among E2 sequences and immunoglobulin and T cell receptor v-genes.

The Features of IgVLκ-like Domains

Comparison of la panel of antibodies representing the 4 subgroups of IgVLκ and all the major genotypes of HCV (FIGS. 1a and 1b), shows that HCV E2 can be divided into four major homology domains (MHDs) defined by aa regions 8-27 for MHD1, 37-46 for MHD2, 58-70 for MHD3 and 100-120 for MHD4 (counting from the N-terminus of E2). MHD 1 is located in HVR1 and corresponds with the sequence at the beginning of framework 1 (FR1) (1 to 20 aa) in IgVL of antibodies which functions to both support and contribute to the antigen binding site. MHD 2, 3 and 4 align with the 3 immunoglobulin hypervariable domains at positions 27-34, 49-60 and 90-109 aa, that comprise the complimentarity-determining regions 1 (CDR1), 2 (CDR2) and 3 (CDR3), respectively in the antigen binding site of IgVLκ. To further assess the homology of HVR1 to FR1 of IgVL, that are both highly variable, we also aligned consensus sequences representing the most prevalent amino acids for 1,382 HCV isolates[18] and 500 immunoglobulin light chain genes from human and mouse (FIG. 1c).

E2 and IgVL Biochemical Features

Firstly, in MHD1 there is high sequence homology between the consensus sequence of HVR1 and IgVL FR1, with 10 out of 20 amino acids (50%) of the most prevalent HVR1 amino acids at positions 9(Ala) 10 (Ala), 12(Thr), 14(Ser), 16(Leu), 17(Ther), 21(Ser), 22(P), 23(Gly) and 25 (Ser) being identical with the most prevalent amino acids at the corresponding positions in IgVL of antibodies. The master consensus sequence, derived from both HVR1 and IgVL, possesses identical amino acids at 14 of 20 positions (70%) including several positions where all or most of the alternative sequences in the consensus of HVR1 are also identical with those of immunoglobulin. The consensus homologies are within the range of homologies seen among IgVL FR1 regions (25-90%; FIG. 1e). Secondly, there are common amino acids that control molecular shape in IgVL molecules where CDR backbone shape is strongly influenced by alterations of specific resident amino acids (usually Pro and Gly), especially those at positions 15 and 16 in FR1 of IgVL that corresponds to 22 (Pro) and 23 (Gly) in HCV HVR1. These amino acids allow bending through the adoption of unusual torsion angles[19]. Other features that are crucial for the correct positioning of the CDR loops are completely conserved in the corresponding positions in E2 (e.g 69Gly and 103Cys) with those in IgVLκ (56Gly and 90Cys; as well as other residues 26Ser, 46Leu, 102Tyr). Specific amino acids positions were highly conserved in E2 molecules (ie TRP38 and 108) that may maintain three-dimensional structure of E2 (possibly involving cysteines 47, 70, 77 and 107 that border or involve MHDs 2, 3 and 4). The third common feature for HVR1 and IgVL FR1 is that amino acid replacements are frequently restricted to amino acids with similar biochemical properties, being rich in small flexible residues (Ser, Thr, Ala, Gly), appearing at IgVL positions 5, 7, 10 and 14, and at HVR1 corresponding positions 12, 14, 17 and 21 that were always substituted with Ser, Thr and Ala. These amino acids are not only structurally flexible but also can hydrogen bond to other amino acids to promote binding activity (FIG. 1c.). Finally, the residues in the MHDs 2, 3 and 4 in HCV were highly conserved among different genotypes of the virus, which was opposite to that of residues in the CDRs that show the greatest variability among antibodies. Presumably, the highly conserved residues of MHDs 2, 3 and 4 in HCV were initially adopted from CDRs of IgVLκ and fixed through evolution under selective pressures. It appears that HCV E2 possesses typical features of Ig-VLκ that includes not only aa sequence, chemistry and variability but also critical features that determine molecular conformation and secondary structure. As most members of the immunoglobulin super-family maintain a binding function it is appealing to speculate that E2. uses the IgVL homology domain as a binding site. These common structures in E2 are also expected to share the property of immune tolerance because HCV MHDs correspond to the exposed, surface loops, of antibodies that are recognized as self and not foreign antigens (FIG. 1d).

E2 Evolution and Viral Persistence

The common features of aa composition and variability in E2 and IgVLκ suggested that E2, including HVR1 sequence variation was not random and that the trend in variation was in response to selective pressures from the immune response[18]. The presence of two major forms of quasispecies that differ in their ability to persist in the infected individual has been suggested in humans[20] as well as in HCV infected chimpanzees that possess HCV quasispecies to which there is little or no immunity[27]. We analyzed the evolution of E2 sequence from a defined source to a recipient patient with acute nosocomial HCV 1a infection during the period of progression from acute to chronic infection[22]. FIG. 2a shows that multiple forms of variants appeared and disappeared over the, course of infection. The sequence encompassing the amino terminal 108 aa region of E2 including HVR1 is quite homogeneous in the quasispecies of the source virus (S1) from a patient with chronic HCV infection, where 85% (17/20) of the clones were identical with the remaining clones differing only due to one mutation. In contrast, 6 to 14 amino acid replacements were observed in HVR1 in 9 of 28 clones (32%) on day 36 (sample A1, pre-seroconversion) and in 4 of 24 (16%) clones at day 46 post infection (PI) (A2, early-seroconversion) in the nosocomial patient. Four weeks after seroconversion, (72 days PI), all the clones (30/30, 100%) were found to be the same or genetically similar in sequence to those clones from the source virus in S1. The most divergent viral sequences found in A1 and A2, carrying multiple mutations in HVR1 disappeared after antibody induction as seen in the A3 sample. The quasispecies shifts suggest that during acute infection, two types of quasispecies variants co-existed, one was restricted (i.e. non-persistent forms) and another was naturally selected and became persistent after seroconversion (i.e persistent forms of variants).

The genetic variation with respect to changes in homology to IgVL for persistent and non-persistent forms of the virus in the course of infection from acute to chronicity are shown (FIG. 3a,b). Three substitutions at aa positions 9 (Ala→Thr or Pro), 13 (Val→Ala) and 15 (Thr→Ala or Gly) that occurred within HVR1 of the non-persistent variant clones (i.e. 32% for A1 and 16% for A2 samples) had reduced. the degree of homology to IgVL FR1 consensus sequence from 40% to 25%. In contrast, no such low-homology-variants remained in the A3 sample, instead those variants that were genetically identical or similar to the source virus (S1) with higher IgVL homology (35%-40%) in HVR1 became predominant (100% of clones). In addition to the HVR1 substitutions, Asn 62 had mutated to several different amino acids (Arg, Tyr and Ser; FIG. 2 and data not shown) in the non-persistent A1 and A2 clones. The repeated occurrence of independent mutations at the same site is strong evidence of convergent evolution, indicating functional importance. This substitution decreased the homology of the "YRNN" motif (SEQ ID NO: 75) in MHD 3 relative to CDR2 of antibodies. It appears that amino acid variation within, as well as adjacent to HVR1 resulted in a trend of E2 protein domain shifting to a higher homology to human IgVLκ during quasispecies evolution and that the variants with higher homology to IgVLκ became predominant in the persistent virus population. The disappearance of the non-persistent variants coincided with a 100-fold decrease in viral load as HCV antibodies were produced (data not shown). The results suggest that genetically distinct populations of variants had undergone a selective process from the immune response during seroconversion, and that this controlled the outcome of infection. Convergence of HCV homology with IgVL occurred in HVR1 within MHD1 and to a lesser extent in MHD2 which appeared to be crucial for viral persistence. However, the sequences of MHDs 3, 4 and in particular 2, were relatively conserved suggesting that mutations in these MHDs may deleteriously alter the level of recognition by the immune system.

To corroborate the initial observation that chronic infection involves selection of variants with increased homology to IgVL we analyzed the quasispecies evolution in another, previously described, case of acute nosocomial infection by genotype 2c during progression from acute to chronic infection[23]. FIG. 3c indicates that the major quasispecies with the parental HVR1 sequences disappeared to be replaced by 9 different groups of variants with 11 to 14 (55%-70%) aa substitutions in HVR1 that became dominant in the virus population within 12 months. Although heterogeneous, the substitutions resulted in significant increases in homology of HVR1 to IgVL FR1 going from 35% to 45-55% in 100% of the variants after 1 year. The results now obtained from two follow-up. studies, confirmed the trend of quasispecies evolution toward higher homology to IgVL during the establishment of viral persistence. Another way to assess the impact of the immune response on the evolution of viral quasispecies is to examine HCV evolution in individuals, with immune system defects that result in low or minimal immune selective pressure. Several studies[24,25] have shown that that there is either no or fewer mutations in the dominant amino acid sequence in HVR1 in immuno-compromised patients. We found that these few mutations in the dominant variants in some patients had slightly decreased the homology to IgVLκ, while the degree of homology remained unchanged in most cases (FIG. 3). This further indicated that the variation of homology of HVR1 sequence to IgVLκ is constrained under immune selective pressure and that without immune selection the initial dominant variants would maintain the same degree of homology to IgVLκ in HVR1.

HCV-IgVLκ Homology in Chimpanzees

We examined a large number of HVR1 sequences available from several longer term, follow-up studies (up to 13 years) of experimental infections in chimpanzees. We found that that no matter how diversified HCV HVR1 sequences became over the course of an infection, the degree of homology to IgVLκ within HVR1 increased progressively (or remained the same in one animal, data not shown) for the predominant quasispecies (determined by direct sequencing) and specific persistent quasispecies (determined by cloning based sequencing). FIG. 4 shows that during infection of "Peggy"[26], mutations appeared starting at 92 days PI at position 22 (Leu→Pro) and 28 (V→I), accumulating three more by 3400 days (9 years) PI, 15 (Gly→Ser), 21(Asn→Ser) and 24 (Ala→Gly). Four of 5 mutations, 15 Ser, 21Ser and 22Pro and 28Ile, were identical to the conserved or relatively conserved residues in IgVLκ. Thus, the homology of HVR1 to IgVL had increased from 35% to 50% in aa identity. A similar profile and trend of the HVR1 sequence evolution was found in another chronically infected animal (Hans) where homology between HVR1 and IgVLκ increased from 35% to 45% after 9 years. A sequence analysis from a 12 year follow up study in a HCV chronic infected chimpanzee[27] showed the same trend of HVR1 evolution toward higher homology to IgVL (45%), even though the degree of the homology of HVR1 to IgVL had been high (35%) one year, after the infection (FIG. 4c). As seen in human HCV infection, experimental establishment of persistent infection of chimpanzees also involved the selection of variants with increased homology to IgVL. We also found that IgVL homology of HVR1 increased in a cohort of common-source HCV infected women who were monitored for 17 years (data not shown).

HVR1 Evolution and Epitope Shifts

MHD1 includes two IgVLκ-homology motifs, Thr-Leu-Thr (TLT) and Ser-Pro-Gly (SPG) at positions 14-18 and 22-23 respectively, that were frequently found in the relatively conserved consensus sequence in the HVR1 region. The two motifs reside in a region encoding two B-cell epitopes as identified by the work of Kato[23],[3]. Each epitope contains 11 amino acids at overlapping positions spanning aa 11 to 21 and 14 to 24 (i.e. 394 to 404 and 397 to 407 in the polyprotein) for epitopes 1 and 2 respectively. It was found that on establishment of persistent infection amino acid substitutions in each HVR1 epitope led to escape from recognition by preexisting anti-HVR1 antibodies[23]. However, it was not known why the substitutions allowed the mutants to escape subsequent immune recognition. We analyzed the significance of sequence homology to IgVLκ within the epitopes in relation to mutant escape. FIG. 5 indicates that three of the four substitutions at positions 14 (Arg→Ser), 16 (Phe→Leu) and 18 (Ser→Asn) resulted in significant increases in homology to IgVL for both epitopes 1 and 2. The changes in homology directly correlated with the levels of recognition by antibodies and therefore the generation of antibody escape mutants. The substitution Phe→Leu which appeared at 6 months post diagnosis (p.d.) changed the homology to IgVLκ from 27% to 36% for epitopel and from 36% to 45% for epitope 2. At that time, variants with this mutation were found to be non-reactive to the anti-HVR1 antibodies existing at 6 and 8 months p.d. in serum. One more substitution Arg14→Ser in HVR1 occurred at 11 months p.d, which further increased the IgVLκ homology to 45% for epitopel and to 54% for epitope 2. These variants with 14Ser and 16Leu mutations in HVR1 completely escaped antibody recognition, showing a negative reactivity to preexisting antibodies at all time points of 6, 8, 11 and 14 months p.d. in antibody binding assays. It appears that when homology to IgVLκ reached levels of 45% in epitopel and 54% in epitope 2 that this was not only sufficient to escape from recognition by preexisting antibodies but also prevented the further recognition of this epitope since it was not subsequently recognized by antiserum collected at 19 months p.d in this individual[3]. To corroborate this result, we examined the homology changes, of the sequences in the two epitopes of HVR1 from the non-persistent and persistent variants found in 2 follow-up studies[33],[34],[23] In both studies the homology of eptitopes 1 and 2 to IgVL dramatically increased, approaching or exceeding 50%, in persistent variants.

HCV Diagnosis and Treatment Regimes

We have genetically characterized clinically relevant biological forms of HCV variants with respect to resistance/sensitivity to interferon as well as resistance/sensitivity to antibody neutralization. These properties relate directly to the degree of homology, of HVR1 and E2 and NS5A proteins to immunoglobulin sequences (Table 3, and FIGS. 7, 8, and 9). Antibody-sensitive variants are resistant to IFN while antibody-resistant variants are sensitive to IFN treatment. As high dose IFN therapy reduces antibody levels it is possible for otherwise antibody sensitive HCV viruses to survive in IFN treated HCV infected patients. These conclusions derive from results obtained by the analysis of quasispecies evolution and selection in the course of HCV infection in a follow up study (FIG. 6 and Table 3).

By analysis of viruses that survive seroconversion in sample A3, it was observed that viruses with ≧35% homology in the HVR1 region and ≧40.3% homology in the larger E2 region (aligned in FIG. 6) can resist antibody neutralization. HVR1 homologies of less than 30% and E2 homologies of less than 37.8 were removed by the antibody response. In Table 3 it is further demonstrated that the virus populations that survived IFN treatment and are thus identified as IFN resistant have less homology to IgVLκ in the HVR1 region and the larger region of E2 including HVR1 HPDSEs, than the antibody resistant population. These viral populations are thus predicted to be more susceptible to antibody neutralization. These viruses in post IFN treatment sample A4 comprise 2 populations in Table 3. The majority of the IFN resistant population (90%) is seen to have a homology to the HVR1 and E2 region that is near the lower limit of homology of variants that are antibody resistant. The remainder of IFN resistant population (10%). is similar to the antibody sensitive population and subsequently disappears from the A5 population. We predict that stimulation of the antibody response in conjunction with IFN treatment will sterilize such patients to provide a complete removal of both of these virus populations and thus cure infections. Accordingly, the present invention provides individual treatment regimes for viral infections that are tailored to target specific viral variant(s) infecting a host. One such example includes a combination treatment regime comprising a first treatment with IFN to target an antibody resistant viral variant(s). This first treatment will effectively remove those IFN-sensitive variant(s), while leaving a population of viral variants that are more susceptible to antibody neutralization. This treatment is followed by a second treatment with variant specific antibodies. Alternatively such an individualized treatment may be a combination treatment, including administering IFN and variant specific antibodies simultaneously in the form of a combination treatment cocktail, for example. Furthermore, a tailored treatment regime for selectively targeting evolving viral variants based on homology profiles thereof is provided, as described in accordance with the present invention. For example, homology profiles can be determined at predetermined intervals and corresponding treatment regimes and/or preparations used in response thereto. In this manner, a viral infection is effectively characterized over time and a corresponding treatment regime administered to effectively and efficiently combat the infection.

Treatment modalities for removing viral variants with lower HPDSE homology to IgVLκ may include immunization to stimulate the production of antibodies and thus increase the neutralization response or the application of antibodies or other medicaments that will augment the neutralization response.

These data predict that an HCV infection can be more effectively treated, than the current state of the art, by a combination of immunotherapy (consisting of an antibody preparation or immunogenic compound) and/or antiviral medicament plus IFN, which will remove both IFN and antibody sensitive HCV virus variants present in a patient. Specifically, optimal treatment modalities, comprising combinations of immunotherapy as well as anti-viral medicaments (antibodies, immunogens, or medicaments) specific for antibody sensitive HCV in combination with IFN, that correspond to the predicted sensitivities of a virus variant(s) in the patient The present invention identifies immunoglobulin proteins as being anti-genetically similar or sufficiently homologous to persistent strains of HCV. Accordingly, the treatment of HCV virus infection with antibody preparations or drugs that are directed to HVR1 of E2 may be blocked in a competitive manner by immunoglobulins. According to one embodiment of the present invention, immunoglobulins are removed from blood by plasmaphoresis or other means before treatment with drugs or compositions that function by interacting with HVR1 or other immunoglobulin-like HPDSE regions.

We have also found that NS5A contains a sequence homologous to an IgG sequence and the degree of homology between NS5A and IgG is directly related with the outcome of IFN treatment (FIGS. 7, 8 and 9). According to one embodiment of the present invention a viral characterization and/or diagnosis and corresponding treatment regime can be determined based on identification of a sequence homology of a NS5A HPDSE and an IgG sequence domain in a patient infected with HCV.

In particular, in accordance with an embodiment of the present invention the clinical outcome of viral infections and corresponding treatment regimes can be predicted. For example, the use of specific antibodies (monoclonal and polyclonal) combined with IFN can be predicted based on the sequence characteristics of different forms of viral variants for targeted treatment regimes.

Based on the findings of the present invention that the second envelope protein (E2) and NS5A of HCV contain human immunoglobulin light chain variable region (IgVL) sequence and that homology changes during the time-course of infection are directly correlated with B-cell epitope shifting, antibody binding, immune escape, and antiviral treatment it is suggested that, some viral "capture antigens" and proteins used in serological tests, may specifically or non-specifically react with immunoglobulins (IgGs), Ig-antigen complex and other related host proteins to cause a high rate of false reactivity in existing commercial serological test. To circumvent this problem, a novel set of capture antigens without target sequence elements (HPDSEs), having specificity to a viral variant of interest, are provided in accordance with the present invention. These antigens are expected to be more specific to anti-viral antibodies, and thus reduce the false positive rate in screening assays, such as serological tests. Similarly, we expect these novel antigens, in which target sequence elements or HPDSEs of interest are absent, to be useful in the preparation of novel anti-viral compositions and vaccines.

Treatment of HCV Induced Autoimmune Diseases and Non-Hodgkin's B-cell Lymphomas

HCV persistent infection is associated with high incidences of clinical syndromes that are either autoimmune or mediated by immune complexes and that are all associated with the formation of immunoglobulins that bind other immunoglobulins including rheumatoid factor. The autoimmune diseases most closely associated with chronic HCV infection are essential mixed (type II) cryoglobulinemia (MC), membranoproliferative glomerulonephritis, and porphyria cutinea tarda. The normal antibody response to HCV infection includes a major fraction of circulating immunoglobulins (Igs) that are part of the spectrum of the so-called natural antibodies, which include anti-idiotypic antibodies and molecules with rheumatoid factor (RF) activity. They mainly belong to the IgM class, are polyclonal, and have no intrinsic pathogenetic potential. In 20-30% of HCV-infected patients, RFs share characteristics of high affinity molecules, are monoclonal in nature, and result in the production of cold-precipitating immune complexes and mixed cryoglobulinemia.

It has been shown that anti-idiotypic antibodies and polyclonal and monoclonal RF molecules have the same cross-reactive idiotype, called WA, suggesting that their production is highly restricted. This strongly suggests that they arise from stimulation with the same antigen, likely HCV. (Dammacco F, Sansonno D, Piccoli C, Racanelli V, D'Amore F P, Lauletta G. *The lymphoid system in hepatitis C virus infection: autoimmunity, mixed cryoglobulinemia, and Overt B-cell malignancy.* Semin. Liver Dis. 2000;20(2):143-57).

Identification of HPDSEs, in accordance with the present invention, that correspond to host protein sequences implicates a relationship between a HCV HPDSE and the stimulation of immunoglobulins that cross-react with other immunoglobulins during chronic infection. Accordingly, the present invention provides a novel indicator of autoimmunity in a host. Furthermore, the knowledge of the nature of antigenic stimulation, such as the presence of a HPDSE in E2 of HCV, for example, can be used to diagnose and treat autoimmunity induced either directly or indirectly through the mechanism of antigenic mimicry. According to one embodiment of the present invention, a HPDSE having a correlation to immunoglobulin sequences of a host, are identified as a direct inducer of cross-reactive immunoglobulin. In this manner, a HPDSE has utility as an indicator of auto-immune disease.

There is an additional association between HCV patients with MC and lymphoproliferative disease. The HCV associated Non-Hodgkins B-cell lymphomas are found to express immunoglobulins that are similar or identical to immunoglobulin WA but also including antibodies with similar sequence that can react with HCV E2 (see Table 4 and FIG. 10). This indicates that lymphoproliferative disease is antecedent to chronic stimulation of WA antibody production during HCV infection and furthermore that this antibody response is initiated by HCV E2 antigen. Specifically, a further embodiment of the present invention identifies HPDSE in E2 as the stimulating antigen for the production of antibodies that cross-react with other antibodies characterized by WA monoclonal rheumatoid factor and that this condition proceeds to lymphoproliferation of WA or WA immunoglobulin-like synthesizing B cells.

Accordingly, this embodiment of the present invention identifies the source of immune stimulation for the genesis of the anti-immunoglobulin and other autoimmune responses, as a HCV HPDSE that corresponds to immunoglobulin and other host antigens and that forms the basis for autoimmune diseases including MC that proceeds to B-cell lymphoproliferative disease. An autoimmune response may contribute to the chronic inflammation that precedes HCV induced hepatocellular carcinoma and cirrhosis.

According to this finding, a HPDSE can serve as a useful indicator of auto-immune disease and/or certain forms of lymphoma or of a predisposition for the development of an auto-immune disease and/or certain forms of lymphoma. Furthermore, according to another aspect of the present invention, a WA antibody or other cross-reactive immunoglobulin can be used as a screening agent to detect autoimmunity in a patient. In addition, a HPDSE may serve as a useful target in the prophylaxis and/or treatment of a viral infection. Specifically, the present invention includes use of a compound having specificity to a HPDSE for the treatment of a viral infection. One such example is the use of a compound having specificity to a HPDSE such that the compound will target a HPDSE and serve to block the evolutionary development of that HPDSE so as to interfere, deter or prevent mutation of the HPDSE towards a higher degree of homology with a host protein sequence.

Autoimmunity

The immune response to HCV is slow requiring 7 weeks as compared to 1-2 weeks for a typical acute viral infection. Although this response is slow it is effective in clearing infection from 15% of those infected with the remaining going on to persistence. The virus that is present before seroconversion can be neutralized with the serum antibody present during persistent infection whereas the persistent form of HCV is resistant thus constituting antibody escape variants of the acute form of the virus. Our observation of a conversion of the E2. epitope to become IgG-like explains both the structural basis for antibody escape as well as the inability of the persistently infected patient to mount an immune response due to immune tolerance.

Although persistently infected individuals do not mount a neutralizing antibody response it is possible that continued stimulation of the immune system by the PI IgG-like sequence leads to a partial breaking of tolerance and the production of antibodies that cross-react with the host. This finding may explain why 75% of patients with chronic hepatitis C have autoimmune responses. The stimulation of cross-reactive antibodies may be directed to IgG and be responsible for the high incidence (56%) of cryoglobulinemia associated with HCV persistence. The occurrence on a liver specific antigenic region immediately adjacent and overlapping with HVR1 may be responsible for stimulation an anti-hepatocyte immune response that may be responsible for continuous hepatocyte damage by CTL or antibody dependant cellular cytotoxicity (ADCC). Partial immune recognition of the HCV E2 leads to antibody that cross-reacts with host leading to autoimmune disease. This can involve antibodies that cross react with IgG as well as antibody that cross reacts with a liver antigen that is adjacent to the HVR1 region and is nearly identical in 19/20 aa. Thus the nature of the antigenic change supports a mechanism of altered receptor biology associated with enhanced ability to establish infection followed by a mechanism of avoidance of immune recognition by mimicking host antigens.

The observation that both E2 of HCV and the UL6 protein of herpes simplex 1 virus possess high homology to the IgG variable domain is highly significant since both of these viruses can cause auto immunity. Furthermore the UL6 gene controls the ability of HSV to cause autoimmune herpes stromal keratitis since mutants that failed to express UL6 protein do not cause autoimmune keratitis. The T cell clones that cross-reacted with corneal self antigens also reacted with a peptide region that is homologous to the variable region of IgG2a. It is thus possible that the IgG2a cross-reactive epitopes contribute to autoimmunity especially in conjunction with other cross-reactive regions present on the same protein as occurs for both E2 and UL6 that contain liver and corneal antigens respectively. These data further underscore the role of antigenic mimicry in HCV persistent infection and autoimmunity by antigenic mimicry.

Hepatits C Virus Evolution: E2 Domain Shifts to IgG-like Sequence

Protein Domain Shifts Within E1/E2

The present invention suggests that some quasispecies are continuously eliminated by neutralization antibodies synthesized in their presence, and are replaced by some variants that escape from immune response and subsequently become predominant quasispecies. HVR1 is identified as the major immunogenic domain of E2, although the presence of additional B-cell sites outside HVR1 has been documented. The presence of two epitopes within HVR1 suggested that epitope shift occurred during the course of hepatitis C viruse infection (Nobuyuki Kato, et al. 1994, J Virol, 68:4776-4784) and it has been thought that the epitope shift within the E1/E2 region, in particular the hypervariable N-terminal region of E2, plays a major role in the escape mechanism. The definition of two major forms of quasispecies, non-persistence and persistence forms of, quasispecies with different genetic and biological characteristics at protein levels has facilitated the study on the mechanism of how the persistence quasispecies could attenuate or evade the immune response. Genetic changes at amino acid level in viral proteins is correlated with alteration of neutralization properties of viral mutants as seen in many lentiviruses such as retroviruses including SIV in monkeys and HIV in humans (Burns D P, Collignon C, Desrosiers R C. 1993, J Virol; 67:4104-4113, Robert-Guroff M, Brown M, Gallo R C,. Nature 1985; 16:72-74,). Even a single amino acid change can abrogate CTL recognition, leading to the persistence of the viral mutant in vivo (Koup R A. Virus escape from CTL recognition. *J Exp Med* 1994; 180: 779). The significance of the substitutions or mutations in the establishment of viral persistence in HCV infection has not been addressed to date. In accordance with the present invention, we proposed that the stabilized or fixed amino acid sequence within the E1/E2 region in persistence variants may comprise protein domains and /or epitopes that may lead to low or no recognition of the virus envelope proteins by the immune system. All known protein sequences from different species in both prokaryotic and eukaryotic systems in GenBank were analyzed and aligned with amino acid sequences within the E1/E2 region derived from the clones of the persistence and non-persistence variants using SSEARCH and NCBI Blast. The protein sequences available from GenBank with homology scale of E value lesser or equal to 10 and/or Z-score higher than 104.6 (equal to E value 9.3) were selected and displayed for comparison of their similarity with the sequences of all cloned quasispecies including persistence and non-persistence variants. A number of the clones from the sample (S1) from the virus source patient with chronic hepatitis C were also analyzed. Table 4 illustrates a great concordance, of results between the two methods of direct DNA sequencing, and cloning and sequencing of quasispecies. The data from the cloning and sequencing method indicates that the amino acid sequence within the E1/E2 region in more than a half (9/16, 56.3%) of the quasispecies, existing only in pre-and early-seroconversion samples (A1 and A2), mutated to the sequences homologous to the sequences of protein, domains from microbes. They include the domains from bacterial integral membrane protein (IMP) and molybdate protein from *E. Coli,* hydolyse from fungi and viruses and coat protein from bacterial phage. All the variants (A1-7, -8, -12, -15, -16, and A2-7, -1, -8 and -11) with the homologous sequences to the sequences of microbe protein domains were found to be non-persistent. In contrast, the amino acid sequence within this region of the majority (75-100%) clones of the quasispecies representing the persistence form of variants in the post-serocoversion sample (A3) and virus source patient sample (S1) have shifted to the sequences that are homologous to the sequences from human protein domains. They include the bactericidal/permeability-increasing protein (BPI) (Beamer, L. J., S. F. Carroll, D. Eisenberg, 1997, Science 276: 1861) and immunoglobulin variable region (Ig-V) domains (Marquart, M., and R. Huber, 1989, Biol. Chem. Hoppe-Seyler 370: 263). These results suggest that only the variants in which the protein domain shifts to the host protein domains in E1/E2 region can escape the immune surveillance, and become the predominant population after seroconversion and in the course of chronicity of the virus infection. In addition, the results also indicate that the minority (25%) of quasispecies in patients with chronic HCV infection carried the protein domain in E1/E2 region mutated to the sequence that was homologous to IMP and bacterial protein of glucarate seen in the sample S1. It suggests that some non-persistence variants may frequently occur and will be eliminated after specific antibody is produced, but cannot be the predominant population of variants in most patients with chronic HCV infection. The direct DNA sequencing analysis allows detection of the master sequence and is useful for measurement of amino acid sequence changes in the consensus sequence of a population of genome (Leen-Jan van Doorn, et al. J Virol. 69:773-778,1995). The results from the direct DNA sequencing data show that the protein domain shifted to IMP domain in the E1/E2 region in the isolates A1, A2. While the sequence within E1/E2 of A3 and S1 isolates was more homologous to that of human protein domains of BPI and/or Ig-V. Data from both methods have concordantly indicated that the protein domain shifts due to the mutations occurred within E1/E2 in the course of HCV primary infection trend towards to the human protein domains.

EXAMPLE II

Parallels with HIV

HCV virus infection in humans primarily occurs in hepatocytes and liver macrophages, however HCV RNA is also often found in lymph nodes and the pancreas. The evolutionary biology of HCV may have parallels with that of human immunodeficiency virus (HIV) that also causes persistent infections where the virus is present as a heterogeneous and varying population in the infected individual. Of more direct relevance to our interpretation of genetic variation in HCV as it relates to disease is the observation that most of the genetic variation involves the hypervariable regions in the gp120 receptor protein. HIV biology is dependent on the cell tropism of HIV that is controlled by binding of virus to the CD-4 receptor in conjunction with co-receptors on macrophages and T cells. Thus macrophage tropic HIV binds the CCR5 chemokine receptor whereas T-cell tropic HIV virus binds the CXCR5 chemokine receptor. The receptor specificity of HIV shifts during persistent infection from being M-tropic early in infection to being T-tropic at the onset of disease by virtue of mutations in the viral receptor. Persistent infection with human immunodeficiency virus (HIV) is thus associated with evolution of the receptor tropism on progression to disease. Interestingly, transmission repeats this selection indicating that the T-tropic virus that is selected during persistent infection is not optimized for establishing an infection in a new host. Given that commercial sex workers who are repeatedly exposed to HIV but who lack the macrophage co-receptor do not become infected in spite of having T-cells that can be infected in vitro indicates that successful infection requires the initial infection of macrophages to establish an acute infection that then mutates to T-cell tropism to cause disease. Although HIV infections contain mixtures of M-tropic and T-topic virus new infections are initiated by the M-tropic components. Presumably the macrophage response must be perturbed in order to successfully infect T cells in vivo. This is directly analogous to the situation we observed on transmission of HCV where the acute form evolves into the persistent form but re-infection involves the acute form of HCV. This parallel may have implications for the cultivation of HCV suggesting that different forms may require different culture conditions.

Given our observation that a parallel pattern of selection of variant types during HCV transmission suggest that the persistent form of HCV is not optimal for establishing an acute infection and thus variant forms must arise to establish the infection but that the HCV-PI form must replace this form to establish a life-long persistent. This suggests that specific biological features of E2 are necessary early in infection that are different from those functions that provide for persistent infection.

It is possible that HCV virus PI virus is like-wise not optimal of establishment and thus evolution of the receptor to affect its biology is required initially but on seroconversion that mutations that make the neutrallization epitopes more host like, becoming similar to IgG variable region, are selected that result in both neutralization escape as well as avoiding further recognition due to tolerance mechanisms that prevent its recognition. It is thus possible to maintain replicative abilities and at the same time hide from the immune system through antigenic mimicry with tolerant antigens.

The findings of the present invention will be further applied to the study and characterization of HIV infection. It is contemplated that the strategy of molecular mimicry as herein disclosed will provide a platform for analyzing the progression of HIV infection, and allow for the development of novel methods of characterizing, detecting and treating human immunodeficiency virus (HIV).

EXAMPLE III

Molecular Mimicry by HTLV-I/II

Human T-Lymphotropic virus type I (HTLV-I) was the first human retrovirus isolated in 1980 and is known to cause adult T-cell leukemia/lymphoma, and tropical spastic paraparesis/HTLV-I associated myelopathy (TSP/HAM) (Poiesz, B. J. *Proc. Natl. Acad. Sci. U.S.A* 77, 7415-7419 (1980). This retrovirus can be transmitted through blood transfusion, sexual activity, mother-to-child transmission, and intravenous drug abuse. HTLV type II (HTLV-II) is a closely related retrovirus, isolated in 1982, having similar structural features, antigenic properties, genomic organization and pathogenicity to HTLV-I (Chen et al. *Nature* 305, 502-505 (1983); Rosenblatt et al. *Leukemia* 6 Suppl 1, 18-23 (1992); Thorstensson et al. *Transfusion* 42, 780-791 (2002)).

Figure 11:
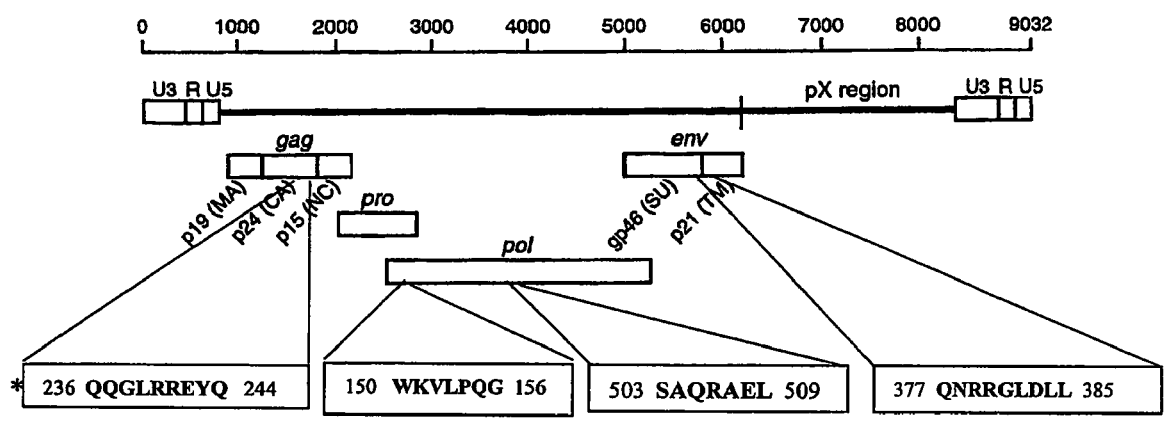
FIG. 11 illustrates HPDSEs within different regions of HTLV-I polyproteins gag (SEQ ID NO: 248), pol (SEQ ID NOS 249-250, respectively, in order of appearance) and env (SEQ ID NO: 251), according to an embodiment of the present invention. The highest homologous HPDSEs within different regions of HTLV-I polyproteins (gag-pol-env). * In the boxes, identical amino acids and their number positions in each protein are shown.

In accordance with the present invention, the role of molecular mimicry by HTLV-I was investigated as herein described. As illustrated in Tables 5A, 5B, and 5C, many host protein domains sequence elements (HPDSE) were identified within different regions of HTLV-I polyprotein sequences. More specifically, these HPDSEs were identified to be of human origin, including human endogenous retroviral (HERV) protein domains, thus indicating that HTLV-I has the potential to participate in molecular mimicry in humans in vivo. Table 5D and FIG. 11 exemplify HPDSEs of HTLV-I polyproteins gag, pol and env having a degree of homology to endogenous host elements, namely HERV elements.

Analysis of HPDSE overlapping and non-overlapping regions were carried out by a combination of Blast search programs, the FASTA, Ssearch programs in websites and MegAlign program in DNASTAR package. However, other such search vehicles may be employed in accordance with the present invention.

Our data show that the HTLV-I gag protein has more HPDSEs than the HIV gag protein (FIG. 12). In comparison with the other viruses, both HIV and HTLV have more HPDSEs in their structural and non-structural proteins thus, further suggesting that molecular mimicry plays a role in the persistence of HIV and HTLV infections. According to one embodiment of the present invention, the HTLV-1 gag protein may be used as a marker for characterizing a HTLV-I infection. For example, a HTLV-I gag protein having a predetermined number of HPDSEs may be indicative of a predisposition for pathogenicity or the propensity to induce a particular disease state. According to yet another embodiment of the present invention, HPDSEs of HTLV-I can be employed in the development and application of novel detection and treatment regimes for HTVL-I infection.

All human beings carry human endogenous retroviral (HERV) elements as an integral part of their genomes where 1-5% of the human genome contains HERV sequences. Although most HERV gene families are defective, some of them are actively transcribed, and proteins as well as virus-like particles have been observed and this produces potentially cross-reaction antigens. In blood donors auto-antibodies against HERV were detected at a frequency of 3% that may react with HTLV-I/II antigens and cause false positives. On the other hand existence of HERV elements in the human genome can also cause immune tolerance and will increase the rate of false negatives and may also contribute to the maintenance of persistent infection and disease. Many blood donors are deferred every year in Canada due to false positive reactions, even though they are truly negatives. This causes significant blood donor loss and promotes confusion and anxiety. In addition, there is a high risk of infections with HTLV-I/II through the blood transfusion due to the occurrence of false negatives.

The current diagnosis of HTLV-I/II infection is mainly based on ELISAs screening for antibodies and confirmation by the Western blot (WB) and both tests have problem with high rates of false positive and negative results. Of particular concern is increasing the incidence of HTLV-I infection world wide, especially in Western Europe, United States and Canada.

FIGS. 13, 14, and 15 illustrate HPDSEs identified within the gag, pol and env polyproteins of HTLV-I, respectively. In accordance with the present invention, the development of a new generation of serological tests is proposed comprising of new recombinant capture antigens based on the sequences deduced from non-HPDSEs-regions of HTLV polyproteins, as exemplified in FIGS. 13, 14, and 15. Capture antigens of the present invention may be produced by methods known in the art, or as otherwise herein described. According to one embodiment of the present invention, new recombinant capture antigens may be produced in insect cells using the Baculovirus expression system. Furthermore, synthetic peptides can be produced by methods known in the art to provide the capture antigens of the present invention. The new recombinant or synthetic peptide antigens would be more specific and sensitive for detection of HTLV-I/II antibodies and will reduce the false positive and negative rates in blood screening. In this regard, a molecular mimicry analysis can be applied to the development of new antigens to resolve the problems of inaccuracy of HTLV-I/II serological tests and reduce deferral of blood donors due to false positive reactions of HTLV-I or II. In addition, the high risk of infections with HTLV-I/II through the blood transfusion due to the false negatives will be reduced.

Furthermore, the identification of HPDSEs in variants of HTLV-I/II also provides a platform for the development of novel treatment regimes for such infections, as described hereinabove.

EXAMPLE IV

Molecular Mimicry and SARS-CoV

A novel coronavirus, SARS-CoV, has been identified as the causative agent of severe acute respiratory syndrome (SARS). For the purposes of the present invention, SARS-CoV is intended to include SARS-HCoV. Examination of, the SARS-CoV genomic sequence underscores its unknown origins, representing a new genetic lineage with limited sequence homology to known coronaviruses. Although the SARS-CoV genome sequence defines its biology and carries vestiges of its natural history, it is currently not possible to interpret viral host origins or biology, a priori from genomic sequence. We tested the hypothesis that coronaviruses employ a strategy of molecular mimicry during the process of adaptation in a given host. Furthermore, we reason, as further described in accordance with the present invention, that RNA viruses through their high mutability not only have the opportunity to mimic host structures, but also the motive as thereby they gain a selective advantage in the reactive host environment.

In accordance with an embodiment of the present invention, we found that SARS-CoV proteins possess host protein domain sequence elements (HPDSEs) that are comparable to the levels seen for human coronaviruses, suggesting a common evolutionary history of SARS-CoV with humans or primates as well as rodents and a broad host range experience. This means that viruses evolve to match themselves to their hosts by elaborating HPDSEs that have direct implications to infection and detection and treatment of disease as described herein. In addition, we found that SARS-CoV has acquired a highly homologous protein domain or HPDSE of the bacterial Peyer's Patches virulence factor, gipA from invasive bacteria which is known to be a natural pathogen of humans (FIG. 16). Similar to the demonstrated role of gipA in establishing systemic infection, we predict that SARS-CoV also employs this factor to achieve its enteric tropism and ability to establish systematic infections.

Evidence that SARS-CoV has a human-like history suggests that this virus may have arisen in humans, or if from a foreign host, could readily enter the human population again from its natural source. In addition, the possession of a bacterial virulence factor domain, herein identified as a HPDSE, may help explain the unusual severity of SARS infection in humans.

To assess the extent of molecular mimicry as a characteristic of RNA virus evolution, we analyzed functional protein domains and motifs existing in the major viral surface protein receptor S and replicase ORF1a (encoding RNA replication proteins) of known coronaviruses and SARS-CoV by using sequence alignment with the human proteome, as discussed further hereinbelow. We found that there were host protein domain sequence elements (HPDSEs) in SARS-CoV that were comparable or exceeded those in the other representative human and mouse coronaviruses, suggesting that SARS-CoV has a significant history of evolution in human or human-like species. Surprisingly, in broad searches of homology, SARS-CoV was also found to have a protein domain homologue or HPDSE, of the bacterial Peyer's Patch virulence factor, gipA, within the S protein that may be involved in the enteric tropism and severity of SARS. For the purposes of the present invention, this protein domain homologue is considered a HPDSE as gipA is a component of micro-organisms naturally found living within humans, and thus constitute part of the host. According to one embodiment of the present invention, genes of organisms harbored within hosts are included with host genes for the purposes of HPDSEs.

Based on these findings, the molecular mimicry strategy of the present invention has promising applications in the development of novel diagnostic and therapeutic protocols for detecting and treating SARS-CoV infection, including but not limited to those applications as, herein described. This knowledge of the evolutionary history of SARS-CoV provides important insight into the development of effective treatment regimes to combat this virus. The correlation of SARS-CoV virulence with the presence of a bacterial Peyer's Patches virulence factor provides a key target for such a treatment regime. For example, the identification of a bacterial Peyer's Patches virulence factor, gipA in SARS-CoV may serve as a target for a novel therapeutic compound having the ability to attenuate or disable the virulence factor and thereby slow or inhibit the progress of the infection. Furthermore, novel capture agents can be strategically prepared as described in accordance with the present invention to be devoid of a predetermined HPDSE, such as the sequence elements within the region of a bacterial Peyer's Patches virulence factor, to more accurately target SARS-CoV variants in a host. As discussed further hereinabove, such capture agents can be employed in assays for detecting a SARS-CoV variant in a test sample. In this regard, an effective diagnostic kit for convenient and effective detection of a SARS-CoV variant in a test sample is encompassed by the present invention. The identification of HPDSEs in SARS-CoV indicates that the potential pathogenicity of a virus to a given host can be assessed by analysis of its HPDSE. This will aid in the future identification and characterization of viral and microbial pathogens that can be found in nature.

SARS-CoV is a newly emergent virus of unknown origin that was first identified to cause disease in humans in Guangdong province, China in November of 2002 (1;2). SARS-CoV possesses a unique combination of high virulence and an attack rate that allows it to cause alarming outbreaks of atypical pneumonia, particularly in hospital settings. Speculation regarding the origins of SARS-CoV has largely focused on introduction from animals, given that SARS CoV is a unique coronavirus that does not closely match any known members infecting humans and domestic animals (3). Coronaviruses (CoVs) generally have a narrow host range, infecting one or just a few species, an implication being that SARS-CoV has jumped a relatively discrete species barrier (4). On the other hand the recent isolation of SARS-CoV from the feces of several exotic animals, including Palm civets, in live animal markets in. China suggests that this virus has a broad host range (5;6) but cannot currently be interpreted as representing the identification of the source of SARS-CoV.

Within the first month of recognition of SARS as a novel entity, SARS-CoV was isolated in several affected countries including Canada where the full genome sequence of the Tor-2 isolate was determined (3). This was followed in rapid succession by genomic comparison among SARS-CoV isolates from patients inside China and abroad that provided a snapshot of a relatively slowly evolving pathogen (7). The isolates could be assigned to 2 groups that primarily differed by 4 mutations and that had accumulated over an indeterminate period within a 3 to 8 months span of independent evolution (twice the span from possible divergence in Guangdong). In contrast to the rapid evolution that is expected of a virus that has entered a new host, this was the amount of mutation that would be expected for a coronavirus in its natural host over this time period (predicted to be 5 to 14 mutations from the observed mutation rate for porcine transmissible gastroenteritis virus (TGEV) of $7\times10^{-4}$/nucleotide/year) (8). This suggests an alternate hypothesis for the origin of SARS CoV, as it raises the possibility that SARS CoV has a human-like origin or is a virus of multiple hosts including humans but that has gone undetected until mutating to increased virulence. Given the paucity of pertinent human surveillance, it is conceivable that unrecognized human CoVs exist, especially in less developed regions.

Coronaviruses are large, enveloped, positive-stranded RNA viruses that usually cause mild respiratory disease in humans and possibly enteric disease in children (4). Human coronaviruses, HCoV-229E and HCoV-OC43, are responsible for about 30% of mild upper respiratory tract illnesses. Although examination of the SARS-CoV genome demonstrates a typical CoV genome organization (9), the genome must possess features that are responsible for its unique biological properties. Some of these are expected to reside in the major surface protein, S, that contains important antigenic sites and is a key genetic determinant of virulence (10;11) and host tropism (12;13).

Figure 17A:
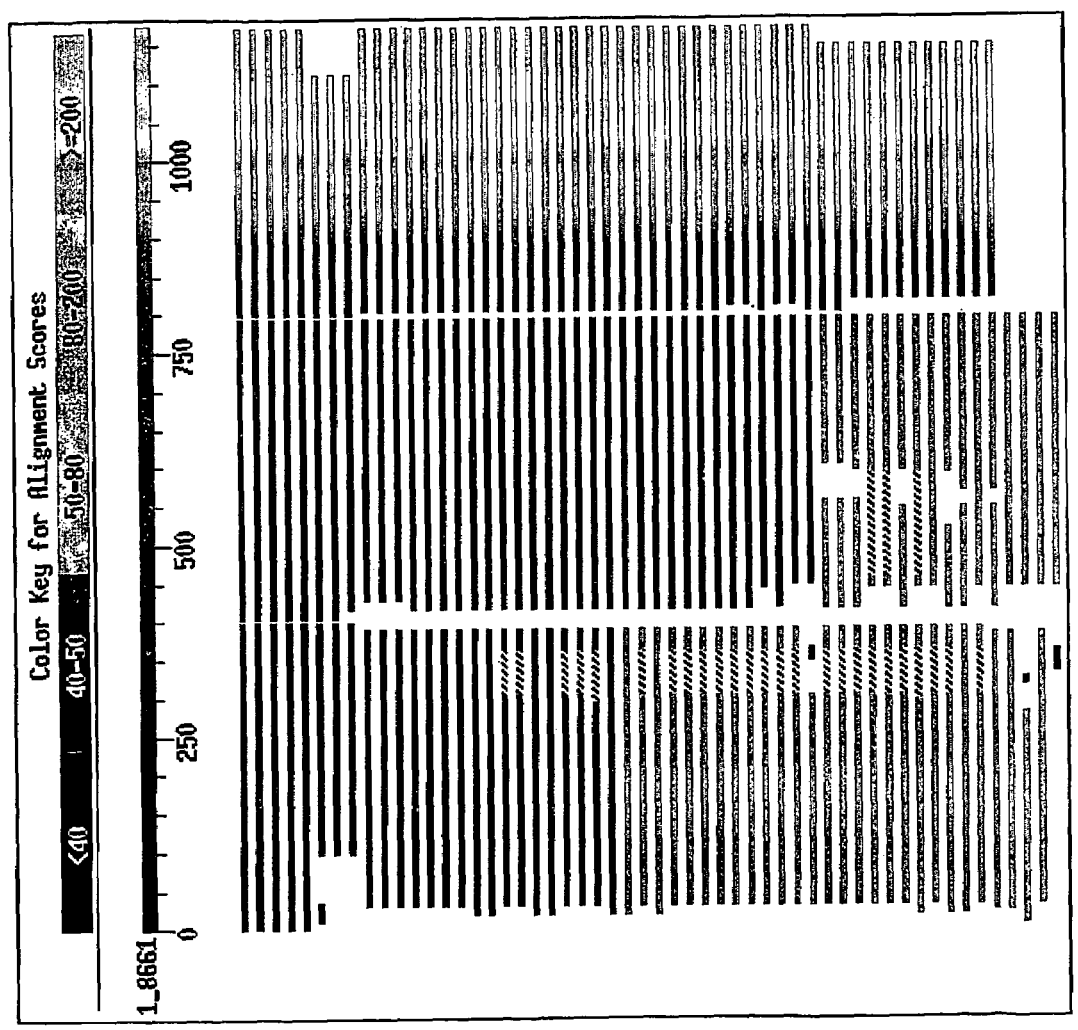
FIGS. 17A & 17B illustrate Blast distribution and alignment of amino acids in S protein for human coronaviruses 229E (A) and SARS-CoV (B) with homologous amino acid sequences available in GenBank, according to an embodiment of the present invention. Blast distribution and alignment of amino acids in S protein for human coronaviruses 229E (panel A) and SARS-CoV(panel B) with homologous amino acid sequences available in GenBank. The color-coded alignment scores indicate the length of homologous regions. HCoV-229E has high homology to coronaviruses in the same and other antigenic groups. The amino terminal end of SARS-CoV is highly divergent from all other known viruses except other SARS-CoV.
Figure 17B:
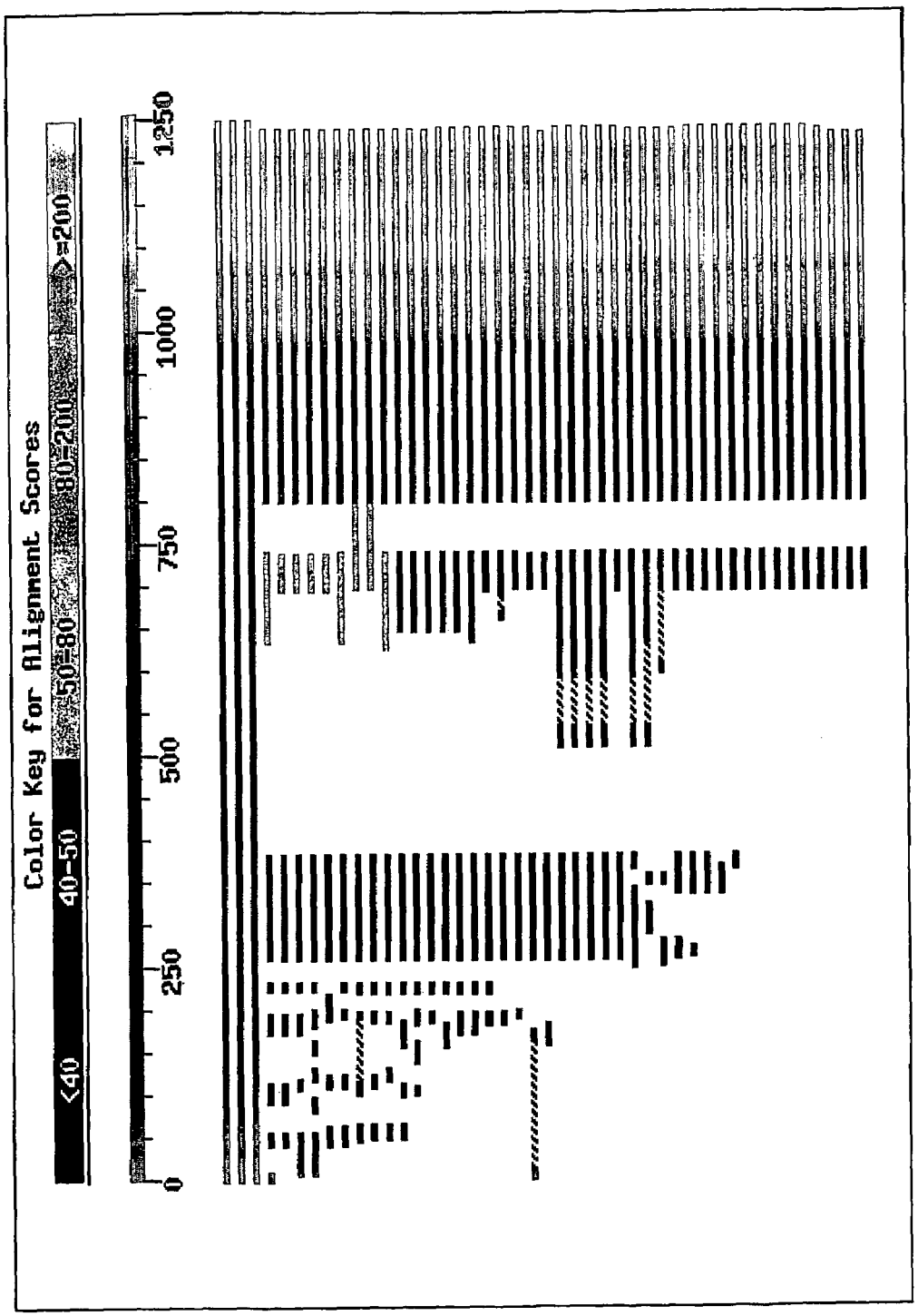

The discovery of sequence homology to a known protein or family of proteins often provides the first insights into the function of a novel gene sequence. Yet, the level of similarity between the predicted amino acid sequence of the S protein of SARS-CoV and other. CoVs is low (20-27% pair-wise amino acid identity (9) and therefore the comparison of primary amino acid sequences does not readily provide insight into the biological properties of the SARS-CoV S protein (FIGS. 17A & 17B). Also the CoV genetic map is largely incomplete, as most functions have not been ascribed to specific genetic regions or sequences (4). In addition to serving specific replicative functions viral proteins must also be of low immunogenicity, in their cognate host. As the host employs the immune response to limit and clear infections, viruses have evolved means of avoiding or inhibiting this response.

In contrast to large DNA viruses, which encode multiple proteins with dedicated functions, RNA viruses have smaller genomes (as larger size put them over the fatal error threshold into catastrophe) that possess overlapping genes and multifunctional proteins (23;24). Evolutionary analysis of RNA viruses is therefore confounded by extreme genetic variation occurring at a rate of about $10^{-3}$ per nucleotide per year for synonymous sites and $10^{-5}$ for non-synonymous mutations that are under selective constraints (25). Such rapid evolution means that limited evolutionary relationships, can be analyzed (projected to be less than 50,000 years) but it does provide a rich genetic trail to follow. Since RNA viruses produce on average a single mutation per genome replication, a population of viruses that is four times genome length in nucleotides constitutes a pool of viruses comprised of all possible single nucleotide substitutions ($1.2\times10^5$ virions for coronaviruses); as individual mutations are the fodder of evolution, such a population size can be said to have reached the maximum diversity threshold (MDT). Viruses exist within hosts as large populations, well beyond MDT (typically $>10^7$ per gram tissue), constituting mutant swarms of variants, termed quasispecies that possess genomes centered around consensus sequences (26;27). As populations beyond MDT are comprised of genomes possessing all possible single nucleotide and amino acid substitutions, if any given single change can positively affect replication in the host it will be selected to eventually replace the population. Continuous reiteration of this process is therefore predicted to incrementally and progressively increase antigenic mimicry of host proteins. In keeping with this concept virus evolution is accelerated on entering a new host environment where new forces select novel variants to better fit the new host, as seen for HIV and influenza A viruses on entry into humans from primates and avians respectively (25). Experimental studies of rapid directed evolution in an alternate host includes the acquisition of optimizing mutations that allow interaction with specific host proteins required in replication (28;29). Viruses can also evolve to mimic host protein structure to avoid detection, as the immune system employs a process of antigenic recognition focused on the discrimination of foreign versus self antigens. In this regard the S protein of several CoVs infecting mice, cows, and pigs contain host Fc gamma receptor (Fc(R)) domains that are known to bind immunoglobulins and may play a role in pathogenesis (33). Three short homologous Fcγ receptor domains of 6-13 of amino acid were identified in the S protein of mouse hepatitis virus, (MHV) (34). Thus there are demonstrated instances of structural mimicry in RNA viruses including CoVs.

Methods

We compared the extent of molecular mimicry of SARS-CoV and prototype human and animal coronaviruses with the human and mouse genomes as well as all Genbank sequences using sequence alignment algorithms. Nucleotide sequences were then translated into amino acid sequences using the Translator-online tool found on the JustBio home page (http://www.justbio.com) and computer analyses of amino acid sequence homologies were performed using the online database BLAST (Basic Local Alignment Search Tool) program found on the. NCBI (National Center for Biotechnology Information) home page (http://www.ncbi.nlm.nih.gov) as well as the SSEARCH program on the NPS@ (Network Protein Sequence @nalysis) home page (http://npsa-pbil.ib-cp.fr). All further sequence analyses and comparisons were performed using the DNA-STAR Lasergene '99 software package (DNAStar; Madison, Wis.). We analyzed coronaviruses that infect different hosts including, human (HCoV 229E, HCoV OC43), mouse (MHV), bovine (BCoV) and chicken (IBV) (representing members of all 3 known antigenic groups) as well as SARS-CoV (isolates Tor-2 and CUHK-W1)); accession numbers for these genes are shown in Table 6.

Results and Discussion

SARS-CoV S Sequence Variation

First, to better understand the evolutionary relationships of SARS-CoV to other members of the Coronaviridae, we analyzed the amino acid sequence similarity to different regions of the S protein of all CoVs as well as all other known sequences available in the GenBank database using alignment algorithms (FIG. 17A, Table 6). This yields protein alignment scores as E values, representing the chance probability of obtaining a given homologous sequence from a given data set and where E=0 indicates identity. Using genomic data sets, E values between 1 and 10 are usually related and values less than 0.01 almost always represent homologous proteins (35;36). The surface protein, S, is composed of a large N terminal ectodomain comprised of 2 sub-units, S1 plus S2, that is anchored in the membrane with a short carboxyl-terminal cytoplasmic domain (37). We found that the N-terminal sequence of S1 (1-800 aa) of SARS-CoVs, is extremely divergent and thus significantly distinct from other CoVs. In particular, within the first 250 aa of the S protein, the similarity between SARS-CoVs and other CoVs is as low as to appear unrelated (E value>10) (FIG. 17B). This region of S has been shown to be hypervariable within as well as among CoVs (38;39). SARS-CoV homology to non-CoV sequences was seen in this region and will be presented later. Sequence conservation seen as similarity of SARS-CoV to other CoVs could be detected from aa 250-800 of S protein of SARS-Co-V when performing sequential searches using small stretches of 200-250 aa that optimizes alignment algorithm performance. The similarity between SARS-CoVs and other CoVs varied, ranging from a low level (E=9.8) for Porcine CoV, up to very high (E=5e-18) for rat CoV S proteins. The C-terminal region primarily comprising S2, from aa 800-1250, was relatively conserved with homologies ranging from 33% to 54% aa identity to the corresponding region of other CoVs (E value from 8e-10 to e-50). SARS-CoV S protein is most closely related to the rodent and bovine lineages (MHV and BCoV) of antigenic group II (9).

Human Protein Domains in Coronaviruses

Figure 18:
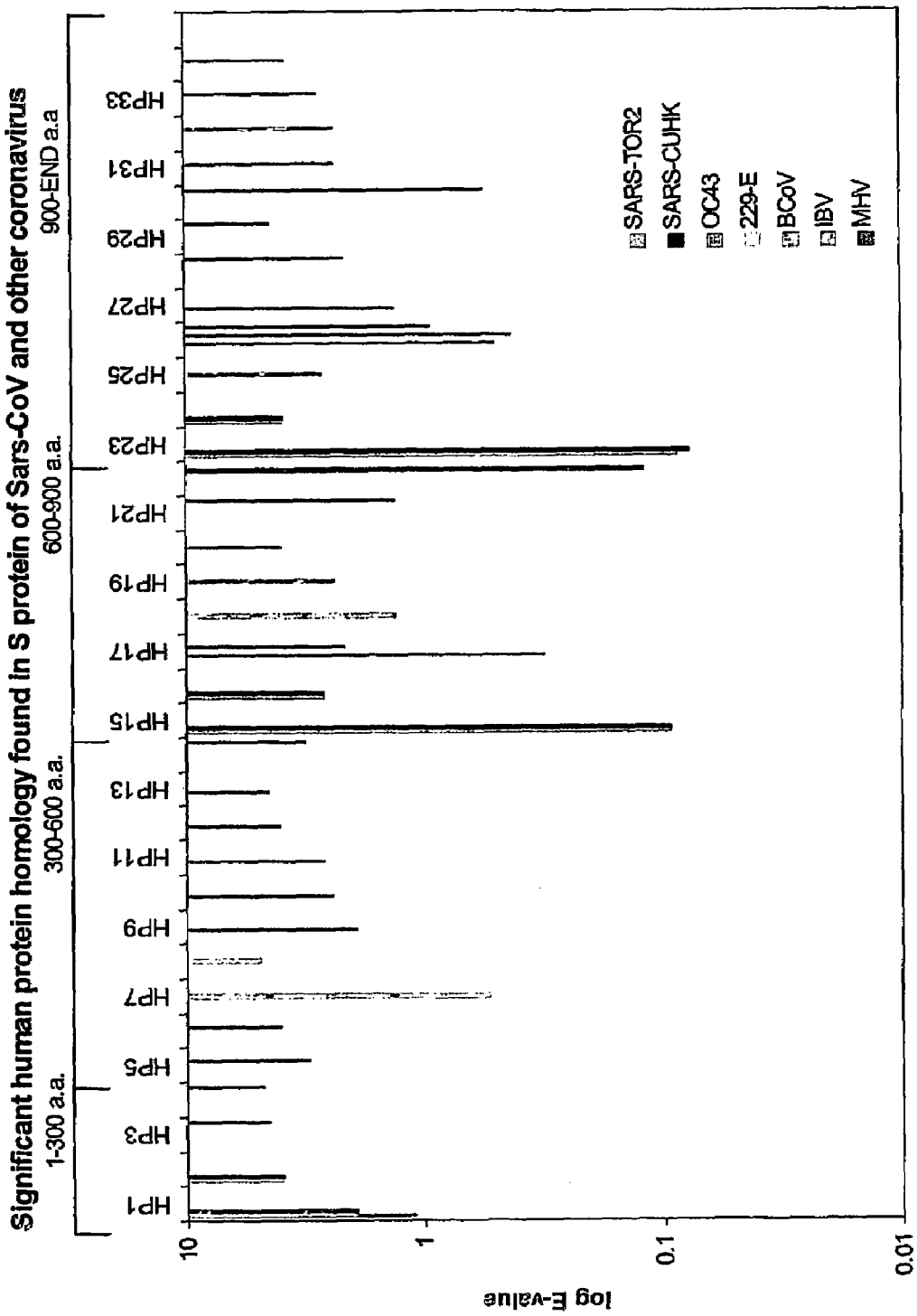
FIG. 18 illustrates HPDSEs identified in S protein of SARS-CoV and other coronaviruses having significant protein homology with human proteins (as identified in Table 7), according to an embodiment of the present invention. Significant human protein homology found in S protein of Sars-CoV and other coronavirus. Significant protein homology found in S protein of SARS-CoV in human proteins (corresponding host proteins identified in Table 7).

We found a virus-host relationship when we compared the protein homology of CoVs of known host origin to protein sequences of the human proteome. Proteins evolve at different rates dependent on their functional constraints thus constituting molecular clocks (40). In coronaviruse the RNA replicase proteins are highly conserved allowing comparisons over longer time spans, whereas the highly variable S protein changes more rapidly and thus varies within shorter time frames and where distant events are obscured. To begin to assess the relative amount, of human genome homology, sequential 300 amino acid portions of the S gene were compared to the human protein database. In general the extent of homology was relatively low which may reflect the high variability of the S protein. At the lower level of significance (E value>2.0) HPDSEs were found to correspond to regions within the S protein of all CoVs (FIG. 18, see Table 7 for protein legend). In contrast maximal homology was found for SARS CoV and multiple instances of high human protein domain homology was also seen for the human and mouse strains that differed from the IBV and BCoV animal strains that each possessed one domain near this level. Overall, the number and degree of homology of HPDs was higher in SARS-CoV and human CoVs than in animal CoVs. This suggests that SARS is as human-like as human coronavirus with respect to host structural mimicry of the highly variable surface protein.

We used the same approach to analyze the ORF1a replicase polyprotein required for RNA synthesis of CoVs. Comparisons of 1000 aa blocks of ORF1a from representative CoVs, were made with the human proteome (FIG. 19A, Table 8). Again, several HPDSEs with lower homology (E>0.1) were found in all CoVs (not shown), however very high homology HPDSE was identified in a 146 aa replicase region from 1034-1180 aa corresponding to a B aggressive lymphoma cDNA that bore the highest similarity to HCoV-229E (E values to 9e-07), followed by SARS-CoV and then MHV; no significant homology was seen for chicken or bovine CoV. Two other related human proteins had lesser homology to the same HPDSE in HCoV-229E but maintained high levels of homology to SARS-CoV and MHV. Presumably HCoV-229E had evolved towards the B aggressive lymphoma protein but not the 2 other divergent protein homologues (KIAA1268 and LRP16). Interestingly, SARS-CoV had the highest homology to these latter protein domains followed by human and murine viruses. This suggests that SARS is as human like as HCoV-229E but that murine coronavirus also has a close relationship with humans, which was not seen for bovine or chicken coronaviruses.

Figure 20A:
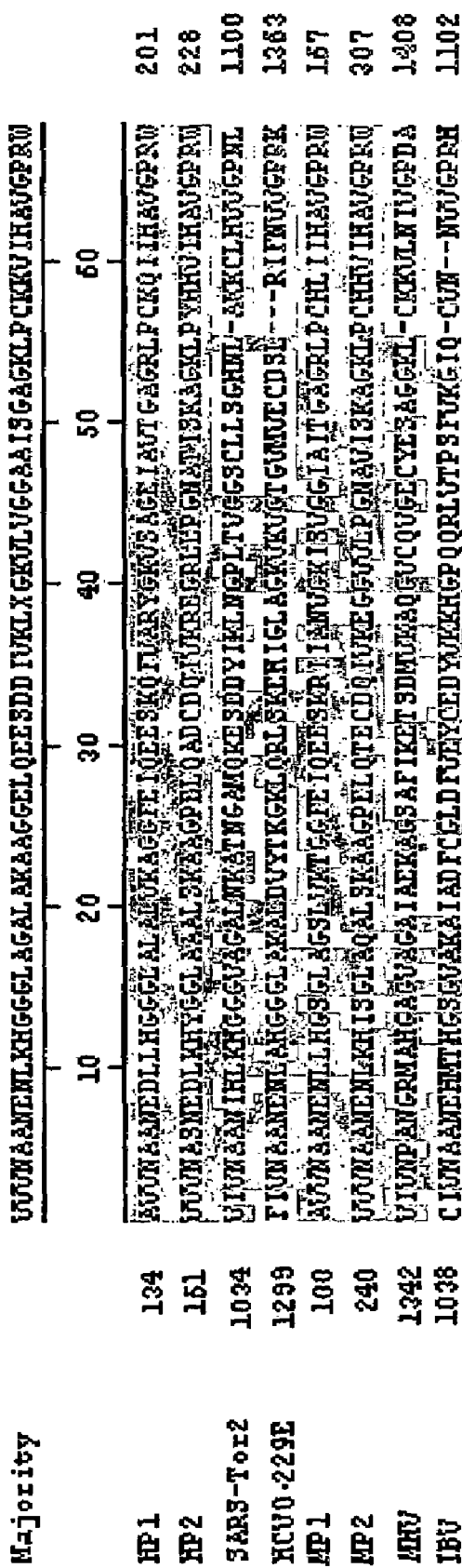
FIGS. 20A & 20B illustrate an alignment of human and mouse proteins with homologous regions from ORF1a from SARS-CoV and coronaviruses representing the 3 known antigenic groups (HCoV-229E, MHV, and IBV) (A) where sequence identity with the human proteins (HP1, HP2) is masked in yellow, and pair wise sequence comparisons (B), according to an embodiment of the present invention.
Figure 20B:
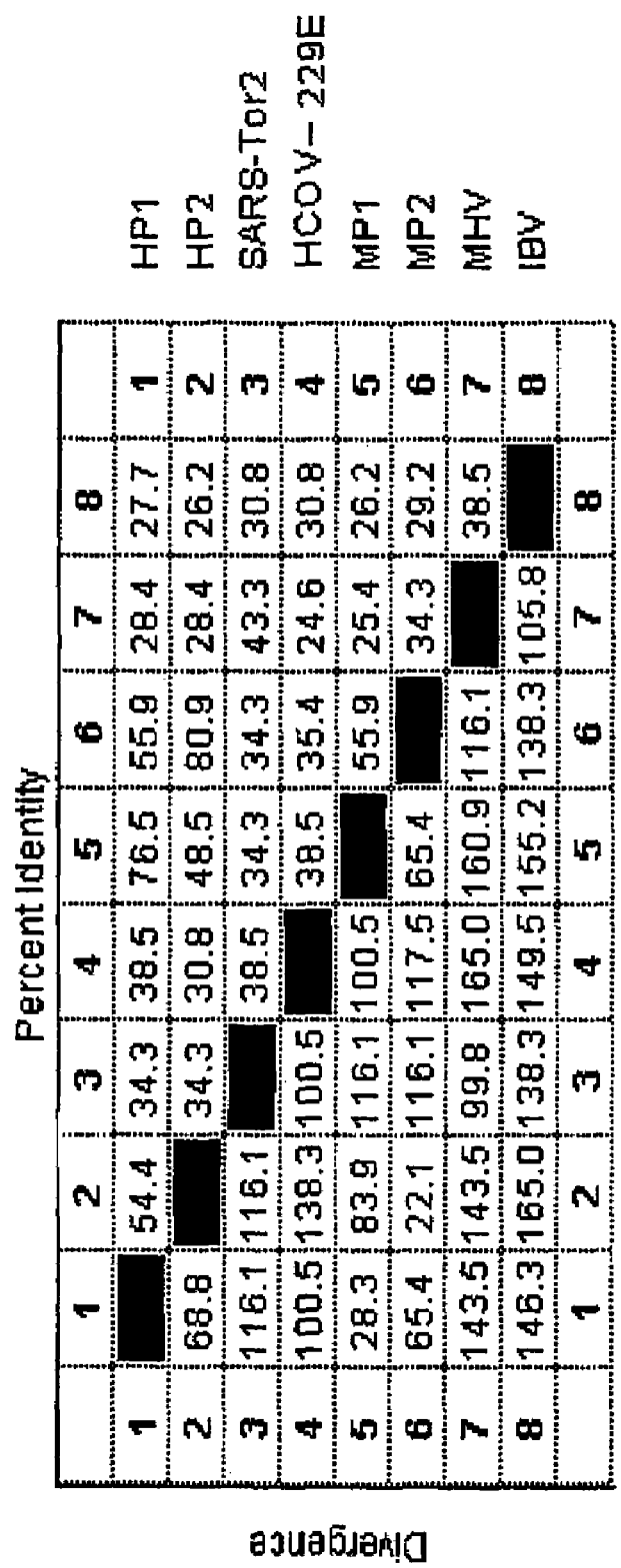

When we searched the mouse proteome for viral homology to mouse proteins using representatives of the four groups of CoVs we found homology to the corresponding mouse family of 3 related proteins, 2 of which (MP1, B aggressive lymphoma; and MP2, BAC40943.1) correspond to human proteins (E=0 for HP1, B aggressive lymphoma cDNA; and HP2, KIAA1268) (FIG. 19B, Table 8). In this instance the MHV replicase possessed the highest homology (E=8e-09) to MP2 followed by SARS CoV and then human CoV229E (FIG. 19B). Interestingly, although the human and mouse virus possessed similar homology to MP1 and MP2, SARS-CoV possessed the highest homology to these proteins. Again the extent of homology to HPDSE in CoVs of known origin was associated with their host of origin. Alignment of a 70 aa portion of homologous viral sequences with the mouse and human proteins shows SARS-CoV to possess 38.5% and 34.3% sequence homology to HP1 and 2 as well as 34.3% to both MP1 and 2 (FIG. 20A). These homologies were similar to those seen for MHV but were higher than those seen for IBV (ranging from 26.2 to 29.2%) (FIG. 20B). SARS-CoV possesses host genome homology that parallels human CoVs and suggests a human passage history that could also involve rodent transmission as high genome mimicry was also seen relative to the mouse genomes for both human and mouse viruses. The high shared homology of murine and human coronaviruses to both of their alternative hosts is consistent with the close phylogenic relationship between humans and rodents that have diverged relatively recently. The percent identity of pairs of sequences as illustrated in FIG. 20B shows SARS-CoV to be as human-like and as mouse-like as HCoV-229E. As illustrated, the divergence scores are proportional to mutational distance between sequences using the CLUSTAL program of DNA-STAR. As well the pattern of homology of SARS-CoVs to mice may reflect the distant genealogical relationship with the rodent viruses. (Rat and MHV) as well as the long history of human and rodent co-habitation which may have contributed to a sharing of viral pathogens including coronaviruses. Indeed rodent to human transmission is very common for bacteria (*Salmonella, Francisella, Yersinia*) and viruses (Monkeypox, Arenaviruses, Bunyaviruses). Therefore we conclude that SARS-CoV is of human or primate origins but that it may have common history with multiple mammalian species that extends beyond the observed infection of cat-like animals to possibly include their prey, rodents. This grouping of hosts constitutes both a confluence of cohabiting organism but as well a group of foods as both rodents, cats in addition to nonhuman primates are consumed by humans in southern China. Local culinary practices that include the butchering and eating of wild caught animals could also promote transmission of their resident viruses to humans.

SARS-CoV S Protein Possesses a Bacterial Virulence Factor Domain

Another important question relates to the basis for the high virulence of SARS-CoV. In contrast to the upper respiratory infections due to typical human CoVs the pattern of SARS disease symptoms and virus isolation indicates infection of both the lower respiratory and gastro enteric tracts (41). In an assessment of clinical progression of 75 patients with SARS, patients initially possessed signs of respiratory infection that included abnormal radiological signs in individual lung lobes. One week after onset of symptoms, most patients developed watery diarrhea coincident with a worsening of radiological findings and respiratory sysmptoms and a high incidence of acute respiratory distress syndrome (ARDS, in 15 of 18 patients) requiring mechanical ventilation. Peak virus titres in nasal secretions are seen around the time of onset of diarrhea where virus was shed in feces for several weeks.

This pattern of disease indicates that SARS is not only pneumotropic attacking the lungs but that there is subsequent spread of infection to the enteric tract, leading to diarrhea concomitant with spread throughout the lung. SARS infection is systemic as virus was also present in blood (42) and urine (41). SARS CoV may be more able to reach or enter and colonize the gastro enteric tract than typical human CoV. Most animal CoVs have dual tropism being able to replicate in the respiratory and enteric tracts. Interestingly the HCoV-OC43, that is very similar to BCoV and may represent a recent introduction from animals, has also been reported to be shed in feces in children and been associated with systemic infection (4). Several viruses enter into the circulation through specialized lymphoid organs called Peyer's Patches that exist in the lumen of the respiratory and enteric tract as seen for enteroviruses, Reovirus, and HIV (43). Specialized epithelial cells called microfold epithelial cells (M) overlay Peyer's Patches and function to sample molecules and particles for presentation to lymphoid cells within Peyer's Patches. Fecal-oral transmission has been implicated in the dissemination of SARS-CoV during a large outbreak in a Hong Kong apartment complex (41).

Figure 21:
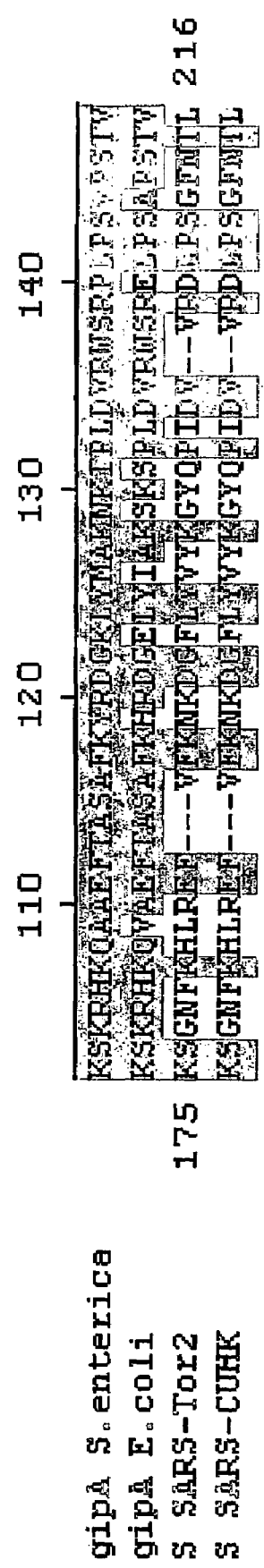
FIG. 21 illustrates an alignment of Peyer's Patches virulence factors gipA of invasive bacteria with a homologous domain in S protein of different SARS-CoVs according to an embodiment of the present invention (SEQ ID NOS 331-334, respectively, in order of appearance). Alignment of Peyer's patches virulence factors gipA of invasive bacteria with a homologous domain in S protein of different SARS-CoVs. Amino acid identity with Salmonella gipA is indicated by gray.

As viral surface proteins are invariably involved in tropism and spread we focused on S protein structure to derive biological clues to its role in virulence. The variable S1 subunit comprises the N-terminal half of S (see FIG. 17), and is responsible for binding to specific receptors on the membranes of susceptible cells. Variation in S1 is associated with altered antigenicity and pathogenicity (8). Other biological activities have also been associated with the S1 subunit such as the Fcγ receptor for immunoglobulin, mentioned earlier. To gain insight into the genetic structure of SARS-CoV, we assessed the existence of other protein homology domains in S, we searched all gene sequences available in BanBank using a combination of DNA STAR and web-based NCBI programs. Surprisingly, the highest homology SARS-CoV S protein domain was shared with pathogenicity factor, gipA, a Peyer's Patches virulence factor from invasive *E. coli* CFT073 (44) and *Salmonella enterica* serovar typhimurium (45) and (FIG. 21). The 376 amino acid gipA protein as characterized in *Salmonella* is a protein encoded in the lysogenic lambdoid phage, Gifsy-1, that is only expressed in the intestine where it enhances virulence by increasing the ability of *Salmonella* to grow and survive in Peyer's patch and cause systemic disease. The gipA domain of S protein is located at aa position 177-213 corresponding to gipA aa 102 to 143. All SARS-CoV strains have the same gipA homology (aa identity 45%, 19/45), which is much higher than that predicted by chance (5%).

Figure 22:
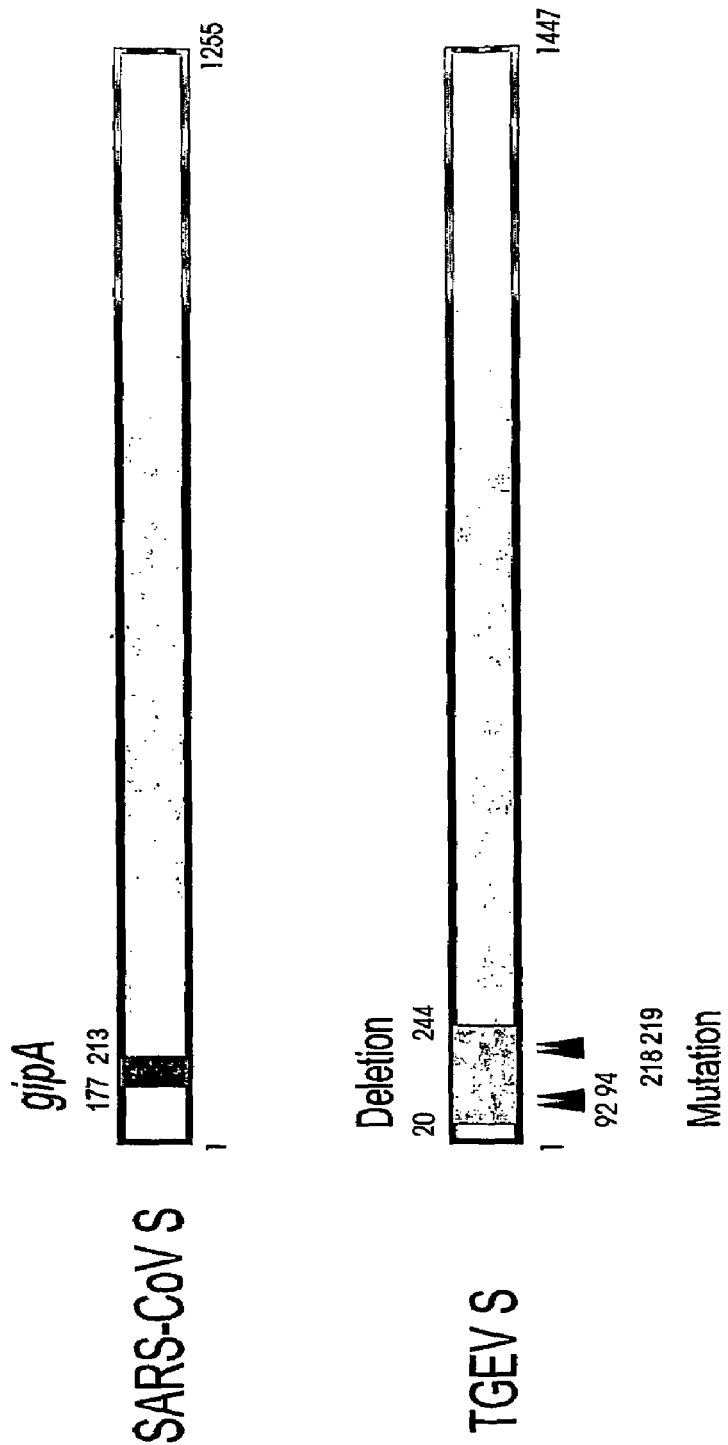
FIG. 22 illustrates concurrence of locations of the enterotropism determining element in porcine TGEV and the major gipA homology domain of SARS-CoV, according to an embodiment of the present invention. Concurrence of locations of the enterotropism determining element in porcine TGEV and the major gipA homology domain of SARS-CoV. The location of deletion and mutations (shown with arrows) causing loss of enterotropism in TGEV.

When the SARS-CoV sequence was aligned with the consensus sequence of gipA and its homologous gene family, comprised of bacterial transposases, the homology rose to 54.5% (not shown). The SARS-CoV-gipA homology was higher than that seen for the transposase genes suggesting that SARS-CoV S is more likely to possess the virulence function than the transposition function. The sequence alignment of S and gipA indicates that 28% amino acids (105/376) of gipA are identical and align in a mosaic pattern to matched sequences of SARS-CoV S. In comparison to SARS-CoV, the percentage of identical sequence between gipA and S of other CoVs was much lower, (e.g. down to 15% in IBV) but which also suggests a significant homology (data not shown). Although the major SARS gipA domain was not found in other known CoVs, the same region of S1 has been mapped to the control of enterotropism in porcine transmissible gastroenteritis virus (TGEV). Naturally occurring TGEV variants that have lost enterotropism and are restricted to infection of the respiratory tract have a deletion of this region (that has been genetically confirmed to control enterotropism) and other respiratory variants that are not deleted have mutations in this region (8) (FIG. 22). The occurrence of the gipA virulence factor domain at a position corresponding to the porcine enterotropism controlling element, further supports a proposed role in enterotropism and virulence of SARS-CoV. It is also possible to speculate that pre-existing antibody to uropathogenic E. coli CFT073 or Salmonella typhimurium that occurs commonly in some human populations, may provide cross-protection against SARS-CoV as the gipA domain resides in a location corresponding to 2 antibody binding sites in TGEV (8;46) that also overlaps with a sialic acid binding domain (37;47;48). Regional differences in the existence of cross-reactive immunity in various human populations could help explain the observed differences in disease severity and transmission observed in different geographic regions. The existence of a bacterial gene homologue in a eukaryotic virus represents another example of lateral gene transfer between prokaryotes and eukaryotes, as reported for 40 other genes in the human genome (49). Coronaviruse have demonstrated abilities to recombine with other CoVs as well as transduce genes from other viruses types which infect the same tissues and may now include viruses of bacteria (37). Further experiments are needed to determine the significance of the gipA protein domain in the observed severity of SARS.

We conclude that the SARS-CoV genome possesses evidence of adaptation to human-like and rodent-like hosts as well as the acquisition of a HPDSE having homology to a bacterial virulence factor. Consistent with its broad host range, such adaptation may have allowed SARS-CoV to directly enter the human host without the need for extensive adaptive events or alternatively that SARS-CoV is a variant of a human coronavirus.

The embodiment(s) of the invention described above is(are) intended to be exemplary only. The scope of the invention is therefore intended to be limited solely by the scope of the appended claims.

The references listed below as well as all references cited in the specification are incorporated herein by reference to the extent that they supplement, explain, provided a background for or teach methodology, techniques and/or compositions employed herein.

TABLE 1

Amino acid sequence homology between human Ig-V protein domains and the N-terminal E2 region from eight different genotypes of HCV

| Genotype (Acc. #)* | Protein (Acc. #)** | Protein (source) | No. aa overlap | Homology Z-score | Identity % |
|---|---|---|---|---|---|
| 1a (S1 strain) |  | IgG (Human) | 62 (397-459) | 105.7 | 26.32 |
| 1b (A1F333324) | 1c5d | IgG (human) | 130 (397-526) | 111.4 | 25.38 |
| 2a (AF238485) | 1fvd | IgG (human) | 81 (443-523) | 140.0 | 38.72 |
| 2b (AF238486) | 2rcs | IgG (human) | 86 (438-523) | 116.9 | 30.23 |
| 3a (D28917) | 1yuh | IgG (mouse) | 101 (461-561) | 105.9 | 23.76 |
| 3b (D49374) | 1dgd | IgG (human) | 187 (395-570) | 121.9 | 23.24 |
| 4a (Y11604) | 1c5d | IgG (human) | 110 (416-526) | 129.6 | 30.00 |
| 5a (Y13184) | 2fbj | IgA (human) | 163 (506-669) | 111.2 | 23.31 |
| 6a (Y12038) | 1yuh | IgG (mouse) | 124 (454-578) | 110.2 | 24.19 |

Data base access numbers are indicated for protein sequences analyzed using NCBI (*) and SSEARCH (**).

TABLE 2

Amino acid homology between germline antibodies and all known virus proteins in GenBank detected by NCBI Blast

| Antibody | Viral protein (No. of sequences found) | Degree of homology Identity (overlap aa) | E value |
|---|---|---|---|
| 2rcs | HCV E2 polyprotein (58) | 28-34% (436-514) | 0.50-0.044 |
|  | Herpes virus 6 glycoprotein (3) | 21% | 5.20-0.85 |
| 1gaf | HCV E2 polyprotein (67) | 28-34% (436-514) | 0.49-0.018 |
|  | Herpes virus 6 glycoprotein (3) | 21% | 4.90-0.87 |

TABLE 3

Genetic and biological characteristics of HCV variants and their homology to IgVL

| Variant | Identity to IgVL (aa) | | Proportion of various variants (%) | | | | |
|---|---|---|---|---|---|---|---|
|  | HVR1 (%) | E2 %) | A1 | A2 | A3 | A4 | A5 |
| IFN-Resistant | 35.0 | 39.3 | 3.6 | 8.3 | 0.0 | 90.0 | 30.0 |
| Antibody escape | ≧35.0 | ≧40.3 | 39.3 | 45.8 | 100.0 | 0.0 | 70.0 |
| Antibody neutralized | 30.0 | 37.8 | 21.4 | 4.2 | 0.0 | 10.0 | 0.0 |
| Others |  |  | 35.7 | 41.7 | 0.0 | 0.0 | 0.0 |

A1: Before seroconversion; A2, early seroconversion; A3, four weeks after seroconversion; A4, four weeks after IFN treatment; A5, nine weeks after IFN treatment.

TABLE 4

Proteins domain (s) with the sequence homologous to E1/E2 domain sequence of HCV quasispecies during acute and chronic phase of infection

| Isolate | Direct/clones | Proteins displayed | (source) | No. aa overlap (region) | No. displayed sequences (Z-score) |
|---|---|---|---|---|---|
| A1 | Direct* | membrane protein | (E. Coli) | 104 (348-452) | 2 (112.6) |
|  | -5 | immunoglobulin | (human) | 57 (406-462) | 2 (106.9) |
|  | -6 | bactericidal | (human) | 127 (393-467) | 2 (113.3) |
|  |  | membrane protein | (E. Coli) | 102 (348-450) | 2 (104.5) |
|  | -7 | hydrolase | (virus) | 160 (345-490) | 1 (104.7) |
|  | -8 | membrane protein | (E. Coli) | 102 (348-450) | 2 (105.3) |
|  | -12 | hydrolase | (virus) | 160 (346-490) | 2 (107.8) |
|  | -14 | molybdate protein | (E. Coli) | 62 (388-450) | 2 (106.4) |
|  | -15 | hydrolase | (fungi) | 170 (335-490) | 2 (110.2) |
|  | -16 | hydrolase | (bacillus) | 133 (357-489) | 4 (110.2) |
|  | -19 | bactericidal | (human) | 127 (339-465) | 2 (107.1) |
| A2 | Direct | membrane protein | (E. Coli) | 104 (348-452) | 2 (112.6) |
|  | -1 | metalloprotease | (bacteria) | 68 (439-486) | 1 (115.3) |
|  | -7 | membrane protein | (E. Coli) | 102 (348-450) | 2 (107.9) |
|  | -8 | coat protein | (phage) | 69 (339-407) | 1 (108.7) |
|  | -9 | hydrolase | (fungi) | 115 (363-477) | 2 (104.1) |
|  | -11 | metalloprotease | (bacteria) | 68 (439-486) | 1 (107.5) |
|  | -12 | bactericidal | (human) | 147 (340-486) | 2 (113.3) |
|  | -13 | bactericidal | (human) | 122 (339-460) | 2 (108.4) |
| A3 | Direct | bactericidal | (human) | 122 (339-460) | 2 (111.5) |
|  |  | immunoglobulin | (human) | 87 (406-492) | 2 (106.9) |
|  | -4 | bactericidal | (human) | 122 (339-460) | 2 (117.8) |
|  | -5 | metalloprotease | (human) | 68 (439-486) | 1 (106.0) |
|  | -6 | bactericidal | (human) | 122 (339-460) | 2 (104.9) |
|  | -8 | bactericidal | (human) | 122 (339-460) | 2 (104.9) |
|  | -9 | bactericidal | (human) | 122 (339-460) | 2 (106.6) |
| S1 | Direct | bactericidal | (human) | 122 (340-462) | 2 (112.6) |
|  |  | mmunoglobulin | (human) | 87 (406-492) | 4 (109.0) |
|  | -2 | bactericidal | (human) | 122 (339-460) | 2 (106.6) |
|  | -7 | bactericidal | (human) | 122 (339-460) | 2 (125.3) |
|  |  | immunoglobulin | (human) | 57 (406-462) | 1 (104.3) |
|  | -8 | bactericidal | (human) | 122 (339-460) | 2 (106.1) |
|  | -11 | membrane protein | (E. Coli) | 102 (348-450) | 2 (107.0) |
|  | -12 | bactericidal | (human) | 122 (339-460) | 2 (107.8) |
|  | -15 | bactericidal | (human) | 122 (339-460) | 2 (108.8) |
|  | -16 | immunoglobulin | (human) | 87 (406-492) | 2 (104.8) |

*Denotes that the sequences is from direct DNA sequencing.

TABLE 5A

HPDSEs in Gag protein of HTLV-I and the Accession numbers of corresponding host proteins in GenBank, Peptides disclosed as SEQ ID NOS 395-433, respectively, in order of appearance.

| Name of protein | Position of Protein | E-value | Accession Number |
|---|---|---|---|
| From a.a 1-300 |  |  |  |
| TPA:harmonin isoform 3 | 7 RSASPIPRPP 16 | 1.2 | DAA00086.1 |
|  | 11 PIPRPPRG 18 | ... | ... |
| unnamed protein product | 34 LEPGPS 39 | 1.6 | BAB15254.1 |
|  | 96 SR-PAPPP 102 | ... | ... |
|  | 98 PAPPPSS 105 | ... | ... |
| Serin arginine -rich pre-mRNA Splicing factor | 34 LEPGPSSY 41 |  | NP_067051 |
|  | 98 PAPPPSS 105 | ... | ... |
| Williams Beuren syndrome-Chromosome region 18 | 90 TQAQI 94 | 1.6 | NP_115693.2 |
| Wiskott-Aldrich syndrome-Protein family member A | 95 PSRPAPPPP 103 | 5.2 | CAD48858.1 |
|  | 117 IPPP 120 | ... | ... |
| WASP-interacting Protein | 94 IPSRPAPPPP 103 | 1.6 | NA_003378.2 |
|  | 95 PSRPAPP-PPSSSTHD 109 | ... | AAC03767.1 |
| A disintegrin and metalloproteinase domain 15 | 94 IPSRPAPPPPS-SS 106 | 0.6 | AAP88766.1 |
|  | 123 EPTAPQVL 130 | ... | ... |
| Huntington disease-associated Protein | 160 AAPGSP 165 | 0.026 | A46068 |
|  | 165 PQFMQTI 171 | ... | ... |
| Zinc finger homeodomain 4 | 95 PSRPAPPPPSSS 106 | 0.063 | NP_078997.2 |
|  | 114 DPQIPPP 120 | ... | ... |
| Histone-Lysine- | 99 APPPPSSS 106 | 0.49 | DOTL_HUMAN |

TABLE 5A-continued

HPDSEs in Gag protein of HTLV-I and the Accession numbers of corresponding host proteins in GenBank, Peptides disclosed as SEQ ID NOS 395-433, respectively, in order of appearance.

| Name of protein | Position of Protein | E-value | Accession Number |
|---|---|---|---|
| N-methyltransferase, H3lys. | 159 QAAPGSPQ 166 | . . . | . . . |
| Amyloid beta (A4) precursor | 210 ISEAETRGI 217 | 0.66 | NP_061916.2 |
| Tumor endothelial marker 8 | 268 QGLEE 272 | 1.2 | NP_115584.1 |
| TPA:harmonin isoform b3 | 222 PLAGPLR 228 | 1.2 | DAA00086.1 |
| From a.a 300- end | | | |
| RNA binding motif protein 4 | 311 CQKLLQARG 319 | 0.003 | AAH32735.1 |
| DJ511b24.2.5 phospholipase C | 322 NSPLGDMLR 330 | 0.83 | CAC36283.1 |
| Hypothetical protein simlar To RNA binding protein | 357 CFRCGKAGHWSRDC 370 | 0.003 | NP_113680.1 |
| SFRS protein kinase 2 isoform a | 401 PEPEPEEDAL 410 | 0.024 | NP_872634.1 |
| Unknown protein | 380 CPLC 383 | 0.033 | AAH52282.1 |
| | 405 PEEDALLL-DL 414 | . . . | . . . |
| Retinoblastoma binding protein 6 | 357 CFRCGKAGH 365 | 0.14 | BAC77637.1 |
| Hypothetical protein (XP_303812) | 374 RPPPGPCPL 382 | 1.1 | XP_303812.1 |
| Serin kinase SRPK2 | 401 PEPEPEEDAL 410 | 1.1 | AAC29140.1 |
| Cell division Cycle 2-like 2 isoform5 | 362 KAGHWSRDCTQPRPP 376 | 2 | NP_277073.1 |
| Protein Kinase | 371 TQPRPPPG 378 | 2 | E54024 |
| Putative transcription-factor CR53 | 394 PRLKPTIPEPE 404 | 2 | AAB 70531.1 |
| PITSLRE protein Kinase-beta SV3 isoform | 362 KAGHWSRDCTQPRPP 376 | 2 | AAC95300.1 |
| | 371 TQPRPPPG 378 | . . . | . . . |
| Gag protein | 357 CFRCGKAGHWSRDC 370 | 2 | AF480924_1 |
| Unnamed protein product | 357 CFRCGKAGHWSRDC 370 | 0.010 | BAB70769.1 |

TABLE 5B

HPDSEs found in Poly protein of HTLV-I and the Accession numbers of corresponding host proteins GenBank. Peptides disclosed as SEQ ID NOS 434-494, respectively, in order of appearance

| Name of Protein | Position of Sequences | E-value | Accession Number |
|---|---|---|---|
| From a.a 1-300 | | | |
| Gag-pro-pol precursor | 35 ERLQALQHLV 44 | 6e-32 | AAG18012.1 |
| Pol protein | 49 EAGHIEPYT 57 | 3e-29 | AAM81188.1 |
| | 77 IHDLRATN 84 | . . . | |
| Polymerase | 48 LEAGHIEP 55 | 7e-29 | AAC63292.1 |
| Polymerase | 132 FAFTVP 137 | 1e-28 | AAC63291.1 |
| Gag-pro-pol-env Protien | 150 WKVLPQGFKNSPT 161 | 1e-28 | AF164611_1 |
| | 219 VSENKTQ 225 | . . . | |
| Ga Polymerase | 184 ILQYMDDIL 192 | 1e-26 | AAC63290.1 |
| Polymerase | 259 LPELQALLGEIQWV 279 | 2e-27 | AAC63294.1 |
| Human endogenous-type C oncovirus Protein | 113 IDLRDAFF 120 | 1e-11 | AAA73090.1 |
| | 157 FKNSPTLF 164 | | |
| | 182 CTILQYMDDILL 193 | | |
| Similar to Polymerase | 187 YMDDILLASP 196 | 2e-10 | XP_045436.1 |
| Polymerase | 183 TILQYMDDILL 193 | 1e-08 | AAA3 5986.1 |
| Seven transmembrane-Helix receptor | 156 GFKNSPTLF 164 | 5e-05 | BAC05726.1 |
| | 184 ILQYMDDILL 193 | . . . | |
| Reverce Transcriptase | 152 VLPQGFKNSPTL 163 | 8e-04 | CAA13575.1 |
| From a.a 300-600 | | | |
| Cocaine-and amphetamine-Regulate transcript | 329 LPLLGA 334 | 23 | NP_004282.1 |
| Mucine JUL10-Human | 334 AIMLTLTGTTTV 345 | 0.66 | CAA52911.1 |
| | 354 PLVWLHAPLPH 364 | . . . | . . . |
| Hypothetical protein | 348 QSKEQ 352 | | XP_297250.1 |
| Similar to hypothetic-Protein FLJ21148 | 370 WGQLLASAVLL 380 | 5.2 | AAH22451.1 |
| Similar to Protein-O-mannosyltransferase 1 | 372 QLLASVLLL 381 | 17 | AAH22877.1 |
| Unknown Protein | 397 HHNISTQT 404 | 5.2 | AF433663_1 |
| | 406 NQFIQTSDH 414 | . . . | . . . |
| unnamed Protein Product | 436 ELWNTFL 442 | 17 | BAA90944.1 |
| chorein isoform B | 461 SPVIINT 467 | 9.4 | NP_056001.1 |
| polyprotein | 472 FSDGSTS-RAAY 482 | 0.28 | AAC63291.1 |

TABLE 5B-continued

HPDSEs found in Poly protein of HTLV-I and the Accession numbers of corresponding host proteins GenBank. Peptides disclosed as SEQ ID NOS 434-494, respectively, in order of appearance

| Name of Protein | Position of Sequences | E-value | Accession Number |
|---|---|---|---|
| Pol protein | 500 PHKSAQRAEL 509 | 0.66 | AAL60056.1 |
| DNA Polymerase alpha 70 kDa subunit | 487 KQILSQRS-FPL-PP 499 | 7 | DPO2__HUMAN |
| Polymerase | 500 PHKSAQRAELLGLLHGL 514 | 0.28 | AAD21097.1 |
| Hypotetical Protein | 536 HYLRTLALGTFQG 548 | 13 | XP__300065.1 |
| Protein o-mannosyl-transferase 1 | 533 YLYHYLRTL 541 | 17 | AF095136__1 |
| Unnamed protein product | 557 ALLPRL 562 | 17 | BAA90944.1 |
| Polymerase | 569 YLHHVRSHTNLP 580 | 0.28 | AAD21097.1 |
| Glucosidase, alpha | 591 DALLITPVLQ 600 | 2.9 | AAH40431.1 |

From a.a 600-end

| Titin | 623 TTTEASNIL 631 | | CAD12456.1 |
|---|---|---|---|
| | 694 RKETSSE 700 | | ... |
| | 724 PAYISQ 729 | | ... |
| Titin isoform N2-B | 795 VLTNCHKTRW 804 | 9.2 | NP__0033310 |
| | 846 EALQEAA 852 | ... | ... |

From a.a 600-end

| Myosin-IXA | 646 MPRGHIRRG 654 | | AF117888__1 |
|---|---|---|---|
| | 679 VWVDTF 684 | | ... |
| | 702 ISSLLQAIAHLG 713 | | ... |
| | 749 NPTSSGLVERSNGIL 763 | | ... |
| Polymerase | 656 PNHIWQGDITH 666 | 1e-10 | AF298588__1 |
| | 678 HVWVDTFSG 686 | ... | ... |
| KIAA1255 protein | 695 KETSSEA-ISSLLQAI 709 | 30 | BAA86569.2 |
| Proprotein convetase-Subtilisin | 633 SCHA-CRGGNP 642 | 30 | AAH36354.1 |
| | 722 NGPAYI 727 | ... | ... |
| KIAA1466 protein | 721 DNGPAYI 727 | 54 | BAA95990.1 |
| Similar to Synaptic-glycoprotein SC2 | 800 HKTRWQLHHS 809 | 17 | XP__293655.1 |
| hypothetical protein (FLJ23754) | 803 RWQLHHSPRLQPIPETR 819 | 22 | NP__689888.1 |
| FLJ00136 | 804 WQLHHSPR 811 | 54 | BAB84891.1 |
| hypothetical protein (XP__296205) | 844 PQEALQEAAGAAL 856 | 22 | XP__296205.1 |
| Sodium Channel | 886 DPKBKDLQHH 895 | 30 | NP__777594.1 |
| Orphan nuclear receptor-steroidogenic factor 1 | 867 IPWRLLKRAACPRP 880 | 30 | AABN3 5923.1 |
| tocopherol (alpha) | 869 WRLLK-RAACP 878 | 40 | NP__000361.1 |
| JM1I protein | 835 GLNSQWKGPQE 846 | 40 | AF196779__9 |
| IKB kinase-b | 845 QEALQEAAGAALIP 858 | 40 | AAD08997.1 |

TABLE 5C

HPDSEs in Env protein of HTLV-I and the Accession numbers of corresponding host proteins in GenBank, Peptides disclosed as SEQ ID NOS 495-532, respectively, in order of appearance.

| Name of Protein | Position of Protein | E-value | Accession Number |
|---|---|---|---|
| Hypothetical protein (XP__296474) | 56 ALSADQALQPP 66 | 17 | XP__296474.1 |
| NADPH oxidase subunit (gp91-3) | 132 YWKFQQDVNFTQEVSH 147 | 13 | AAG15435.1 |
| Unnamed protein product | 139 VNFTQE 144 | 13 | BAA91630.1 |
| Hypothetical protein (XP__299930) | 171 DPIWFLNTEPSQL 183 | 1.2 | XP__299930 |
| | 86 PHWIKKPN 93 | — | — |
| Forkhead box protein Q1 | 179 EPSQL-------PPTAPPLL 194 | 7 | FXQ1__Human |
| KIAA1458 protein | 119 SWTCPYTGAVSSPY 132 | 7 | BAA95982.1 |
| | 241 YSPNVSVP-----SPSSTP 254 | 7 | — |
| Similar to Tricarboxylate-transport protein | 182 QLPPTAPPLLSH 193 | 9.3 | XP__301334.1 |
| Hypothetical protein | 200 L-EPSIPWKSKL---LTLVQ 215 | 17 | CAB55300.1 |
| Cofactor required for SP1-Transcriptional action | 240 LYSPNVSVPSPS 251 | 23 | NP__004822.2 |
| Hypothetical protein (XP__303895) | 253 TPLLYP-SLALP 263 | 5.2 | XP__299917.1 |
| Hypothetical protein (XP__299917) | 255 LLYPSLALPAPHLT 268 | 17 | XP__299917.1 |

TABLE 5C-continued

HPDSEs in Env protein of HTLV-I and the Accession numbers of corresponding host proteins in GenBank, Peptides disclosed as SEQ ID NOS 495-532, respectively, in order of appearance.

| Name of Protein | Position of Protein | E-value | Accession Number |
|---|---|---|---|
| From a.a 300-600 | | | |
| Similar to Ral guanine nucleotide-Exchange factor | 305 TLGSRSRR 312 | 44 | AAH33708.1 |
| Simlar to Keratin-Type 1cytoskeletal 18 | 319 WLVSALA 325 | 18 | XP_302057.1 |
| | 326 MGAGVAG-RITGSMS 339 | — | — |
| Hypothetical protein MGC26719 | 316 VAVWLV 321 | 44 | AAH30643.1 |
| | 446 GITLVALLLLVI 457 | — | — |
| MGC44669 protein | 446 GITLVALLL 454 | 44 | AAH45695.1 |
| NADH dehydrogenase subunit 3 | 452 LLLLVILA 459 | — | AAK17292.2 |
| Unnamed protein product | 377 QNRRGLDLLFWEQGGLC 393 | 6e-11 | BAC11396.1 |
| | 394 KALQEQCCF 402 | — | — |
| Env protein | 377 QNRRGLDLLFWEQGGLC 393 | 9e-09 | AAD34324.1 |
| MCM10 minichromosome ... | 416 RPPL-ENRV 423 | 7.5 | NP_060988.2 |
| | 420 ENRVL 424 | — | — |
| Envelop protein | 424 L--TG-WGL 429 | 0.021 | AF156963_1 |
| Enverin | 349 EVDKDISQLT 358 | 0.002 | AF506835_1 |
| Enverin | 377 QNRRGLDLL 385 | — | — |
| Sema domain–Immunoglobulin domain | 413 LQERPPL 419 | 33 | NP_060259.2 |
| FXR2 protein | 415 ERPPLE 420 | | AAH51907.1 |
| Unknown | 416 RPPLENRV 423 | 44 | |
| Fragile X mental retardation Autosomal homlog 2 | 394 KALQEQCCFLNITNSHVSIL 413 | 1.7 | AAH20090 |
| Env-related transmembrane protein | 379 RRGLDLLFWEQGGL 392 | 3.1 | AAB24915.1 |
| | 393 CKALQEQCCFLN 404 | — | — |
| MGC44669 | 446 GITLVALLL 454 | 44 | |
| DKFZP5640243 protein | 464 LRQLRHLP 471 | 7.5 | NP_056222.1 |
| NADH dehydrogenase subunit 3 | 452 LLLLVILA 459 | 44 | AAK17656.2 |
| | 448 TLVALLLLVL 457 | — | — |

TABLE 5D

Several significant HPDSEs in HTLV-1 polyproteins (gag, pol and env), Peptides disclosed as SEQ ID NOS 533-535, respectively, in order of appearance.

| | Viral protein | Human endogenous retrovirus elements | Highest homologous amino acids in overlapping domains (Number of aa.) | Identities in overlapping aa. (%) | Total number of display sequences producing significant alignments E value < 2 |
|---|---|---|---|---|---|
| 1 | Pol polyprotein | Polymerase | SAQRAEL (7 aa.) | 241/813 (29%) | 45 sequences and the best E value: 4e-74 |
| 2 | Gag protein | Gag Protein | QQGLRREYQ (9 aa.) | 27/35 (77%) | 12 sequences and the best E value: 8e-09 |
| 3 | Env Protein | Envelope protein | QNRRGLDLL (9 aa.) | 38/108 (35%) | 10 sequences and the best E value: 6e-08 |

TABLE 6

GenBank Accession numbers of coronavirus proteins used for sequence analysis of homology

| Protein Name | Accession number |
|---|---|
| S glycoprotein SARS-CoV Tor2 | NP_828851 |
| S glycoprotem SARS-CoV CUHK-W1 | P59594 |
| S glycoprotein HCoV-229E | NP_073551 |
| S glycoprotein HCoV-OC43 | AAA03055 |
| S glycoprotein BCoV | NP_150077 |
| S glycoprotein MHV | NP_045300 |
| S glycoprotein IBV | NP_040831 |
| ORF1a polyprotein SARS-CoV Tor2 | NP_828850 |
| ORF1a polyprotein SARS-CoV CUHK-W1 | AAP13575 |
| ORF1a polyprotein HCoV-229E | CAA49377 |
| ORF1a polyprotem BCoV | NP_150074 |
| ORF1a polyprotein MHV | NP_045298 |
| ORF1a polyprotein IBV | NP_040829 |

TABLE 7

Legend of human protein domains and bacterial sequences elements in S proteins of coronaviruses shown in FIG. 18.

| Designation | Protein Name | Genbank Accession |
|---|---|---|
| HP1 | Hydroxyacid oxidase 1 | NP_060015.1 |
| HP2 | KIAA0342 protein | BAA20800.3 |
| HP3 | Polycystin | 2203412A |
| HP4 | Interleukin 1 receptor-like 1 | IRL1human |
| HP5 | KIAA0041 protein | BAA05064.2 |
| HP6 | Sublingual gland mucin | AAB65151.1 |
| HP7 | Potassium Voltage-gated channel, subfamily H | NP_647479.2 |
| HP8 | Hypotetical protein | XP_212347.1 |
| HP9 | NDR3 | AF251O54_1 |
| HP10 | Melanoma-associated antigen p97 | NP_005920.1 |
| HP11 | NDRG family member 3 | NP_114402.1 |
| HP12 | Nicein | CAA52108.1 |
| HP13 | Laminin B2t chain precursor | A4018 |
| HP14 | Hypothetical Protein FLJ12242 | NP_078957.1 |
| HP15 | Simlar to golgi autoantigen | XP_208786.1 |
| HP16 | Zinc finger protein 328 | AF455357_1 |
| HP17 | Cadherin 20 precursor | CADK_HUMAN |
| HP18 | c GMP-dependant protein kinase | CAA76073.1 |
| HP19 | Scavenger receptor with C-type lectin type I | JC7595 |
| HP20 | KIAA1756 protein | BAB21847.1 |
| HP21 | Striatin | NP_003153.1 |
| HP22 | Transcription factor SUPT3H | AAC70014.1 |
| HP23 | Angrgm-52 | AAL62340.1 |
| HP24 | Unknown protein for MGC: 39798 | AAH29605.1 |
| HP25 | Golgi Autoantigen | NP_004478.1 |
| HP26 | Sa gene | AAC31667.1 |
| HP27 | Intergrin alpha-6chain precursor | B36429 |
| HP28 | Hyaluron-mediated motility receptor | NP_036617.1 |
| HP29 | Hyaluron receptor | AAC52049.1 |
| HP30 | Nucleoporin like 1 | NP_054808.1 |
| HP31 | Transcription factor | CAA72416.1 |
| HP32 | Winged-helix nude | NP_003584.2 |
| HP33 | toll-like receptor 4 isoform D | NP_612566.1 |
| HP34 | WW domain binding protein-1 | NP_036609.1 |
| bacterial | Peyer's patch-specific virulence factor gipA [*S. typhimurium*] | AAF98319 |
| bacterial | Peyer's patch-specific virulence factor gipA [*E. coli* CFT073] | NP_752781 |

TABLE 8

Proteins possessing homologous human (HP) and mouse (MP) domains and sequences elements relative to coronavirus ORF1a proteins in FIG. 1 9A/B.

| Designation | Protein name | Accession No. |
|---|---|---|
| HP1 | B aggressive Lymphoma | NP_113646.1 |
| HP2 | KIAA1268 protein (homologous to MP2) | BAA86582.1 |
| HP3 | LRP 16 protein | NP_054786.2 |
| MP1 | B aggressive Lymphoma | NP_084529.1 |
| MP2 | unnamed protein (homologous to HP2) | BAC40943.1 |
| MP3 | unnamed protein | BAG29897.1 |

REFERENCE LIST

1. Alter, H. J. & Seeff, L. B. Viral Hepatitis. Zuckerman, A. Z. & Thomas, H. C. (eds.), pp. 467-498 (Churchill Livingstone, Edinburgh, UK, 1997).

2. Rifi, A., Morrisson, L. A. & Knipe, D. M. Fields Virology. Lippincott-Raven, Philadelphia (1996).

3. Kato, N. et al. Genetic drift in hypervariable region 1 of the viral genome in persistent hepatitis C virus infection. *J Virol* 68, 4776-4784 (1994).

4. Farci, P. et al. Prevention of hepatitis C virus infection in chimpanzees by hyperimmune serum against the hypervariable region 1 of the envelope 2 protein. *Proc. Natl. Acad. Sci. U.S.A* 93, 15394-15399 (1996).

5. Farci, P. et al. The outcome of acute hepatitis C predicted by the evolution of the viral quasispecies. *Science* 288, 339-344 (2000).

6. Kato, N. et al. Humoral immune response to hypervariable region 1 of the putative envelope glycoprotein (gp70) of hepatitis C virus. *J Virol* 67, 3923-3930 (1993).

7. Major, M. E., Rehermann, B. & Feinstone, S. M. Fields Virology. Knipe, D. & Howley, P. M. (eds.), pp. 1127-1161 (Lippincott Williams & Wilkins, Philadelphia, 2001).

8. Shimizu, Y. K. et al. A hyperimmune serum against a synthetic peptide corresponding to the hypervariable region 1 of hepatitis C virus can prevent viral infection in cell cultures. *Virology* 223, 409-412 (1996).

9. Farci, P. et al. Lack of protective immunity against reinfection with hepatitis C virus. *Science* 258, 135-140 (1992).

10. Forns, X. et al. Hepatitis C virus lacking the hypervariable region 1 of the second envelope protein is infectious and causes acute resolving or persistent infection in chimpanzees. *Proc. Natl. Acad. Sci. U.S.A* 97, 13318-13323 (2000).

11. Ploegh, H. L. Viral strategies of immune evasion. *Science* 280, 248-253 (1998).

12. Beck, S. & Barrell, B. G. Human cytomegalovirus encodes a glycoprotein homologous to MHC class-I antigens. *Nature* 331, 269-272 (1988).

13. Reyburn, H. T. et al. The class I MHC homologue of human cytomegalovirus inhibits attack by natural killer cells. *Nature* 386, 514-517 (1997).

14. Zhao, Z. S., Granucci, F., Yeh, L., Schaffer, P. A. & Cantor, H. Molecular mimicry by herpes simplex virus-type 1: autoimmune disease after viral infection. *Science* 279, 1344-1347 (1998).

15. Taylor, D. R., Shi, S. T., Romano, P. R., Barber, G. N. & Lai, M. M. Inhibition of the interferon-inducible protein kinase PKR by HCV E2 protein. *Science* 285, 107-110 (1999).

16. Kabat, E. A., Wu, T. T., Perry, H. M., Gottesman, K. S. & Foeller, C. Sequences of protein of immunological interest. US Department of Health and Human Services, Washington, D.C. (1991).

17. Eigenbrot, C., Randal, M., Presta, L., Carter, P, & Kossiakoff, A. A. X-ray structures of the antigen-binding domains from three variants of humanized anti-p185HER2 antibody 4D5 and comparison with molecular modeling. *J. Mol. Biol.* 229, 969-95.

18. Penin, F. et al. Conservation of the conformation and positive charges of hepatitis C virus E2 envelope glycoprotein hypervariable region 1 points to a role in cell attachment. *J. Virol.* 75, 5703-5710 (2001).

19. Chothia, C. & Lesk, A. M. Canonical structures for the hypervariable regions of immunoglobulins. *J. Mol. Biol.* 196, 901-917 (1987).

20. Korenaga, M., Hino, K., Okazaki, M., Okuda, M. & Okita, K. Differences in hypervariable region 1 quasispecies between immune complexed and non-immune complexed hepatitis C virus particles. *Biochem. Biophys. Res. Commun.* 240, 677-682 (1997).

21. Wyatt, C. A. et al. Immunity in chimpanzees chronically infected with hepatitis C virus: role of minor quasispecies in reinfection. *J Virol,* 72, 1725-1730 (1998).

22. Larke, B. et al. Acute nocosomal hepatitis C virus infection detected by nucleic acid amplification testing of a regular blood donor. *Transfusion* (2002).

23. Manzin, A. et al. Evolution of hypervariable region 1 of hepatitis C virus in primary infection. *J. Virol.* 72, 6271-6276 (1998).
24. Odeberg, J. et al. Variation of hepatitis C virus hypervariable region 1 in immunocompromised patients. *J Infect. Dis.* 175, 938-943 (1997).
25. Ni, Y. H. et al. Decreased diversity of hepatitis C virus quasispecies during bone marrow transplantation. *J Med. Virol* 58, 132-138 (1999).
26. Van Doorn, L. et al. Sequence evolution of the hypervariable region in the putative envelope region E2/NS1 of hepatitis C virus is correlated with specific humoral immune responses. *J Virol* 69, 713-778 (1995).
27. Lu, L., Nakano, T., Orito, E., Mizokami, M. & Robertson, B. H. Evaluation of accumulation of hepatitis C virus mutations in a chronically infected chimpanzee: comparison of the core, E1, HVR1, and NS5b regions. *J. Virol.* 75, 3004-3009 (2001).
28. Carayannopoulos, L. &. C. J. D. Fundamental Immunology. William E. Paul (ed.), pp. 283-314 (Raven Press, New York, 1993).
29. Gerotto, M. et al. A 385 insertion in the hypervariable region 1 of hepatitis C virus E2 envelope protein is found in some patients with mixed cryoglobulinemia type 2. *Blood* 98, 2657-2663 (2001).
30. Sambrook et al. 1989. Molecular Cloning—A Laboratory Manual, Cold Spring Harbor Laboratories.
31. Peiris J S, Lai S T, Poon L L, Guan Y, Yam L Y, Lim W et al. Coronavirus as a possible cause of severe acute respiratory syndrome. Lancet 2003;361(9366):1319-25.
32. Fouchier R A, Kuiken T, Schutten M, van Amerongen G, van Doornum G J, van den Hoogen B G et al. Aetiology: Koch's postulates fulfilled for SARS virus. Nature 2003; 423(6937):240.
33. Marra M A, Jones S J, Astell C R, Holt R A, Brooks-Wilson A, Butterfield Y S et al. The Genome sequence of the SARS-associated coronavirus. Science 2003; 300(5624): 1399-404.
34. Holmes K V. Fields' virology. 4th ed. ed. Philadelphia: Lippincott Williams & Wilkins; 2001.
35. Abbott A. Pet theory comes to the fore in fight against SARS. Nature 2003;423(6940):576.
36. Enserink M. Infectious diseases. Clues to the animal origins of SARS. Science 2003;300(5624):1351.
37. Ruan Y J, Wei C L, Ee A L, Vega V B, Thoreau H, Su S T et al. Comparative full-length genome sequence analysis of 14 SARS coronavirus isolates and common mutations associated with putative origins of infection. Lancet 2003; 361(9371):1779-85.
38. Sanchez C M, Gebauer F, Sune C, Mendez A, Dopazo J, Enjuanes L. Genetic evolution and tropism of transmissible gastroenteritis coronaviruses. Virology 1992;190(1): 92-105.
39. Rota P A, Oberste M S, Monroe S S, Nix W A, Campagnoli R, Icenogle J P et al. Characterization of a novel coronavirus associated with severe acute respiratory syndrome. Science 2003;300(5624):1394-9.
40. Navas S, Seo S H, Chua M M, Sarma J D, Lavi E, Hingley S T et al. Murine coronavirus spike protein determines the ability of the virus to replicate in the liver and cause hepatitis. J. Virol. 2001;75(5):2452-7.
41. Navas S, Seo S H, Chua M M, Das S J, Hingley S T, Lavi E et al. Role of the spike protein in murine coronavirus induced hepatitis: an in vivo study using targeted RNA recombination. Adv. Exp. Med. Biol. 2001;494:139-44.
42. Haijema B J, Volders H, Rottier P J. Switching species tropism: an effective way to manipulate the feline coronavirus genome. J. Virol. 2003;77(8):4528-38.
43. Kuo L, Godeke G J, Raamsman M J, Masters P S, Rottier P J. Retargeting of coronavirus by substitution of the spike glycoprotein ectodomain: crossing the host cell species barrier.
44. Lamb R A, Horvath C M. Diversity of coding strategies in influenza viruses. Trends Genet. 1991;7(8):261-6.
45. Pelet T, Curran J, Kolakofsky D. The P gene of bovine parainfluenza virus 3 expresses all three reading frames from a single mRNA editing site. EMBO J. 1991; 10(2): 443-8.
46. Holmes E C. Molecular clocks and the puzzle of RNA virus origins. J. Virol. 2003;77(7):3893-7.
47. Domingo E, Menendez-Arias L, Holland J J. RNA virus fitness. Rev. Med. Virol. 1997;7(2):87-96.
48. Rowe C L, Baker S C, Nathan M J, Sgro J Y, Palmenberg A C, Fleming J O. Quasispecies development by high frequency RNA recombination during MHV persistence. Adv. Exp. Med. Biol. 1998;440:759-65.:759-65.
49. Brown E G, Bailly J E. Genetic analysis of mouse-adapted influenza A virus identifies roles for the NA, PB1, and PB2 genes in virulence. Virus Res. 1999;61(1):63-76.
50. Brown E G, Liu H, Kit L C, Baird S, Nesrallah M. Pattern of mutation in the genome of influenza A virus on adaptation to increased virulence in the mouse lung: identification of functional themes. Proc. Natl. Acad. Sci. U.S.A 2001; 98(12):6883-8.
51. Oleszak E L. Molecular mimicry between Fc receptors and viral antigens. Arch. Immunol. Ther. Exp. (Warsz.) 1994;42(2):83-8.
52. Oleszak E L, Leibowitz J L. Immunoglobulin Fc binding activity is associated with the mouse hepatitis virus E2 peplomer protein. Virology 1990;176(1):70-80.
53. Thompson J D, Plewniak F, Ripp R, Thierry J C, Poch O. Towards a reliable objective function for multiple sequence alignments. J. Mol. Biol. 2001;314(4):937-51.
64. Sauder J M; Arthur J W, Dunbrack R L, Jr. Large-scale comparison of protein sequence alignment algorithms with structure alignments. Proteins 2000;40(1):6-22.
55. Lai M M C H K. Fields' virology. 4th ed. ed. Philadelphia: Lippincott Williams & Wilkins; 2001.
56. Phillips J J, Weiss S R. MHV neuropathogenesis: the study of chimeric S genes and mutations in the hypervariable region. Adv. Exp. Med. Biol. 2001;494:115-9:115-9.
57. Liu H J, Lee L H, Shih W L, Lin M Y, Liao M H. Detection of infectious bronchitis virus by multiplex polymerase chain reaction and sequence analysis. J. Virol. Methods 2003;109(1):31-7.
58. Bromham L, Penn D. The modern molecular clock. Nat. Rev. Genet. 2003;4(3):216-24.
59. Peiris J S, Chu C M, Cheng V C, Chan K S, Hung I F, Poon L L et al. Clinical progression and viral load in a community outbreak of coronavirus-associated SARS pneumonia: a prospective study. Lancet 2003;361(9371):1767-72.
60. Drosten C, Gunther S, Preiser W, van der W S, Brodt H R, Becker S et al. Identification of a novel coronavirus in patients with severe acute respiratory syndrome. N. Engl. J. Med. 2003;348(20):1967-76.
61. Tyler K L, Nathanson N. Fields' virology. 4th ed. ed. Philadelphia: Lippincott Williams & Wilkins; 2001.
62. Welch R A, Burland V, Plunkett G, III, Redford P, Roesch P, Rasko D et al. Extensive mosaic structure revealed by the complete genome sequence of uropathogenic *Escherichia coli*. Proc. Natl. Acad. Sci. U.S.A 2002;99(26):17020-4.

63. Stanley T L, Ellermeier C D, Slauch J M. Tissue-specific gene expression identifies a gene in the lysogenic phage Gifsy-1 that affects *Salmonella enterica* serovar typhimurium survival in Peyer's patches. J. Bacteriol. 2000;182(16):4406-13.
64. Gebauer F, Posthumus W P, Correa I, Sune C, Smerdou C, Sanchez C M et al. Residues involved in the antigenic sites of transmissible gastroenteritis coronavirus S glycoprotein. Virology 1991;183(1):225-38.
65. Krempl C, Ballesteros M L, Zimmer G, Enjuanes L, Klenk H D, Herrler G. Characterization of the sialic acid binding activity of transmissible gastroenteritis coronavirus by analysis of haemagglutination-deficient mutants. J. Gen. Virol. 2000;81(Pt 2):489-96.
66. Krempl C, Schultze B, Laude H, Herrler G. Point mutations in the S protein connect the sialic acid binding activity with the enteropathogenicity of transmissible gastroenteritis coronavirus. J. Virol. 1997;71

```
Thr Asn Gly Ser Trp His Ile Asn Ser Thr Ala Leu Asn Cys Asn Asp
            35                  40                  45

Ser Leu Asn Thr Gly Trp Ile Ala Gly Leu Phe Tyr Arg Arg Asn Phe
    50                  55                  60

Asn Ser Ser Gly Cys Pro Glu Arg
65                  70

<210> SEQ ID NO 4
<211> LENGTH: 72
<212> TYPE: PRT
<213> ORGANISM: HCV 1a E2 (A1-3)

<400> SEQUENCE: 4

Glu Thr Tyr Val Thr Gly Gly Val Thr Gly Arg Gly Val Ala Thr Ile
1               5                   10                  15

Ala Gly Leu Phe Ser Pro Gly Pro Gln Gln Lys Ile Gln Leu Val Asn
            20                  25                  30

Thr Asn Gly Ser Trp His Ile Asn Ser Thr Ala Leu Asn Cys Asn Asp
            35                  40                  45

Ser Leu Lys Thr Gly Trp Ile Ala Gly Leu Phe Tyr Arg Arg Asn Phe
    50                  55                  60

Asn Pro Ser Gly Cys Pro Glu Arg
65                  70

<210> SEQ ID NO 5
<211> LENGTH: 72
<212> TYPE: PRT
<213> ORGANISM: HCV 1a E2 (A1-4)

<400> SEQUENCE: 5

Thr Thr Tyr Val Thr Gly Gly Val Thr Gly Arg Gly Val Ala Thr Ile
1               5                   10                  15

Thr Gly Leu Phe Ser Pro Gly Pro Gln Gln Lys Ile Gln Leu Val Asn
            20                  25                  30

Thr Asn Gly Ser Trp His Ile Asn Ser Thr Ala Leu Asn Cys Asn Asp
            35                  40                  45

Ser Leu Asn Thr Gly Trp Ile Ala Gly Leu Phe Tyr Arg Tyr Asn Phe
    50                  55                  60

Asn Ser Ser Gly Cys Pro Glu Arg
65                  70

<210> SEQ ID NO 6
<211> LENGTH: 72
<212> TYPE: PRT
<213> ORGANISM: HCV 1a E2 (A1-5)

<400> SEQUENCE: 6

Glu Thr Tyr Val Thr Gly Gly Ala Ala Gly Arg Gly Val Ala Thr Ile
1               5                   10                  15

Thr Gly Leu Phe Ser Ala Gly Pro Gln Gln Lys Ile Gln Leu Val Asn
            20                  25                  30

Thr Asn Gly Ser Trp His Ile Asn Ser Thr Ala Leu Asn Cys Asn Asp
            35                  40                  45

Ser Leu Lys Thr Gly Trp Ile Ala Gly Leu Phe Tyr Arg Asn Asn Phe
    50                  55                  60

Asn Ser Ser Gly Cys Pro Glu Arg
65                  70
```

<210> SEQ ID NO 7
<211> LENGTH: 72
<212> TYPE: PRT
<213> ORGANISM: HCV 1a E2;A1-6

<400> SEQUENCE: 7

Thr Thr Tyr Val Thr Gly Gly Val Thr Gly Arg Gly Val Ala Thr Asn
1               5                   10                  15

Thr Gly Leu Phe Ser Ser Gly Pro Gln Gln Lys Ile Gln Leu Val Asn
            20                  25                  30

Thr Asn Gly Ser Trp His Ile Asn Ser Thr Ala Leu Asn Cys Asn Asp
        35                  40                  45

Ser Leu Asn Thr Gly Trp Ile Ala Gly Leu Phe Tyr Arg Arg Asn Phe
    50                  55                  60

Asn Ser Ser Gly Cys Pro Glu Arg
65                  70

<210> SEQ ID NO 8
<211> LENGTH: 72
<212> TYPE: PRT
<213> ORGANISM: HCV 1a E2 (A1-7)

<400> SEQUENCE: 8

Glu Thr Tyr Val Thr Gly Gly Ala Ala Gly Arg Gly Val Ala Thr Ile
1               5                   10                  15

Ala Gly Leu Phe Ser Ser Gly Pro Gln Gln Lys Ile Gln Leu Val Asn
            20                  25                  30

Thr Asn Gly Ser Trp His Ile Asn Ser Thr Ala Leu Asn Cys Asn Asp
        35                  40                  45

Ser Leu Lys Thr Gly Trp Ile Ala Gly Leu Phe Tyr Arg Asn Asn Phe
    50                  55                  60

Asn Ser Ser Gly Cys Pro Glu Arg
65                  70

<210> SEQ ID NO 9
<211> LENGTH: 72
<212> TYPE: PRT
<213> ORGANISM: HCV 1a E2 (A1-8)

<400> SEQUENCE: 9

Glu Thr Tyr Val Thr Gly Gly Val Thr Gly Arg Gly Val Ala Thr Ile
1               5                   10                  15

Ala Gly Leu Phe Ser Pro Gly Pro Gln Gln Lys Ile Gln Leu Val Asn
            20                  25                  30

Thr Asn Gly Ser Trp His Ile Asn Ser Thr Ala Leu Asn Cys Asn Asp
        35                  40                  45

Ser Leu Asn Thr Gly Trp Ile Ala Gly Leu Leu Tyr Arg Arg Asn Phe
    50                  55                  60

Asn Ser Ser Gly Cys Pro Glu Arg
65                  70

<210> SEQ ID NO 10
<211> LENGTH: 72
<212> TYPE: PRT
<213> ORGANISM: HCV 1a E2 (A1-9)

<400> SEQUENCE: 10

Glu Thr Tyr Val Thr Gly Gly Val Thr Gly Arg Gly Val Ala Thr Ile
1               5                   10                  15

```
Ala Gly Leu Phe Ser Ser Gly Pro Gln Gln Lys Ile Gln Leu Val Asn
            20                  25                  30

Thr Asn Gly Ser Trp His Ile Asn Ser Thr Ala Leu Asn Cys Asn Asp
        35                  40                  45

Ser Leu Asn Thr Gly Trp Ile Ala Gly Leu Phe Tyr Arg Arg Asn Phe
    50                  55                  60

Asn Ser Ser Gly Cys Pro Glu Arg
65                  70

<210> SEQ ID NO 11
<211> LENGTH: 72
<212> TYPE: PRT
<213> ORGANISM: HCV 1a E2 (A1-10)

<400> SEQUENCE: 11

Glu Thr Tyr Val Thr Gly Gly Ala Ala Gly Arg Gly Val Ala Thr Ile
1               5                   10                  15

Thr Gly Leu Phe Ser His Gly Pro Gln Gln Lys Ile Gln Leu Val Asn
            20                  25                  30

Thr Asn Gly Ser Trp His Ile Asn Ser Thr Ala Leu Asn Cys Asn Asp
        35                  40                  45

Ser Leu Lys Thr Gly Trp Ile Ala Gly Leu Phe Tyr Arg Asn Asn Phe
    50                  55                  60

Asn Ser Ser Gly Cys Pro Glu Arg
65                  70

<210> SEQ ID NO 12
<211> LENGTH: 72
<212> TYPE: PRT
<213> ORGANISM: HCV 1a E2;A1-11

<400> SEQUENCE: 12

Thr Thr Asp Ile Ser Gly Lys Thr Ala Ala Arg Ala Ala Ala Gly Leu
1               5                   10                  15

Ala Asn Ile Phe Ser Pro Gly Ala Lys Gln Asn Ile Gln Leu Val Asn
            20                  25                  30

Thr Asn Gly Ser Trp His Ile Asn Ser Thr Ala Leu Asn Cys Asn Asp
        35                  40                  45

Ser Leu Asn Thr Gly Trp Ile Ala Gly Leu Phe Tyr Arg Tyr Asn Phe
    50                  55                  60

Asn Ser Ser Gly Cys Pro Glu Arg
65                  70

<210> SEQ ID NO 13
<211> LENGTH: 72
<212> TYPE: PRT
<213> ORGANISM: HCV 1a E2 (A1-12)

<400> SEQUENCE: 13

Glu Thr Tyr Val Thr Gly Gly Ala Ala Pro Arg Ala Ala Ala Gly Ile
1               5                   10                  15

Ala Gly Leu Phe Ser Pro Gly Pro Gln Gln Lys Ile Gln Leu Val Asn
            20                  25                  30

Thr Asn Gly Ser Trp His Ile Asn Ser Thr Ala Leu Asn Cys Asn Asp
        35                  40                  45

Ser Leu Asn Thr Gly Trp Ile Ala Gly Leu Phe Tyr Arg Arg Asn Phe
    50                  55                  60

Asn Ser Ser Gly Cys Pro Glu Arg
```

<210> SEQ ID NO 14
<211> LENGTH: 72
<212> TYPE: PRT
<213> ORGANISM: HCV 1a E2 (A1-13)

<400> SEQUENCE: 14

Glu Thr Tyr Val Thr Gly Gly Ala Ala Gly Arg Gly Val Ala Thr Ile
1               5                   10                  15
Thr Gly Leu Phe Ser Pro Gly Pro Gln Gln Lys Ile Gln Leu Val Asn
            20                  25                  30
Thr Asn Gly Ser Trp His Ile Asn Ser Thr Ala Leu Asn Cys Asn Asp
        35                  40                  45
Ser Leu Lys Thr Gly Trp Ile Ala Gly Leu Phe Tyr Arg Tyr Asn Phe
    50                  55                  60
Asn Ser Ser Gly Cys Pro Glu Arg
65                  70

<210> SEQ ID NO 15
<211> LENGTH: 72
<212> TYPE: PRT
<213> ORGANISM: HCV 1a E2 (A1-14)

<400> SEQUENCE: 15

Glu Thr Tyr Val Thr Gly Gly Ala Pro Ala Arg Ala Ala Gly Ile
1               5                   10                  15
Ala Gly Leu Phe Ser Ser Gly Pro Gln Gln Lys Ile Gln Leu Val Asn
            20                  25                  30
Thr Asn Gly Ser Trp His Ile Asn Ser Thr Ala Leu Asn Cys Asn Asp
        35                  40                  45
Ser Leu Asn Thr Gly Trp Ile Ala Gly Leu Phe Tyr Arg Arg Asn Phe
    50                  55                  60
Asn Ser Ser Gly Cys Pro Glu Arg
65                  70

<210> SEQ ID NO 16
<211> LENGTH: 72
<212> TYPE: PRT
<213> ORGANISM: HCV 1a E2 (A1-15)

<400> SEQUENCE: 16

Glu Thr Tyr Val Thr Gly Gly Ala Ala Gly Arg Gly Val Ala Thr Ile
1               5                   10                  15
Thr Gly Leu Phe Ser Pro Gly Pro Gln Gln Lys Ile Gln Leu Val Asn
            20                  25                  30
Thr Asn Gly Ser Trp His Ile Asn Ser Thr Ala Leu Asn Cys Asn Asp
        35                  40                  45
Ser Leu Asn Thr Gly Trp Ile Ala Gly Leu Phe Tyr Arg Arg Asn Phe
    50                  55                  60
Asn Ser Ser Gly Cys Pro Glu Arg
65                  70

<210> SEQ ID NO 17
<211> LENGTH: 72
<212> TYPE: PRT
<213> ORGANISM: HCV 1a E2 (A1-16)

<400> SEQUENCE: 17

```
Thr Tyr Val Thr Gly Gly Val Thr Gly Arg Gly Val Ala Thr Ile
1               5                   10                  15

Ala Gly Leu Phe Ser Ser Gly Pro Gln Gln Lys Ile Gln Leu Val Asn
            20                  25                  30

Thr Asn Gly Ser Trp His Ile Asn Ser Thr Ala Leu Asn Cys Asn Asp
            35                  40                  45

Ser Leu Asn Thr Gly Trp Ile Ala Gly Leu Phe Tyr Arg Tyr Asn Phe
    50                  55                  60

Asn Ser Ser Gly Cys Pro Glu Arg
65                  70
```

<210> SEQ ID NO 18
<211> LENGTH: 72
<212> TYPE: PRT
<213> ORGANISM: HCV 1a E2 (A1-17)

<400> SEQUENCE: 18

```
Gly Thr Tyr Val Thr Gly Gly Val Thr Gly Arg Gly Val Ala Thr Ile
1               5                   10                  15

Ala Gly Leu Phe Ser Ser Gly Pro Gln Gln Lys Ile Gln Leu Val Asn
            20                  25                  30

Thr Asn Gly Ser Trp His Ile Asn Ser Thr Ala Leu Asn Cys Asn Asp
            35                  40                  45

Ser Leu Asn Thr Gly Trp Ile Ala Gly Leu Phe Tyr Arg Arg Asn Phe
    50                  55                  60

Asn Ser Ser Gly Cys Pro Glu Arg
65                  70
```

<210> SEQ ID NO 19
<211> LENGTH: 72
<212> TYPE: PRT
<213> ORGANISM: HCV 1a E2 (A1-18)

<400> SEQUENCE: 19

```
Thr Thr Tyr Val Thr Gly Gly Ser Pro Ala Arg Ala Ala Ala Gly Ile
1               5                   10                  15

Ala Gly Leu Phe Ser Ser Gly Pro Gln Gln Lys Ile Gln Leu Val Asn
            20                  25                  30

Thr Asn Gly Ser Trp His Ile Asn Ser Thr Ala Leu Asn Cys Asn Asp
            35                  40                  45

Ser Leu Asn Thr Gly Trp Ile Ala Gly Leu Phe Tyr Arg Arg Asn Phe
    50                  55                  60

Asn Ser Ser Gly Cys Pro Glu Arg
65                  70
```

<210> SEQ ID NO 20
<211> LENGTH: 72
<212> TYPE: PRT
<213> ORGANISM: HCV 1a E2 (A1-19)

<400> SEQUENCE: 20

```
Thr Thr Tyr Val Thr Gly Gly Ala Pro Ala Arg Ala Ala Ala Ala Phe
1               5                   10                  15

Ala Gly Leu Phe Ser Ser Gly Pro Gln Gln Lys Ile Gln Leu Val Asn
            20                  25                  30

Thr Asn Gly Ser Trp His Ile Asn Ser Thr Ala Leu Asn Cys Asn Asp
            35                  40                  45

Ser Leu Lys Thr Gly Trp Ile Ala Gly Leu Phe Tyr Arg Asn Asn Phe
```

Asn Ser Ser Gly Cys Pro Glu Arg
65                  70

<210> SEQ ID NO 21
<211> LENGTH: 72
<212> TYPE: PRT
<213> ORGANISM: HCV 1a E2 (A1-20)

<400> SEQUENCE: 21

Glu Thr Tyr Val Thr Gly Gly Ala Ala Gly Arg Gly Val Ala Thr Ile
1               5                  10                  15

Thr Gly Leu Phe Ser Pro Gly His Gln Lys Ile Gln Leu Val Asn
            20                  25                  30

Thr Asn Gly Ser Trp His Ile Asn Ser Thr Ala Leu Asn Cys Asn Asp
        35                  40                  45

Ser Leu Lys Thr Gly Trp Ile Ala Gly Leu Phe Tyr Arg Tyr Asn Phe
    50                  55                  60

Asn Ser Ser Gly Cys Pro Glu Arg
65                  70

<210> SEQ ID NO 22
<211> LENGTH: 72
<212> TYPE: PRT
<213> ORGANISM: HCV 1a E2 (A1-21)

<400> SEQUENCE: 22

Thr Thr Tyr Val Thr Gly Gly Thr Pro Ala Arg Ala Ala Ala Gly Ile
1               5                  10                  15

Ala Gly Leu Phe Ser Ser Gly Pro Gln Gln Lys Ile Gln Leu Val Asn
            20                  25                  30

Thr Asn Gly Ser Trp His Ile Asn Ser Thr Ala Leu Asn Cys Asn Asp
        35                  40                  45

Ser Leu Asn Thr Gly Trp Ile Ala Gly Leu Phe Tyr Arg Arg Asn Phe
    50                  55                  60

Asn Ser Ser Gly Cys Pro Glu Arg
65                  70

<210> SEQ ID NO 23
<211> LENGTH: 72
<212> TYPE: PRT
<213> ORGANISM: HCV 1a E2 (A1-22)

<400> SEQUENCE: 23

Thr Thr Tyr Val Thr Gly Gly Ala Pro Ala Arg Ala Ala Ala Gly Ile
1               5                  10                  15

Thr Gly Leu Leu Ser Ser Gly Pro Gln Gln Lys Ile Gln Leu Val Asn
            20                  25                  30

Thr Asn Gly Ser Trp His Ile Asn Ser Thr Ala Leu Asn Cys Asn Asp
        35                  40                  45

Ser Leu Asn Thr Gly Trp Ile Ala Gly Leu Phe Tyr Arg Arg Asn Phe
    50                  55                  60

Asn Ser Ser Gly Cys Pro Glu Arg
65                  70

<210> SEQ ID NO 24
<211> LENGTH: 72
<212> TYPE: PRT
<213> ORGANISM: HCV 1a E2 (A1-23)

<400> SEQUENCE: 24

Glu Thr Tyr Val Thr Gly Gly Ala Ala Ala Arg Gly Val Ala Thr Ile
1               5                   10                  15

Ala Gly Leu Phe Ser Pro Gly Pro Gln Gln Lys Ile Gln Leu Val Asn
            20                  25                  30

Thr Asn Gly Ser Trp His Ile Asn Ser Thr Ala Leu Asn Cys Asn Asp
        35                  40                  45

Ser Leu Lys Thr Gly Trp Ile Ala Gly Leu Phe Tyr Arg Arg Asn Phe
    50                  55                  60

Asn Ser Ser Gly Cys Pro Glu Arg
65                  70

<210> SEQ ID NO 25
<211> LENGTH: 72
<212> TYPE: PRT
<213> ORGANISM: HCV 1a E2 (A1-24)

<400> SEQUENCE: 25

Thr Thr Tyr Val Thr Gly Gly Val Thr Gly Arg Gly Val Ala Thr Ile
1               5                   10                  15

Thr Gly Leu Phe Ser Pro Gly Pro Gln Gln Lys Ile Gln Leu Val Asn
            20                  25                  30

Thr Asn Gly Ser Trp His Ile Asn Ser Thr Ala Leu Asn Cys Asn Asp
        35                  40                  45

Ser Leu Asn Thr Gly Trp Ile Ala Gly Leu Phe Tyr Arg Arg Asn Phe
    50                  55                  60

Asn Ser Ser Gly Cys Pro Glu Arg
65                  70

<210> SEQ ID NO 26
<211> LENGTH: 72
<212> TYPE: PRT
<213> ORGANISM: HCV 1a E2 (A2-1)

<400> SEQUENCE: 26

Thr Thr Tyr Val Thr Gly Lys Thr Ala Gly Arg Gly Val Ala Gly Leu
1               5                   10                  15

Ala Asn Ile Phe Ser Pro Gly Ala Lys Gln Asn Ile Gln Leu Val Asn
            20                  25                  30

Ile Asn Gly Ser Trp His Ile Asn Ser Thr Ala Leu Asn Cys Asn Asp
        35                  40                  45

Ser Leu Asn Thr Gly Trp Ile Ala Gly Leu Phe Tyr Arg Tyr Asn Phe
    50                  55                  60

Asn Ser Ser Gly Cys Pro Glu Arg
65                  70

<210> SEQ ID NO 27
<211> LENGTH: 72
<212> TYPE: PRT
<213> ORGANISM: HCV 1a E2 (A2-2)

<400> SEQUENCE: 27

Thr Thr Tyr Val Thr Gly Gly Ala Pro Gly Arg Gly Val Ala Thr Ile
1               5                   10                  15

Ala Gly Leu Phe Ser Pro Gly Pro Gln Gln Lys Ile Gln Leu Val Asn
            20                  25                  30

Thr Asn Gly Ser Trp His Ile Asn Ser Thr Ala Leu Asn Cys Asn Asp

```
                    35                  40                  45
Ser Leu Asn Thr Gly Trp Ile Ala Gly Leu Phe Tyr Arg Asn Asn Phe
    50                  55                  60

Asn Ser Ser Gly Cys Pro Glu Arg
65                  70

<210> SEQ ID NO 28
<211> LENGTH: 72
<212> TYPE: PRT
<213> ORGANISM: HCV 1a E2 (A2-3)

<400> SEQUENCE: 28

Thr Thr Tyr Val Thr Gly Gly Ala Ala Gly Arg Gly Val Ala Thr Ile
1               5                   10                  15

Thr Gly Leu Phe Ser Pro Gly Pro His Gln Lys Ile Gln Leu Val Asn
                20                  25                  30

Thr Asn Gly Ser Trp His Ile Asn Ser Thr Ala Leu Asn Cys Asn Asp
            35                  40                  45

Ser Leu Lys Thr Gly Trp Ile Ala Gly Leu Phe Tyr Arg Asn Asn Phe
    50                  55                  60

Asn Ser Ser Gly Cys Pro Glu Arg
65                  70

<210> SEQ ID NO 29
<211> LENGTH: 72
<212> TYPE: PRT
<213> ORGANISM: HCV 1a E2 (A2-4)

<400> SEQUENCE: 29

Thr Thr Tyr Val Thr Gly Gly Val Thr Gly Arg Gly Val Ala Thr Ile
1               5                   10                  15

Ala Gly Leu Phe Ser Pro Gly Pro Gln Gln Lys Ile Gln Leu Val Asn
                20                  25                  30

Thr Asn Gly Ser Trp His Ile Asn Ser Thr Ala Leu Asn Cys Asn Asp
            35                  40                  45

Ser Leu Asn Thr Gly Trp Ile Ala Gly Leu Phe Tyr Arg Arg Asn Phe
    50                  55                  60

Asn Ser Ser Gly Cys Pro Glu Arg
65                  70

<210> SEQ ID NO 30
<211> LENGTH: 72
<212> TYPE: PRT
<213> ORGANISM: HCV 1a E2 (A2-5)

<400> SEQUENCE: 30

Glu Thr Tyr Val Thr Gly Gly Ala Ala Gly Arg Gly Val Ala Thr Ile
1               5                   10                  15

Thr Gly Leu Phe Ser Gln Gly Pro Gln Gln Lys Ile Gln Leu Val Asn
                20                  25                  30

Thr Asn Gly Ser Trp His Ile Asn Ser Thr Ala Leu Asn Cys Asn Asp
            35                  40                  45

Ser Leu Asn Thr Gly Trp Ile Ala Gly Leu Phe Tyr Arg Arg Asn Phe
    50                  55                  60

Asn Ser Ser Gly Cys Pro Glu Arg
65                  70

<210> SEQ ID NO 31
```

```
<211> LENGTH: 72
<212> TYPE: PRT
<213> ORGANISM: HCV 1a E2 (A2-6)

<400> SEQUENCE: 31

Glu Thr Tyr Val Thr Gly Gly Ala Ala Gly Arg Gly Val Ala Thr Ile
1               5                   10                  15

Thr Gly Leu Phe Ser Ala Gly Pro Gln Gln Lys Ile Gln Leu Val Asn
            20                  25                  30

Thr Asn Gly Ser Trp His Ile Asn Ser Thr Ala Leu Asn Cys Asn Asp
        35                  40                  45

Ser Leu Asn Thr Gly Trp Ile Ala Gly Leu Phe Tyr Arg Arg Asn Phe
    50                  55                  60

Asn Ser Ser Gly Cys Pro Glu Arg
65                  70

<210> SEQ ID NO 32
<211> LENGTH: 72
<212> TYPE: PRT
<213> ORGANISM: HCV 1a E2 (A2-7)

<400> SEQUENCE: 32

Ala Thr Tyr Val Thr Gly Gly Val Thr Gly Arg Gly Val Ala Thr Ile
1               5                   10                  15

Thr Gly Leu Phe Ser Ala Gly Pro Gln Gln Lys Ile Gln Leu Val Asn
            20                  25                  30

Thr Asn Gly Ser Trp His Ile Asn Ser Thr Ala Leu Asn Cys Asn Asp
        35                  40                  45

Ser Leu Asn Thr Gly Trp Ile Ala Gly Leu Phe Tyr Arg Tyr Asn Phe
    50                  55                  60

Asn Ser Ser Gly Cys Pro Glu Arg
65                  70

<210> SEQ ID NO 33
<211> LENGTH: 72
<212> TYPE: PRT
<213> ORGANISM: HCV 1a E2;A2-8

<400> SEQUENCE: 33

Ala Thr Tyr Thr Ser Gly Gly Val Ala Gly Arg Gly Thr Ala Gly Leu
1               5                   10                  15

Ala Ser Leu Phe Ser Pro Gly Pro His Gln Lys Ile Gln Leu Val Asn
            20                  25                  30

Ile Asn Gly Ser Trp His Ile Asn Ser Thr Ala Leu Asn Cys Asn Asp
        35                  40                  45

Ser Leu Asn Thr Gly Trp Ile Ala Gly Leu Phe Tyr Arg Tyr Asn Phe
    50                  55                  60

Asn Ser Ser Gly Cys Pro Glu Arg
65                  70

<210> SEQ ID NO 34
<211> LENGTH: 72
<212> TYPE: PRT
<213> ORGANISM: HCV 1a E2 (A2-9)

<400> SEQUENCE: 34

Ser Thr Tyr Val Thr Gly Gly Val Ala Gly Arg Gln Thr Ala Gly Leu
1               5                   10                  15

Ala Ser Leu Phe Ser Pro Gly Pro His Gln Lys Ile Gln Leu Val Asn
```

-continued

```
                    20                  25                  30

Ile Asn Gly Ser Trp His Ile Asn Ser Thr Ala Leu Asn Cys Asn Asp
            35                  40                  45

Ser Leu Asn Thr Gly Trp Ile Ala Gly Leu Phe Tyr Arg Arg Asn Phe
    50                  55                  60

Asn Ser Ser Gly Cys Pro Glu Arg
65                  70

<210> SEQ ID NO 35
<211> LENGTH: 72
<212> TYPE: PRT
<213> ORGANISM: HCV 1a E2 (A2-10)

<400> SEQUENCE: 35

Thr Thr Tyr Val Thr Gly Gly Val Thr Gly Arg Gly Val Ala Thr Ile
1               5                   10                  15

Ala Gly Leu Phe Ser Ser Gly Pro Gln Gln Lys Ile Gln Leu Val Asn
            20                  25                  30

Thr Asn Gly Ser Trp His Ile Asn Ser Thr Ala Leu Asn Cys Asn Asp
            35                  40                  45

Ser Leu Asn Thr Gly Trp Ile Ala Gly Leu Phe Tyr Arg Arg Asn Phe
    50                  55                  60

Asn Ser Ser Gly Cys Pro Glu Arg
65                  70

<210> SEQ ID NO 36
<211> LENGTH: 72
<212> TYPE: PRT
<213> ORGANISM: HCV 1a E2 (A2-11)

<400> SEQUENCE: 36

Ala Thr Tyr Val Thr Gly Gly Val Thr Gly Arg Gly Val Ala Thr Ile
1               5                   10                  15

Thr Gly Leu Phe Ser Ala Gly Pro Gln Gln Lys Ile Gln Leu Val Asn
            20                  25                  30

Thr Asn Gly Ser Trp His Ile Asn Ser Thr Ala Leu Asn Cys Asn Asp
            35                  40                  45

Ser Leu Asn Thr Gly Trp Ile Ala Gly Leu Phe Tyr Arg Tyr Asn Phe
    50                  55                  60

Asn Ser Ser Gly Cys Pro Glu Arg
65                  70

<210> SEQ ID NO 37
<211> LENGTH: 72
<212> TYPE: PRT
<213> ORGANISM: HCV 1a E2 (A2-12)

<400> SEQUENCE: 37

Ser Thr Tyr Val Thr Gly Gly Val Ala Gly Arg Gln Thr Ala Gly Leu
1               5                   10                  15

Ala Ser Leu Phe Ser Pro Gly Ala His Gln Lys Ile Gln Leu Val Asn
            20                  25                  30

Thr Asn Gly Ser Trp His Ile Asn Ser Thr Ala Leu Asn Cys Asn Asp
            35                  40                  45

Ser Leu Asn Thr Gly Trp Ile Ala Gly Leu Phe Tyr Arg Arg Asn Phe
    50                  55                  60

Asn Ser Ser Gly Cys Pro Glu Arg
65                  70
```

<210> SEQ ID NO 38
<211> LENGTH: 72
<212> TYPE: PRT
<213> ORGANISM: HCV 1a E2 (A2-13)

<400> SEQUENCE: 38

Thr Thr Tyr Val Thr Gly Gly Val Thr Gly Arg Gly Val Ala Thr Ile
1               5                   10                  15

Thr Gly Leu Phe Ser Ser Gly Pro Gln Gln Lys Ile Gln Leu Val Asn
            20                  25                  30

Thr Asn Gly Ser Trp His Ile Asn Ser Thr Ala Leu Asn Cys Asn Asp
        35                  40                  45

Ser Leu Asn Thr Gly Trp Ile Ala Gly Leu Phe Tyr Arg Tyr Asn Phe
    50                  55                  60

Asn Ser Ser Gly Cys Pro Glu Arg
65                  70

<210> SEQ ID NO 39
<211> LENGTH: 72
<212> TYPE: PRT
<213> ORGANISM: HCV 1a E2 (A2-14)

<400> SEQUENCE: 39

Thr Thr Tyr Val Thr Gly Gly Ala Pro Gly Arg Gly Val Ala Thr Ile
1               5                   10                  15

Ala Gly Leu Phe Ser Ser Gly Pro Gln Gln Lys Ile Gln Leu Val Asn
            20                  25                  30

Thr Asn Gly Ser Trp His Ile Asn Ser Thr Ala Leu Asn Cys Asn Asp
        35                  40                  45

Ser Leu Asn Thr Gly Trp Ile Ala Gly Leu Phe Tyr Arg Arg Asn Phe
    50                  55                  60

Asn Ser Ser Gly Cys Pro Glu Arg
65                  70

<210> SEQ ID NO 40
<211> LENGTH: 72
<212> TYPE: PRT
<213> ORGANISM: HCV 1a E2 (A2-15)

<400> SEQUENCE: 40

Thr Thr Tyr Val Thr Gly Gly Val Thr Gly Arg Gly Val Ala Thr Ile
1               5                   10                  15

Ala Gly Leu Phe Ser Ser Gly Pro Gln Gln Lys Ile Gln Leu Val Asn
            20                  25                  30

Thr Asn Gly Ser Trp His Ile Asn Ser Thr Ala Leu Asn Cys Asn Asp
        35                  40                  45

Ser Leu Asn Thr Gly Trp Ile Ala Gly Leu Phe Tyr Arg Arg Asn Phe
    50                  55                  60

Asn Ser Ser Gly Cys Pro Glu Arg
65                  70

<210> SEQ ID NO 41
<211> LENGTH: 72
<212> TYPE: PRT
<213> ORGANISM: HCV 1a E2 (A2-16)

<400> SEQUENCE: 41

Thr Thr Tyr Val Thr Gly Gly Ala Ala Gly Arg Gly Val Ala Thr Ile

```
                1               5                  10                 15
Thr Gly Leu Phe Ser Ala Gly Pro Gln Gln Lys Ile Gln Leu Val Asn
                    20                  25                  30

Thr Asn Gly Ser Trp His Ile Asn Ser Thr Ala Leu Asn Cys Asn Asp
                    35                  40                  45

Ser Leu Lys Thr Gly Trp Ile Ala Gly Leu Phe Tyr Arg Tyr Asn Phe
                    50                  55                  60

Asn Ser Ser Gly Cys Pro Glu Arg
65                      70

<210> SEQ ID NO 42
<211> LENGTH: 72
<212> TYPE: PRT
<213> ORGANISM: HCV 1a E2 (A2-17)

<400> SEQUENCE: 42

Thr Thr Tyr Val Thr Gly Gly Val Thr Gly Arg Gly Val Ala Thr Ile
1               5                   10                  15

Thr Gly Leu Phe Ser Pro Gly Pro Gln Gln Lys Ile Gln Leu Val Asn
                    20                  25                  30

Thr Asn Gly Ser Trp His Ile Asn Ser Thr Ala Leu Asn Cys Asn Asp
                    35                  40                  45

Ser Leu Asn Thr Gly Trp Ile Ala Gly Leu Phe Tyr Arg Arg Asn Phe
                    50                  55                  60

Asn Ser Ser Gly Cys Pro Glu Arg
65                      70

<210> SEQ ID NO 43
<211> LENGTH: 72
<212> TYPE: PRT
<213> ORGANISM: HCV 1a E2 (A2-18)

<400> SEQUENCE: 43

Thr Thr Tyr Val Thr Gly Gly Val Thr Gly Arg Gly Val Ala Thr Ile
1               5                   10                  15

Thr Gly Leu Phe Ser Ala Gly Pro Gln Gln Lys Ile Gln Leu Val Asn
                    20                  25                  30

Thr Asn Gly Ser Trp His Ile Asn Ser Thr Ala Leu Asn Cys Asn Asp
                    35                  40                  45

Ser Leu Asn Thr Gly Trp Ile Ala Gly Leu Phe Tyr Arg Asn Asn Phe
                    50                  55                  60

Asn Ser Ser Gly Cys Pro Glu Arg
65                      70

<210> SEQ ID NO 44
<211> LENGTH: 72
<212> TYPE: PRT
<213> ORGANISM: HCV 1a E2 (A2-19)

<400> SEQUENCE: 44

Ala Thr Tyr Val Thr Gly Ala Val Thr Gly Arg Gly Ala Ala Gly Ile
1               5                   10                  15

Ala Asp Leu Phe Ser Leu Gly Pro Gln Gln Lys Ile Gln Leu Val Asn
                    20                  25                  30

Thr Asn Gly Ser Trp His Ile Asn Ser Thr Ala Leu Asn Cys Asn Asp
                    35                  40                  45

Ser Leu Asn Thr Gly Trp Ile Ala Gly Leu Phe Tyr Arg Arg Asn Phe
                    50                  55                  60
```

Asn Ser Ser Gly Cys Pro Glu Arg
65                  70

<210> SEQ ID NO 45
<211> LENGTH: 72
<212> TYPE: PRT
<213> ORGANISM: HCV 1a E2 (A2-20)

<400> SEQUENCE: 45

Glu Thr Tyr Val Thr Gly Gly Ala Ala Gly Arg Gly Val Ala Thr Ile
1               5                   10                  15

Thr Gly Leu Phe Ser Gln Gly Pro Gln Gln Lys Ile Gln Leu Val Asn
            20                  25                  30

Thr Asn Gly Ser Trp His Ile Asn Ser Thr Ala Leu Asn Cys Asn Asp
        35                  40                  45

Ser Leu Asn Thr Gly Trp Ile Ala Gly Leu Phe Tyr Arg Asn Asn Phe
    50                  55                  60

Asn Ser Ser Gly Cys Pro Glu Arg
65                  70

<210> SEQ ID NO 46
<211> LENGTH: 72
<212> TYPE: PRT
<213> ORGANISM: HCV 1a E2 (A2-21)

<400> SEQUENCE: 46

Glu Thr Tyr Val Thr Gly Gly Ala Ala Gly Arg Gly Val Ala Thr Ile
1               5                   10                  15

Thr Gly Leu Phe Ser Ala Gly Pro Gln Gln Lys Ile Gln Leu Val Asn
            20                  25                  30

Thr Asn Gly Ser Trp His Ile Asn Ser Thr Ala Leu Asn Cys Asn Asp
        35                  40                  45

Ser Leu Lys Thr Gly Trp Ile Ala Gly Leu Phe Tyr Arg Asn Asn Phe
    50                  55                  60

Asn Ser Ser Gly Cys Pro Glu Arg
65                  70

<210> SEQ ID NO 47
<211> LENGTH: 72
<212> TYPE: PRT
<213> ORGANISM: HCV 1a E2 (A2-22)

<400> SEQUENCE: 47

Glu Thr Tyr Val Thr Gly Gly Ala Ala Gly Arg Gly Val Ala Thr Ile
1               5                   10                  15

Ala Gly Leu Phe Ser Pro Gly Pro Gln Gln Lys Ile Gln Leu Val Asn
            20                  25                  30

Thr Asn Gly Ser Trp His Ile Asn Ser Thr Ala Leu Asn Cys Asn Asp
        35                  40                  45

Ser Leu Lys Thr Gly Trp Ile Ala Gly Leu Phe Tyr Arg Asn Asn Phe
    50                  55                  60

Asn Ser Ser Gly Cys Pro Glu Arg
65                  70

<210> SEQ ID NO 48
<211> LENGTH: 72
<212> TYPE: PRT
<213> ORGANISM: HCV 1a E2 (A2-23)

```
<400> SEQUENCE: 48

Glu Thr Tyr Val Thr Gly Gly Ala Ala Gly Arg Gly Val Ala Thr Ile
1               5                   10                  15

Ala Gly Leu Phe Ser Ser Gly Pro Gln Gln Lys Ile Gln Leu Val Asn
            20                  25                  30

Thr Asn Gly Ser Trp His Ile Asn Ser Thr Ala Leu Asn Cys Asn Asp
        35                  40                  45

Ser Leu Asn Thr Gly Trp Ile Ala Gly Leu Phe Tyr Arg Arg Asn Phe
    50                  55                  60

Asn Ser Ser Gly Cys Pro Glu Arg
65                  70

<210> SEQ ID NO 49
<211> LENGTH: 72
<212> TYPE: PRT
<213> ORGANISM: HCV 1a E2 (A3-1)

<400> SEQUENCE: 49

Ala Thr Tyr Val Thr Gly Gly Val Thr Gly Arg Gly Val Ala Thr Ile
1               5                   10                  15

Thr Gly Leu Phe Ser Gln Gly Pro Gln Gln Lys Ile Gln Leu Val Asn
            20                  25                  30

Thr Asn Gly Ser Trp His Ile Asn Ser Thr Ala Leu Asn Cys Asn Asp
        35                  40                  45

Ser Leu Asn Thr Gly Trp Ile Ala Gly Leu Phe Tyr Arg Asn Asn Phe
    50                  55                  60

Asn Ser Ser Gly Cys Pro Glu Arg
65                  70

<210> SEQ ID NO 50
<211> LENGTH: 72
<212> TYPE: PRT
<213> ORGANISM: HCV 1a E2 (A3-2)

<400> SEQUENCE: 50

Ala Thr Tyr Val Thr Gly Gly Ala Ala Gly Arg Gly Val Ala Thr Ile
1               5                   10                  15

Thr Gly Leu Phe Ser Ala Gly Pro Gln Gln Lys Ile Gln Leu Val Asn
            20                  25                  30

Thr Asn Gly Ser Trp His Ile Asn Ser Thr Ala Leu Asn Cys Asn Asp
        35                  40                  45

Ser Leu Asn Thr Gly Trp Ile Ala Gly Leu Phe Tyr Arg Asn Asn Phe
    50                  55                  60

Asn Ser Ser Gly Cys Pro Glu Arg
65                  70

<210> SEQ ID NO 51
<211> LENGTH: 72
<212> TYPE: PRT
<213> ORGANISM: HCV 1a E2 (A3-3)

<400> SEQUENCE: 51

Glu Thr Tyr Val Thr Gly Gly Ala Ala Gly Arg Gly Val Ala Thr Ile
1               5                   10                  15

Thr Gly Leu Phe Ser Ala Gly Pro Gln Gln Lys Ile Gln Leu Val Asn
            20                  25                  30

Thr Asn Gly Ser Trp His Ile Asn Ser Thr Ala Leu Asn Cys Asn Asp
        35                  40                  45
```

Ser Leu Asn Thr Gly Trp Ile Ala Gly Leu Phe Tyr Arg Asn Asn Phe
    50                  55                  60

Asn Ser Ser Gly Cys Pro Glu Arg
65                  70

<210> SEQ ID NO 52
<211> LENGTH: 72
<212> TYPE: PRT
<213> ORGANISM: HCV 1a E2 (A3-4)

<400> SEQUENCE: 52

Ala Thr Tyr Val Thr Gly Gly Ala Ala Gly Arg Gly Val Ala Thr Ile
1               5                   10                  15

Thr Gly Leu Phe Ser Gln Gly Pro Gln Gln Lys Ile Gln Leu Val Asn
            20                  25                  30

Thr Asn Gly Ser Trp His Ile Asn Ser Thr Ala Leu Asn Cys Asn Asp
        35                  40                  45

Ser Leu Asn Thr Gly Trp Ile Ala Gly Leu Phe Tyr Arg Asn Asn Phe
    50                  55                  60

Asn Ser Ser Gly Cys Pro Glu Arg
65                  70

<210> SEQ ID NO 53
<211> LENGTH: 72
<212> TYPE: PRT
<213> ORGANISM: HCV 1a E2 (A3-5)

<400> SEQUENCE: 53

Ala Thr Tyr Val Thr Gly Gly Ala Ala Gly Arg Gly Val Ala Thr Ile
1               5                   10                  15

Thr Gly Leu Phe Ser Gln Gly Pro Gln Gln Lys Ile Gln Leu Val Asn
            20                  25                  30

Thr Asn Gly Ser Trp His Ile Asn Ser Thr Ala Leu Asn Cys Asn Asp
        35                  40                  45

Ser Leu Lys Thr Gly Trp Ile Ala Gly Leu Phe Tyr Arg Asn Asn Phe
    50                  55                  60

Asn Ser Ser Gly Cys Pro Glu Arg
65                  70

<210> SEQ ID NO 54
<211> LENGTH: 72
<212> TYPE: PRT
<213> ORGANISM: HCV 1a E2 (A3-6)

<400> SEQUENCE: 54

Ala Thr Tyr Val Thr Gly Gly Val Thr Gly Arg Gly Val Ala Thr Ile
1               5                   10                  15

Thr Gly Leu Phe Ser Gln Gly Pro Gln Gln Lys Ile Gln Leu Val Asn
            20                  25                  30

Thr Asn Gly Ser Trp His Ile Asn Ser Thr Ala Leu Asn Cys Asn Asp
        35                  40                  45

Ser Leu Lys Thr Gly Trp Ile Ala Gly Leu Phe Tyr Arg Asn Asn Phe
    50                  55                  60

Asn Ser Ser Gly Cys Pro Glu Arg
65                  70

<210> SEQ ID NO 55
<211> LENGTH: 72

```
<212> TYPE: PRT
<213> ORGANISM: HCV 1a E2 (A3-7)

<400> SEQUENCE: 55

Thr Thr Tyr Val Thr Gly Gly Val Thr Gly Arg Gly Val Ala Thr Ile
1               5                   10                  15

Ala Gly Leu Phe Ser Ser Gly Pro Gln Gln Lys Ile Gln Leu Val Asn
            20                  25                  30

Thr Asn Gly Ser Trp His Ile Asn Ser Thr Ala Leu Asn Cys Asn Asp
        35                  40                  45

Ser Leu Asn Thr Gly Trp Ile Ala Gly Leu Phe Tyr Arg Asn Asn Phe
    50                  55                  60

Asn Ser Ser Gly Cys Pro Glu Arg
65                  70

<210> SEQ ID NO 56
<211> LENGTH: 72
<212> TYPE: PRT
<213> ORGANISM: HCV 1a E2 (A3-8)

<400> SEQUENCE: 56

Ala Thr Tyr Val Thr Gly Gly Val Thr Gly Arg Gly Val Ala Thr Ile
1               5                   10                  15

Thr Gly Leu Phe Ser Ser Gly Pro Gln Gln Lys Ile Gln Leu Val Asn
            20                  25                  30

Thr Asn Gly Ser Trp His Ile Asn Ser Thr Ala Leu Asn Cys Asn Asp
        35                  40                  45

Ser Leu Asn Thr Gly Trp Ile Ala Gly Leu Phe Tyr Arg Arg Asn Phe
    50                  55                  60

Asn Ser Ser Gly Cys Pro Glu Arg
65                  70

<210> SEQ ID NO 57
<211> LENGTH: 72
<212> TYPE: PRT
<213> ORGANISM: HCV 1a E2 (A3-9)

<400> SEQUENCE: 57

Glu Thr Tyr Val Thr Gly Gly Ala Ala Gly Arg Gly Val Ala Thr Ile
1               5                   10                  15

Thr Gly Leu Phe Ser Ala Gly Pro Gln Gln Lys Ile Gln Leu Val Asn
            20                  25                  30

Thr Asn Gly Ser Trp His Ile Asn Ser Thr Ala Leu Asn Cys Asn Asp
        35                  40                  45

Ser Leu Asn Thr Gly Trp Ile Ala Gly Leu Phe Tyr Arg Asn Asn Phe
    50                  55                  60

Asn Ser Ser Gly Cys Pro Glu Arg
65                  70

<210> SEQ ID NO 58
<211> LENGTH: 72
<212> TYPE: PRT
<213> ORGANISM: HCV 1a E2 (A4-1)

<400> SEQUENCE: 58

Thr Thr Asp Ile Ser Gly Lys Thr Ala Ala Arg Ala Ala Ala Gly Phe
1               5                   10                  15

Thr Asn Ile Phe Ser Pro Gly Ala Lys Gln Asn Ile Gln Leu Val Asn
            20                  25                  30
```

Thr Asn Gly Ser Trp His Ile Asn Ser Thr Ala Leu Asn Cys Asn Asp
            35                  40                  45

Ser Leu Asn Thr Gly Trp Ile Ala Gly Leu Phe Tyr Arg Tyr Asn Phe
        50                  55                  60

Asn Ser Ser Gly Cys Pro Glu Arg
65                  70

<210> SEQ ID NO 59
<211> LENGTH: 72
<212> TYPE: PRT
<213> ORGANISM: HCV 1a E2 (A4-2)

<400> SEQUENCE: 59

Thr Thr Asp Ile Ser Gly Lys Thr Ala Ala Arg Val Ala Ala Gly Phe
1               5                   10                  15

Thr Asn Ile Phe Ser Pro Gly Ala Lys Gln Asn Ile Gln Leu Val Asn
            20                  25                  30

Thr Asn Gly Ser Trp His Ile Asn Ser Thr Ala Leu Asn Cys Asn Asp
            35                  40                  45

Ser Leu Asn Thr Gly Trp Ile Ala Gly Leu Phe Tyr Arg Tyr Asn Phe
        50                  55                  60

Asn Ser Ser Gly Cys Pro Glu Arg
65                  70

<210> SEQ ID NO 60
<211> LENGTH: 72
<212> TYPE: PRT
<213> ORGANISM: HCV 1a E2 (A4-3)

<400> SEQUENCE: 60

Thr Thr Asp Ile Ser Gly Lys Thr Ala Val Arg Ala Ala Ala Gly Phe
1               5                   10                  15

Thr Asn Ile Phe Ser Pro Gly Ala Lys Gln Asn Ile Gln Leu Val Asn
            20                  25                  30

Thr Asn Gly Ser Trp His Ile Asn Ser Thr Ala Leu Asn Cys Asn Asp
            35                  40                  45

Ser Leu Asn Thr Gly Trp Ile Ala Gly Leu Phe Tyr Arg Tyr Asn Phe
        50                  55                  60

Asn Ser Ser Gly Cys Pro Glu Arg
65                  70

<210> SEQ ID NO 61
<211> LENGTH: 72
<212> TYPE: PRT
<213> ORGANISM: HCV 1a E2 (A5-1)

<400> SEQUENCE: 61

Thr Thr Asp Thr Ser Gly Arg Thr Ala Ala Arg Ala Ala Ala Gly Leu
1               5                   10                  15

Thr Thr Ile Phe Ser Pro Gly Ala Lys Gln Asn Ile Gln Leu Val Asn
            20                  25                  30

Thr Asn Gly Ser Trp His Ile Asn Ser Thr Ala Leu Asn Cys Asn Asp
            35                  40                  45

Ser Leu Asn Thr Gly Trp Ile Ala Gly Leu Phe Tyr Tyr Asn Asn Phe
        50                  55                  60

Asn Ser Ser Gly Cys Pro Glu Arg
65                  70

```
<210> SEQ ID NO 62
<211> LENGTH: 72
<212> TYPE: PRT
<213> ORGANISM: HCV 1a E2 (A5-2)

<400> SEQUENCE: 62

Thr Thr Asp Thr Ser Gly Arg Thr Ala Ala Arg Ala Ala Ala Gly Phe
1               5                   10                  15

Thr Thr Ile Phe Ser Pro Gly Ala Lys Gln Asn Ile Gln Leu Val Asn
                20                  25                  30

Thr Asn Gly Ser Trp His Ile Asn Ser Thr Ala Leu Asn Cys Asn Asp
            35                  40                  45

Ser Leu Asn Thr Gly Trp Ile Ala Gly Leu Phe Tyr Tyr Asn Asn Phe
        50                  55                  60

Asn Ser Ser Gly Cys Pro Glu Arg
65                  70

<210> SEQ ID NO 63
<211> LENGTH: 72
<212> TYPE: PRT
<213> ORGANISM: HCV 1a E2 (A5-3)

<400> SEQUENCE: 63

Thr Thr Asp Thr Ser Gly Arg Thr Ala Ala Arg Ala Ala Ala Arg Leu
1               5                   10                  15

Thr Thr Ile Phe Ser Pro Gly Ala Lys Gln Asn Ile Gln Leu Val Asn
                20                  25                  30

Thr Asn Gly Ser Trp His Ile Asn Ser Thr Ala Leu Asn Cys Asn Asp
            35                  40                  45

Ser Leu Asn Thr Gly Trp Ile Ala Gly Leu Phe Tyr Tyr Asn Asn Phe
        50                  55                  60

Asn Ser Ser Gly Cys Pro Glu Arg
65                  70

<210> SEQ ID NO 64
<211> LENGTH: 40
<212> TYPE: PRT
<213> ORGANISM: HCV NS5A ISDR (3-1)

<400> SEQUENCE: 64

Pro Ser Leu Lys Ala Thr Cys Thr Thr Cys His Asp Ser Pro Asp Ala
1               5                   10                  15

Asp Leu Ile Glu Ala Asn Leu Leu Trp Arg Gln Glu Met Gly Gly Asn
                20                  25                  30

Ile Thr Arg Val Glu Ser Glu Asn
            35                  40

<210> SEQ ID NO 65
<211> LENGTH: 40
<212> TYPE: PRT
<213> ORGANISM: HCV NS5A ISDR (17-1)

<400> SEQUENCE: 65

Pro Ser Leu Lys Ala Thr Cys Thr Thr His His Asp Ser Pro Asp Val
1               5                   10                  15

Asp Leu Ile Glu Ala Asn Leu Leu Trp Arg Gln Glu Met Gly Gly Asn
                20                  25                  30

Ile Thr Arg Val Glu Ser Glu Asn
            35                  40
```

<210> SEQ ID NO 66
<211> LENGTH: 40
<212> TYPE: PRT
<213> ORGANISM: HCV NS5A ISDR (56-1)

<400> SEQUENCE: 66

Pro Ser Leu Lys Ala Thr Cys Thr Thr Arg His Ala Ser Pro Asp Ala
1               5                   10                  15

Asp Leu Ile Glu Ala Asn Leu Leu Trp Arg Gln Glu Met Gly Gly Asn
            20                  25                  30

Ile Thr Arg Val Glu Ser Glu Asn
        35                  40

<210> SEQ ID NO 67
<211> LENGTH: 40
<212> TYPE: PRT
<213> ORGANISM: HCV NS5A ISDR (56-6)

<400> SEQUENCE: 67

Pro Ser Leu Lys Ala Thr Cys Thr Thr Arg His Ala Ser Pro Asp Ala
1               5                   10                  15

Asp Leu Ile Glu Ala Asn Leu Leu Trp Arg Gln Glu Met Val Gly Asn
            20                  25                  30

Ile Thr Arg Val Glu Ser Glu Asn
        35                  40

<210> SEQ ID NO 68
<211> LENGTH: 40
<212> TYPE: PRT
<213> ORGANISM: HCV NS5A ISDR (65-1)

<400> SEQUENCE: 68

Pro Ser Leu Lys Ala Thr Cys Thr Ala Asn His Asp Ser Pro Asp Glu
1               5                   10                  15

Asp Leu Ile Glu Ala Asn Leu Leu Trp Arg Gln Glu Met Gly Gly Asn
            20                  25                  30

Ile Thr Arg Val Glu Ser Glu Asn
        35                  40

<210> SEQ ID NO 69
<211> LENGTH: 40
<212> TYPE: PRT
<213> ORGANISM: HCV NS5A ISDR (65-2)

<400> SEQUENCE: 69

Pro Ser Leu Lys Ala Thr Cys Thr Ala Asn His Asp Ser Pro Asp Glu
1               5                   10                  15

Asp Leu Ile Glu Ala Asn Leu Pro Trp Arg Gln Glu Met Gly Gly Asn
            20                  25                  30

Ile Thr Arg Val Glu Ser Glu Asn
        35                  40

<210> SEQ ID NO 70
<211> LENGTH: 72
<212> TYPE: PRT
<213> ORGANISM: HCV 1a (patient S group with 17 clones)

<400> SEQUENCE: 70

Glu Thr Tyr Val Thr Gly Gly Ala Ala Gly Arg Gly Val Ala Thr Ile
1               5                   10                  15

```
Thr Gly Leu Phe Ser Gln Gly Pro Gln Gln Lys Ile Gln Leu Val Asn
            20                  25                  30

Thr Asn Gly Ser Trp His Ile Asn Ser Thr Ala Leu Asn Cys Asn Asp
        35                  40                  45

Ser Leu Lys Thr Gly Trp Ile Ala Gly Leu Phe Tyr Arg Asn Asn Phe
    50                  55                  60

Asn Ser Ser Gly Cys Pro Glu Arg
65                  70

<210> SEQ ID NO 71
<211> LENGTH: 72
<212> TYPE: PRT
<213> ORGANISM: HCV 1a (patient S group with 3 clones)

<400> SEQUENCE: 71

Glu Thr Tyr Val Thr Gly Gly Ala Ala Gly Arg Gly Val Ala Thr Ile
1               5                   10                  15

Ala Gly Leu Phe Ser Gln Gly Pro Gln Gln Lys Ile Gln Leu Val Asn
            20                  25                  30

Thr Asn Gly Ser Trp His Ile Asn Ser Thr Ala Leu Asn Cys Asn Asp
        35                  40                  45

Ser Leu Lys Thr Gly Trp Ile Ala Gly Leu Leu Tyr Arg Asn Asn Phe
    50                  55                  60

Asn Ser Ser Gly Cys Pro Glu Arg
65                  70

<210> SEQ ID NO 72
<211> LENGTH: 20
<212> TYPE: PRT
<213> ORGANISM: HCV 1a (patient S 10 % of clones)

<400> SEQUENCE: 72

Val Thr Gly Arg Gly Val Ala Thr Ile Thr Gly Leu Phe Ser Gln Gly
1               5                   10                  15

Pro Gln Gln Lys
            20

<210> SEQ ID NO 73
<211> LENGTH: 20
<212> TYPE: PRT
<213> ORGANISM: HCV 1a (patient S 10 % of clones)

<400> SEQUENCE: 73

Ala Ala Gly Arg Gly Val Ala Thr Ile Ala Gly Leu Phe Ser Gln Gly
1               5                   10                  15

Pro Gln Gln Lys
            20

<210> SEQ ID NO 74
<211> LENGTH: 20
<212> TYPE: PRT
<213> ORGANISM: HCV 1a (patient S 5 % of clones)

<400> SEQUENCE: 74

Ala Ala Gly Arg Ala Ala Gly Ile Ala Gly Leu Phe Ser Ser Gly
1               5                   10              15

Pro Gln Gln Lys
            20
```

We claim:

1. A method of characterizing an hepatitis C viral infection, said method comprising:

determining a similarity between a viral sequence of an hypervariable region 1 (HVR1) of the second envelope protein (E2) region of an hepatitis C virus that infected the host and a variable region kappa light chain of an immunoglobulin (IgVLκ) of the host; and wherein, when said similarity is at least 20%, said hepatitis C viral infection is characterized as persistent; and when said similarity is not at least 20%, said hepatitis C viral infection is characterized as acute.

2. The method of claim 1 wherein said host is a mammal.

3. The method of claim 1 wherein said host is a human.

4. The method of claim 1 wherein said immunoglobulin is selected from the group consisting of immunoglobulin class G, A, M, D and E.

5. The method of claim 4 wherein said immunoglobulin is one of a variable region kappa light chain immunoglobulin (IgVLκ) and immunoglobulin G (IgG).

6. The method of claim 4 wherein said immunoglobulin is a human immunoglobulin.

* * * * *